(12) United States Patent
Li et al.

(10) Patent No.: US 11,534,427 B2
(45) Date of Patent: *Dec. 27, 2022

(54) APPLICATIONS OF NOVEL THIAZOLE DERIVATIVE IN TREATING INFLAMMATORY BOWEL DISEASES

(71) Applicant: EAST CHINA UNIVERSITY OF SCIENCE AND TECHNOLOGY, Shanghai (CN)

(72) Inventors: Honglin Li, Shanghai (CN); Zhenjiang Zhao, Shanghai (CN); Rui Wang, Shanghai (CN); Yufang Xu, Shanghai (CN); Wanqi Wang, Shanghai (CN); Yingfang Yang, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/302,574

(22) PCT Filed: May 17, 2017

(86) PCT No.: PCT/CN2017/084749
§ 371 (c)(1),
(2) Date: Nov. 16, 2018

(87) PCT Pub. No.: WO2017/198179
PCT Pub. Date: Nov. 23, 2017

(65) Prior Publication Data
US 2019/0290620 A1    Sep. 26, 2019

(30) Foreign Application Priority Data

May 17, 2016  (CN) .......................... 201610329012.8

(51) Int. Cl.
*A61K 31/426* (2006.01)
*A61P 1/04* (2006.01)

(52) U.S. Cl.
CPC .............. *A61K 31/426* (2013.01); *A61P 1/04* (2018.01)

(58) Field of Classification Search
CPC ................................ A61K 31/426; A61P 1/04
See application file for complete search history.

(56) References Cited

U.S. PATENT DOCUMENTS 4,319,026 A   3/1982  Hedrich et al.
10,919,869 B2 * 2/2021  Li ........................ C07D 277/50

OTHER PUBLICATIONS

Fitzpatrick et al. (Inflammatory Bowel Diseases, vol. 16, Issue 10, Oct. 1, 2010, pp. 1763-1777 (Year: 2010).*
English Translation of the International Search Report corresponding to PCT/CN2017/084749 dated Aug. 18, 2017, 3 pages.
Li, Shiliang et al., "Rational Design of Benzylidenehydrazinyl-Substituted Thiazole Derivatives as Potent Inhibitors of human Dihydroorotate Dehydrogenease with in Vivo Anti-arthritic Activity," *Scientific Reports* (Oct. 7, 2015); 5(14836):1-19.
Choi, Paul M. et al., "Immunomodulator Therapy in Inflammatory Bowel Disease," *Digestive Diseases and Sciences* (Sep. 1994; accepted Feb. 4, 1994) 39(9):1885-1892.
Herrlinger, K. R. et al., "Efficacy, safety and tolerability of vidofludimus in patients with inflammatory bowel disease: The Entrance study," *Journal of Crohn's and Colitis* (2013) 7:636-643.
Lolli, Marco L. et al., "Use of human Dihydroorotate Dehydrogenase (hDHODH) Inhibitors in Autoimmune Diseases and New Perspectives in Cancer Therapy," *Recent Patents on Anti-Cancer Drug Discovery* (2018; accepted Oct. 26, 2017) 13:86-105.

* cited by examiner

*Primary Examiner* — James D. Anderson
*Assistant Examiner* — William Y Lee
(74) *Attorney, Agent, or Firm* — Mintz Levin Cohn Ferris Glovsky and Popeo, P.C.

(57) ABSTRACT

The present invention relates to applications of a novel thiazole derivative in treating ulcerative colitis and in the preparation of drugs for treating ulcerative colitis. The present invention specifically relates to applications of a compound represented by formula I and a pharmaceutical composition containing the compound represented by formula I, in treating ulcerative colitis and in the preparation of drugs for treating ulcerative colitis:

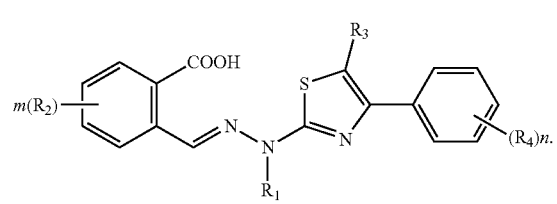

4 Claims, 2 Drawing Sheets

APPLICATIONS OF NOVEL THIAZOLE DERIVATIVE IN TREATING INFLAMMATORY BOWEL DISEASES

TECHNICAL FIELD

The present invention relates to the field of medicinal chemistry. In particular, the present invention relates to uses of novel thiazole derivatives for the preparation of a medicament for treating ulcerative colitis and for treating inflammatory bowel disease, in particular ulcerative colitis.

BACKGROUND

Ulcerative colitis (UC), also known as chronic non-specific ulcerative colitis, is a chronic inflammation and ulcerative lesion of the intestinal mucosa with unclear cause, which mainly influences the rectal mucosa, sigmoid mucosa, or reversely influence the left colon, right colon, and even the entire colon and terminal ileum, and is called inflammatory bowel disease (IBD) together with Crohn disease (CD). Its clinical manifestations are mainly diarrhea, mucus pus and bloody stools, abdominal pain. The severity of the disease varies, and it is often a chronic course of recurrent episodes. The disease can occur at any age, more common in 20-40 years old, and can also be seen in children or old age. There was no significant difference in the incidence of men and women. Pathological features of the disease are diffuse inflammation of the mucosa, infiltration of inflammatory cells such as diffuse lymphocytes, plasma cells, and monocytes in the intrinsic membrane. During the active phase, there are a large number of neutrophils and eosinophil infiltration, and cryptitis and crypt abscess will be incurred. As early as the last century, clinicians have an understanding of ulcerative colitis. Most scholars believe that ulcerative colitis is caused by multi-factor interactions, including infection, immunity, genetics, environment and psychology. However, till now, the specific pathogenic factors and pathogenesis of the disease have not been clarified. There has been no significant progress in the treatment for many years, and the efficacy is not satisfactory.

At present, there are few drugs for ulcerative colitis, mainly aminosalicylic acid, sulfasalazine, oxarazin, mesalazine, immunosuppressive agents and hormonal drugs. These drugs exhibit certain therapeutic effects, however, serious side effects are also produced. Therefore, ulcerative colitis is considered to be a disease that seriously affects people's quality of life and is extremely difficult to be cured, and the development of special drugs attracts attention from pharmaceutical companies worldwide.

Therefore, there is an urgent need in the art to find new, more effective, safer drugs with pharmacological properties for treating ulcerative colitis.

SUMMARY OF THE INVENTION

It is an object of the present invention to provide a novel, more efficient and safer compound with inhibitory activities on inflammatory bowel disease, especially ulcerative colitis, so as to be used as a therapeutic drug for ulcerative colitis.

In a first aspect, use of a compound of formula I or a pharmaceutically acceptable salt or ester thereof for preparing a medicament for the treatment of inflammatory bowel disease is provided in the invention:

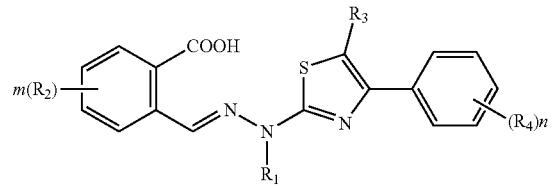

wherein, $R_1$ is selected from the group consisting of H, a substituted or unsubstituted $C_1$-$C_6$ alkyl and C3-C6 cycloalkyl;

$R_2$ is independently selected from the group consisting of H, halogen, a substituted or unsubstituted C1-C6 alkyl, substituted or unsubstituted C1-C6 alkoxy, CN, $NO_2$, hydroxy and $NR^aR^b$;

$R^a$, $R^b$ are independently selected from H or C1-C6 alkyl;

$R_3$ is selected from the group consisting of H and a substituted or unsubstituted C1-C6 alkyl;

$R_4$ is selected from the group consisting of H and halogen;

m is an integer from 0 to 4;

n is an integer from 0 to 5.

In a specific embodiment, the inflammatory bowel disease is ulcerative colitis or Crohn's disease; preferably ulcerative colitis.

In a specific embodiment, in Formula I, $R_1$ is selected from the group consisting of H and a substituted or unsubstituted C1-C6 alkyl; $R_2$ is selected from the group consisting of H, halogen, a substituted or unsubstituted C1-C6 alkyl and substituted or unsubstituted C1-C6 alkoxy; $R_3$ is selected from the group consisting of H and a substituted or unsubstituted C1-C6 alkyl; $R_4$ is selected from the group consisting of H and halogen; m is an integer from 0 to 2; and n is an integer from 0 to 2.

In a specific embodiment, the compound is shown in Formula II:

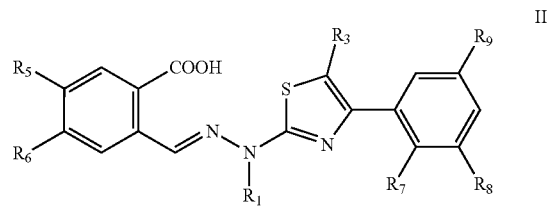

Wherein, $R_1$ is selected from the group consisting of H and a substituted or unsubstituted $C_1$-$C_3$ alkyl;

$R_5$ and $R_6$ are independently selected from the group consisting of H, halogen and a substituted or unsubstituted C1-C3 alkyl;

$R_3$ is selected from the group consisting of H and a substituted or unsubstituted $C_1$-$C_3$ alkyl; and $R_7$, $R_8$ and $R_9$ are independently selected from the group consisting of H and halogen.

In a specific embodiment, the compound of formula I or a pharmaceutically acceptable salt or ester thereof is selected from the following group:

| No. | Structure |
|---|---|
| 1 | 2-[(E)-{2-methyl-2-[4-(2-chlorophenyl)thiazol-2-yl]hydrazinylidene}methyl]benzoic acid |
| 2 | 2-[(E)-{2-ethyl-2-[4-(2-chlorophenyl)thiazol-2-yl]hydrazinylidene}methyl]benzoic acid |
| 3 | 2-[(E)-{2-propyl-2-[4-(2-chlorophenyl)thiazol-2-yl]hydrazinylidene}methyl]benzoic acid |
| 4 | 2-[(E)-{2-isopropyl-2-[4-(2-chlorophenyl)thiazol-2-yl]hydrazinylidene}methyl]benzoic acid |
| 5 | 2-[(E)-{2-(sec-butyl)-2-[4-(2-chlorophenyl)thiazol-2-yl]hydrazinylidene}methyl]benzoic acid |
| 6 | 2-[(E)-{2-(pentan-2-yl)-2-[4-(2-chlorophenyl)thiazol-2-yl]hydrazinylidene}methyl]benzoic acid |
| 7 | 2-[(E)-{2-(2-hydroxyethyl)-2-[4-(2-chlorophenyl)thiazol-2-yl]hydrazinylidene}methyl]benzoic acid |
| 8 | 2-[(E)-{2-methyl-2-[4-(2-chlorophenyl)thiazol-2-yl]hydrazinylidene}methyl]-5-(trifluoromethyl)benzoic acid |
| 8-1 | 2-[(E)-{2-[4-(2-chlorophenyl)thiazol-2-yl]hydrazinylidene}methyl]-5-(trifluoromethyl)benzoic acid |
| 9 | 2-[(E)-{2-methyl-2-[4-(2-chlorophenyl)thiazol-2-yl]hydrazinylidene}methyl]-4-methylbenzoic acid |
| 9-1 | 2-[(E)-{2-[4-(2-chlorophenyl)thiazol-2-yl]hydrazinylidene}methyl]-4-methylbenzoic acid |
| 10 | 2-[(E)-{2-methyl-2-[4-(2-chlorophenyl)thiazol-2-yl]hydrazinylidene}methyl]-4-fluorobenzoic acid |
| 10-1 | 2-[(E)-{2-[4-(2-chlorophenyl)thiazol-2-yl]hydrazinylidene}methyl]-4-fluorobenzoic acid |
| 11 | 2-[(E)-{2-methyl-2-(5-methyl-4-phenylthiazol-2-yl)hydrazinylidene}methyl]-4-methylbenzoic acid |
| 12 | 2-[(E)-{2-methyl-2-(5-methyl-4-phenylthiazol-2-yl)hydrazinylidene}methyl]benzoic acid |
| 12-1 | 2-[(E)-{2-(5-methyl-4-phenylthiazol-2-yl)hydrazinylidene}methyl]benzoic acid |
| 13 | 2-[(E)-{2-methyl-2-[5-methyl-4-(2-chlorophenyl)thiazol-2-yl]hydrazinylidene}methyl]benzoic acid |
| 14 | 2-[(E)-{2-[5-ethyl-4-(2-chlorophenyl)thiazol-2-yl]hydrazinylidene}methyl]benzoic acid |

Note: The compound names above are inferred; the page shows structural drawings only, labeled by number.

-continued

| No. | Structure |
|---|---|
| 15 | 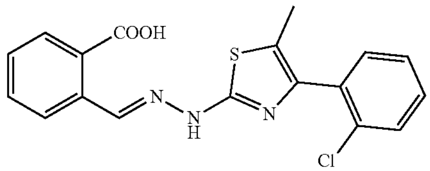 [SMILES: Cc1sc(N/N=C/c2ccccc2C(=O)O)nc1-c1ccccc1Cl] |
| 16 | 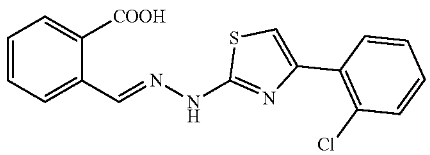 [SMILES: O=C(O)c1ccccc1/C=N/Nc1nc(-c2ccccc2Cl)cs1] |
| 17 | 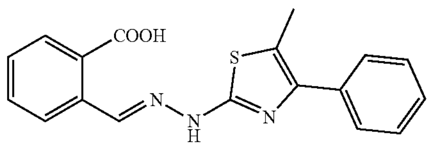 [SMILES: Cc1sc(N/N=C/c2ccccc2C(=O)O)nc1-c1ccccc1] |
| 18 | 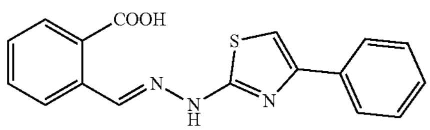 [SMILES: O=C(O)c1ccccc1/C=N/Nc1nc(-c2ccccc2)cs1] |
| 19 | 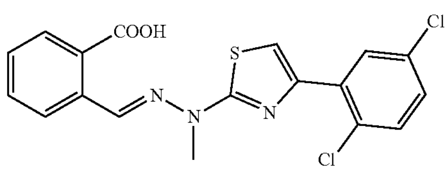 [SMILES: CN(/N=C/c1ccccc1C(=O)O)c1nc(-c2cc(Cl)ccc2Cl)cs1] |
| 20 | 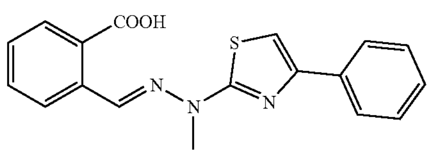 [SMILES: CN(/N=C/c1ccccc1C(=O)O)c1nc(-c2ccccc2)cs1] |
| 21 | 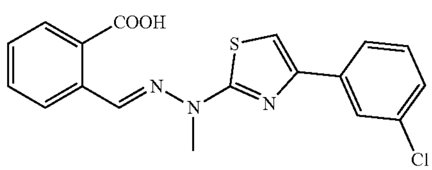 [SMILES: CN(/N=C/c1ccccc1C(=O)O)c1nc(-c2cccc(Cl)c2)cs1] |
| 22 | 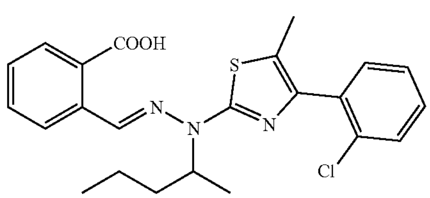 [SMILES: CCCC(C)N(/N=C/c1ccccc1C(=O)O)c1nc(-c2ccccc2Cl)c(C)s1] |
| 23 | 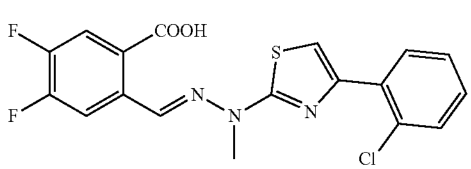 [SMILES: CN(/N=C/c1cc(F)c(F)cc1C(=O)O)c1nc(-c2ccccc2Cl)cs1] |

-continued

| No. | Structure |
|---|---|
| 23-1 | 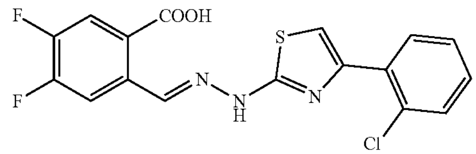 [SMILES: O=C(O)c1cc(F)c(F)cc1/C=N/Nc1nc(-c2ccccc2Cl)cs1] |
| 24 | 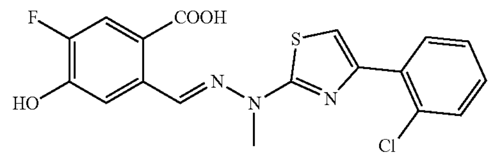 [SMILES: CN(/N=C/c1cc(O)c(F)cc1C(=O)O)c1nc(-c2ccccc2Cl)cs1] |
| 25 | 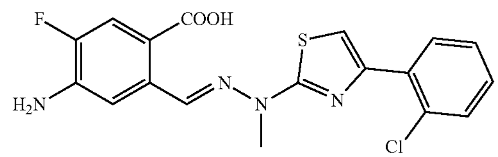 [SMILES: CN(/N=C/c1cc(N)c(F)cc1C(=O)O)c1nc(-c2ccccc2Cl)cs1] |
| 52 | 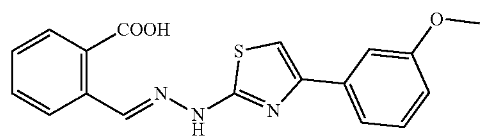 [SMILES: COc1cccc(-c2csc(N/N=C/c3ccccc3C(=O)O)n2)c1] |
| 53 | 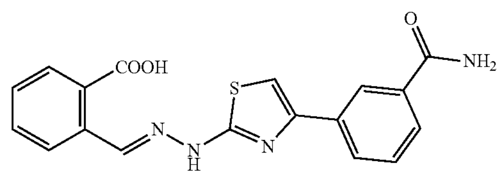 [SMILES: NC(=O)c1cccc(-c2csc(N/N=C/c3ccccc3C(=O)O)n2)c1] |
| 54 | 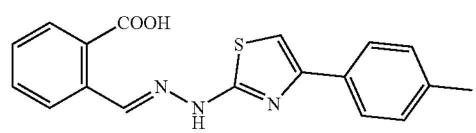 [SMILES: Cc1ccc(-c2csc(N/N=C/c3ccccc3C(=O)O)n2)cc1] |
| 55 | 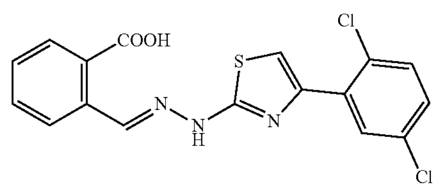 [SMILES: O=C(O)c1ccccc1/C=N/Nc1nc(-c2cc(Cl)ccc2Cl)cs1] |
| 56 | 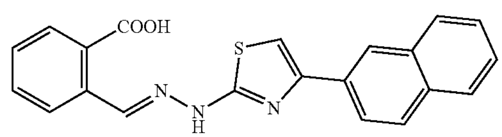 [SMILES: O=C(O)c1ccccc1/C=N/Nc1nc(-c2ccc3ccccc3c2)cs1] |
| 57 | 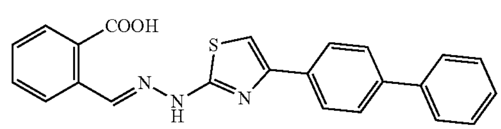 [SMILES: O=C(O)c1ccccc1/C=N/Nc1nc(-c2ccc(-c3ccccc3)cc2)cs1] |
| 58 | 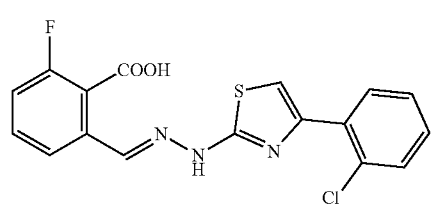 [SMILES: O=C(O)c1c(F)cccc1/C=N/Nc1nc(-c2ccccc2Cl)cs1] |

| No. | Structure |
|---|---|
| 59 | 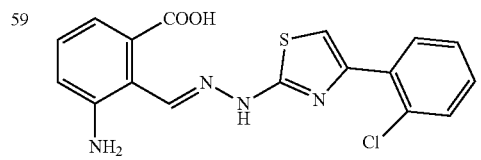 |
| A1 | 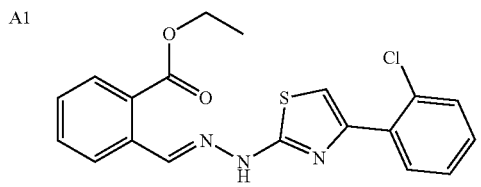 |
| A2 | 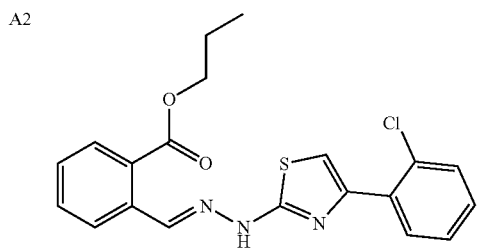 |
| A3 | 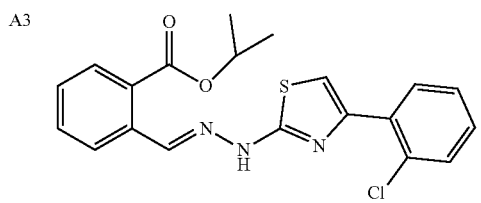 |
| A4 | 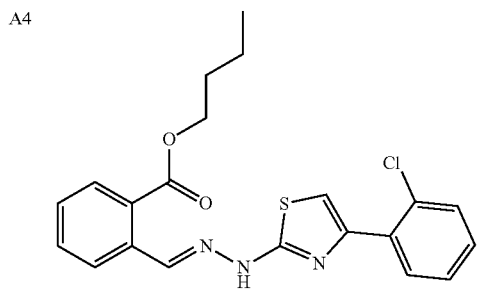 |
| A5 | 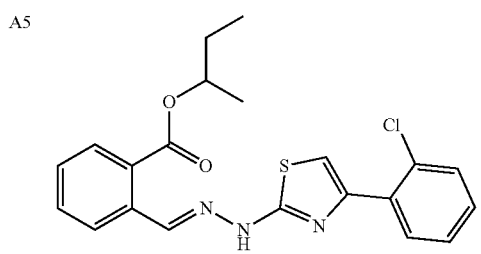 |
| No. | Structure |
|---|---|
| A6 | 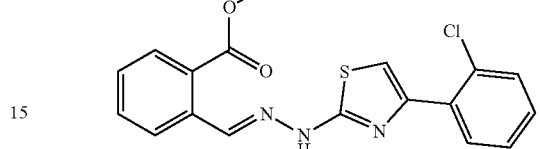 |
| A7 | 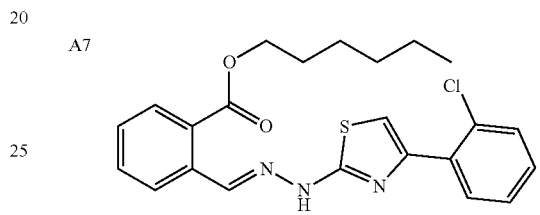 |
| A8 | 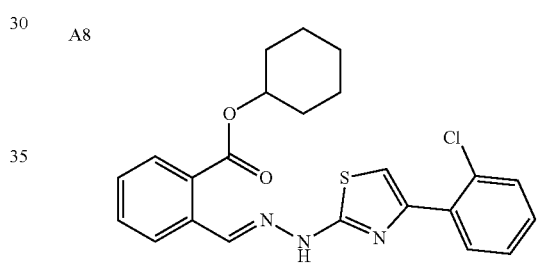 |
| A9 | 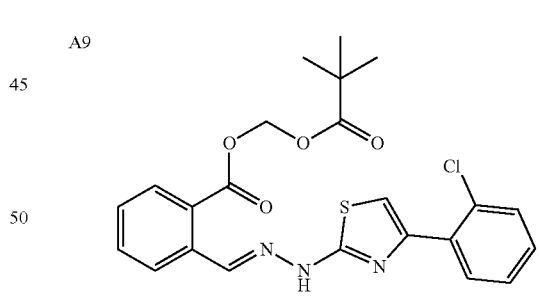 |
| A10 | 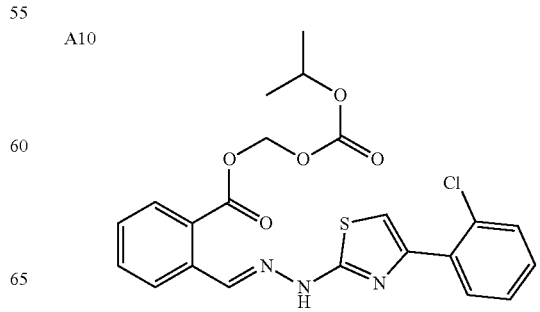 |

| No. | Structure |
|---|---|
| A11 | 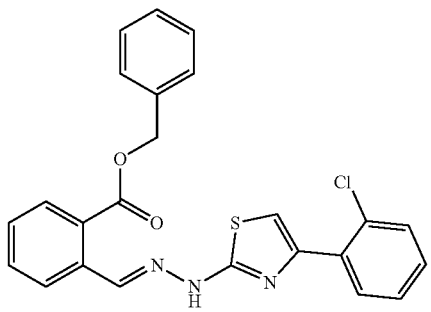 [SMILES: O=C(OCc1ccccc1)c1ccccc1/C=N/Nc1nc(-c2ccccc2Cl)cs1] |
| A12 | 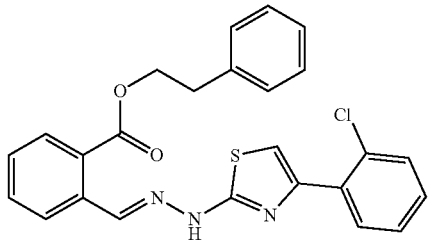 [SMILES: O=C(OCCc1ccccc1)c1ccccc1/C=N/Nc1nc(-c2ccccc2Cl)cs1] |
| A13 | 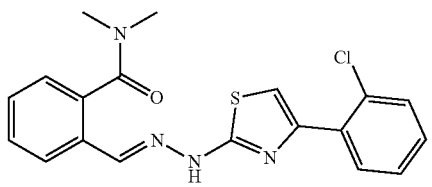 [SMILES: CN(C)C(=O)c1ccccc1/C=N/Nc1nc(-c2ccccc2Cl)cs1] |
| B1 | 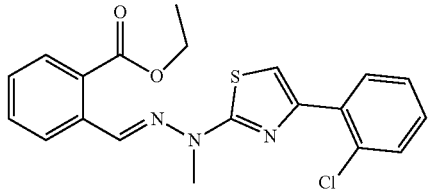 [SMILES: CCOC(=O)c1ccccc1/C=N/N(C)c1nc(-c2ccccc2Cl)cs1] |
| B2 | 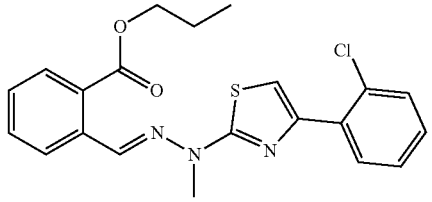 [SMILES: CCCOC(=O)c1ccccc1/C=N/N(C)c1nc(-c2ccccc2Cl)cs1] |
| B3 | 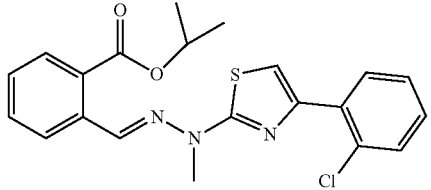 [SMILES: CC(C)OC(=O)c1ccccc1/C=N/N(C)c1nc(-c2ccccc2Cl)cs1] |
| B4 | 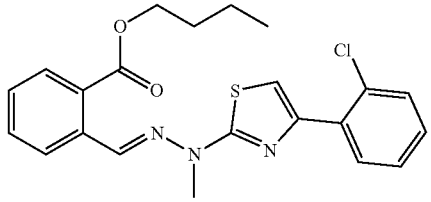 [SMILES: CCCCOC(=O)c1ccccc1/C=N/N(C)c1nc(-c2ccccc2Cl)cs1] |
| B5 | 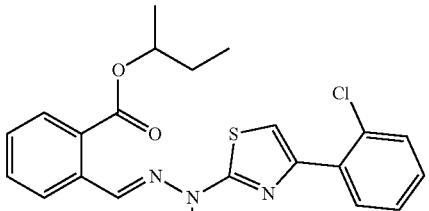 |
| B6 | 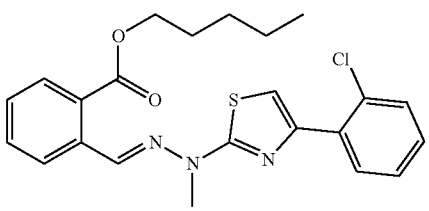 [SMILES: CCCCCOC(=O)c1ccccc1/C=N/N(C)c1nc(-c2ccccc2Cl)cs1] |
| B7 | 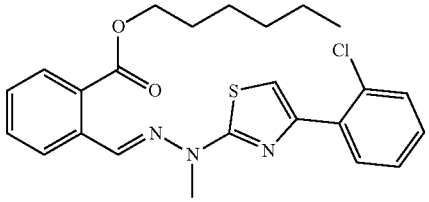 [SMILES: CCCCCCOC(=O)c1ccccc1/C=N/N(C)c1nc(-c2ccccc2Cl)cs1] |
| B8 | 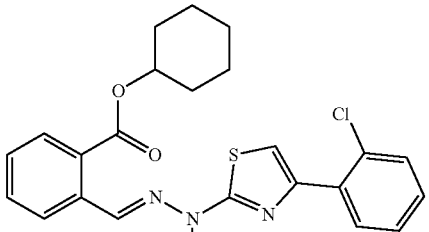 |
| B9 | 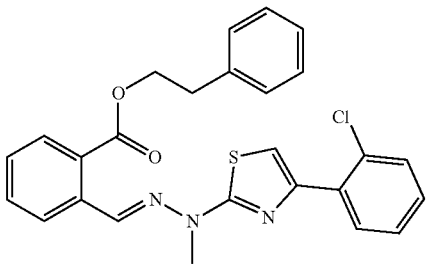 [SMILES: CN(/N=C/c1ccccc1C(=O)OCCc1ccccc1)c1nc(-c2ccccc2Cl)cs1] |
| B10 | 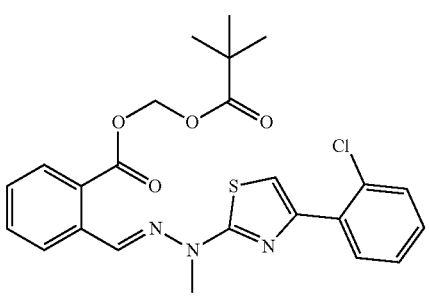 [SMILES: CN(/N=C/c1ccccc1C(=O)OCOC(=O)C(C)(C)C)c1nc(-c2ccccc2Cl)cs1] |

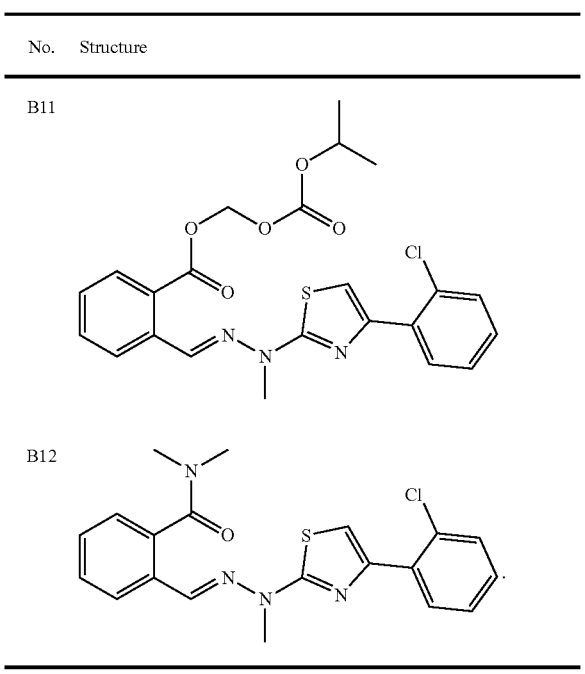
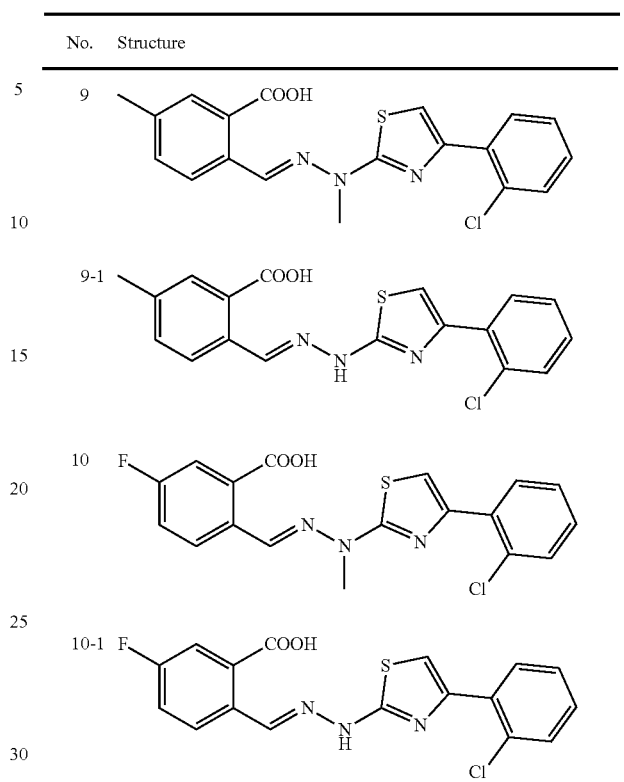
In a specific embodiment, the compound is selected from the following group:
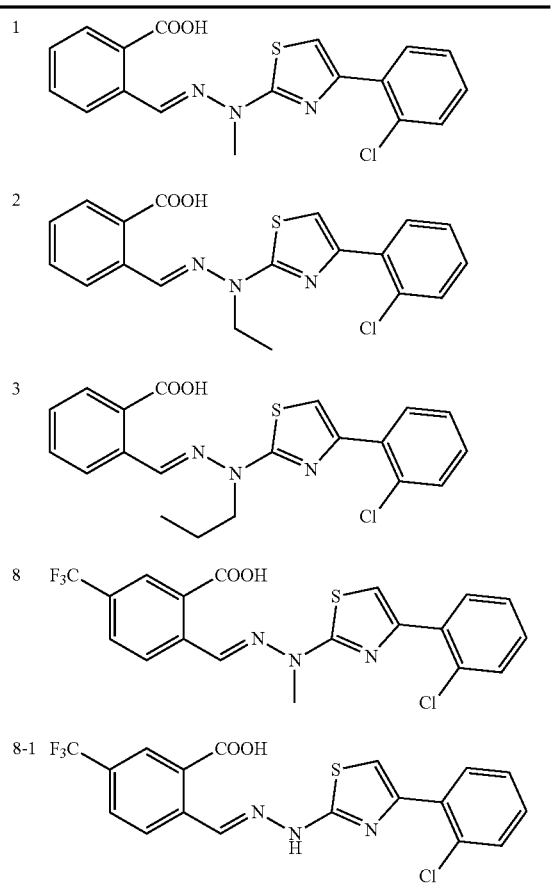

-continued

| No. | Structure |
|---|---|
| 20 | (2-COOH phenyl)-CH=N-N(CH3)-[4-phenyl-thiazol-2-yl] |
| 21 | (2-COOH phenyl)-CH=N-N(CH3)-[4-(2-chlorophenyl)-thiazol-2-yl] |
| 23 | (4,5-difluoro-2-COOH phenyl)-CH=N-N(CH3)-[4-(2-chlorophenyl)-thiazol-2-yl] |
| 23-1 | (4,5-difluoro-2-COOH phenyl)-CH=N-NH-[4-(2-chlorophenyl)-thiazol-2-yl] |
| 55 | (2-COOH phenyl)-CH=N-NH-[4-(2,5-dichlorophenyl)-thiazol-2-yl] |
| 58 | (3-fluoro-2-COOH phenyl)-CH=N-NH-[4-(2-chlorophenyl)-thiazol-2-yl] |

In a specific embodiment, the compound is selected from the following group:

| No. | Structure |
|---|---|
| 1 | (2-COOH phenyl)-CH=N-N(CH3)-[4-(2-chlorophenyl)-thiazol-2-yl] |
| 2 | (2-COOH phenyl)-CH=N-N(C2H5)-[4-(2-chlorophenyl)-thiazol-2-yl] |
| 8 | (4-CF3-2-COOH phenyl)-CH=N-N(CH3)-[4-(2-chlorophenyl)-thiazol-2-yl] |
| 8-1 | (4-CF3-2-COOH phenyl)-CH=N-NH-[4-(2-chlorophenyl)-thiazol-2-yl] |
| 9 | (5-methyl-2-COOH phenyl)-CH=N-N(CH3)-[4-(2-chlorophenyl)-thiazol-2-yl] |
| 9-1 | (5-methyl-2-COOH phenyl)-CH=N-NH-[4-(2-chlorophenyl)-thiazol-2-yl] |
| 10 | (4-fluoro-2-COOH phenyl)-CH=N-N(CH3)-[4-(2-chlorophenyl)-thiazol-2-yl] |
| 10-1 | (4-fluoro-2-COOH phenyl)-CH=N-NH-[4-(2-chlorophenyl)-thiazol-2-yl] |
| 12 | (2-COOH phenyl)-CH=N-N(CH3)-[5-methyl-4-phenyl-thiazol-2-yl] |
| 12-1 | (2-COOH phenyl)-CH=N-NH-[5-methyl-4-phenyl-thiazol-2-yl] |
| 15 | (2-COOH phenyl)-CH=N-NH-[5-methyl-4-(2-chlorophenyl)-thiazol-2-yl] |

-continued

| No. | Structure |
|---|---|
| 16 | 2-COOH-phenyl-CH=N-NH-(thiazole with S, N)-4-(2-Cl-phenyl) |
| 17 | 2-COOH-phenyl-CH=N-NH-(4-methyl-thiazole)-5-phenyl |
| 23 | 4,5-diF-2-COOH-phenyl-CH=N-N(CH₃)-(thiazole)-4-(2-Cl-phenyl) |
| 23-1 | 4,5-diF-2-COOH-phenyl-CH=N-NH-(thiazole)-4-(2-Cl-phenyl) |

In a second aspect, use of a pharmaceutical composition for preparing a medicament for the treatment of inflammatory bowel disease is provided in the present invention, wherein the pharmaceutical composition comprises a compound or a pharmaceutically acceptable salt or ester thereof of the first aspect of the present invention, and a pharmaceutically acceptable carrier or excipient.

In a preferred embodiment, the inflammatory bowel disease includes, but not limited to, ulcerative colitis or Crohn's disease; preferably ulcerative colitis.

In a third aspect, a pharmaceutical composition is provided in the present invention, wherein the pharmaceutical composition is used for treating inflammatory bowel disease and comprises the compound or a pharmaceutically acceptable salt or ester thereof of the first aspect of the present invention, and a pharmaceutically acceptable carrier or excipient.

In a preferred embodiment, the inflammatory bowel disease includes, but not limited to, ulcerative colitis or Crohn's disease; preferably ulcerative colitis.

In a preferred embodiment, the pharmaceutical composition is a dosage form suitable for oral administration, including but not limited to a tablet, solution, suspension, capsule, granule, powder.

In a fourth aspect, a method for treating inflammatory bowel disease is provided in the present invention, comprising administrating the compound of the first aspect of the present invention or and the pharmaceutical composition of the third aspect of the present invention to a subject in need thereof.

In a preferred embodiment, the inflammatory bowel disease includes, but not limited to, ulcerative colitis or Crohn's disease; preferably ulcerative colitis.

It is to be understood that, within the scope of the present invention, various technical features of the present invention and the technical features specifically described hereinafter (as in the Examples) may be combined with each other to constitute new or preferred technical solutions, which will not described one by one herein.

MODES FOR CARRYING OUT THE INVENTION

Figure 1:
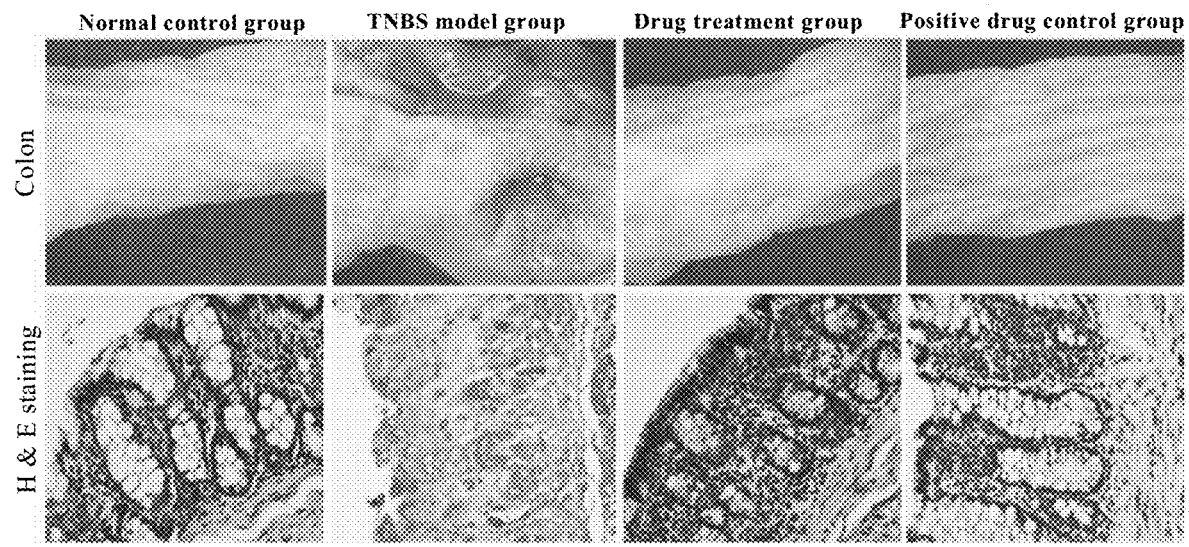
FIG. 1 shows the general morphological damage of colon and pathological observations of colon tissue in the normal control group, model group, drug treatment group and positive control group (effects of compound 1).
Figure 2:
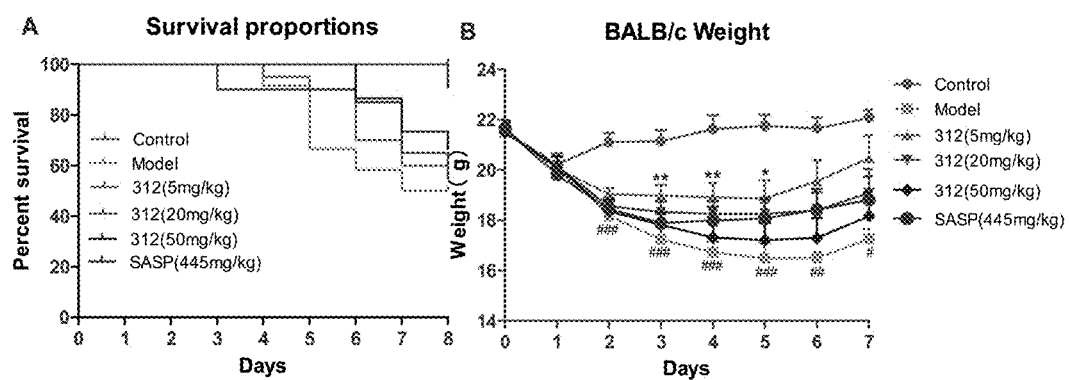
FIG. 2 shows effects of Compound 16 (312 in the figure) on the general condition of TNBS-mediated UC model mice (for BALB/c mice, mice were weighed daily during treatment, and data are expressed as mean±SEM, # $P<0.05$, ## $P<0.01$, ### $P<0.001$, compared with the normal control group. * $P<0.05$, ** P<, compared with the model group.) (stool of mice in normal control group was observed, and there were no abnormalities such as diarrhea or blood in stool; the stool characteristics of mice modeled by TNBS enema showed different degrees of changes: such as loose stools or bloody stools. From the 3rd day of the experiment, the BALB/c mice in each group, except the normal control group died continuously, and the situations of diarrhea and death in the model group were the most severe. On the $8^{th}$ day of the experiment, the mortality rate was about 50%. The diarrhea of the mice in the control group administered with sulfasalazine was mild, only one mouse died on the $8^{th}$ day of the experiment. The diarrhea of the mice in three different dosage groups of Compound 16 was relieved compared with the model group).
Figure 3:
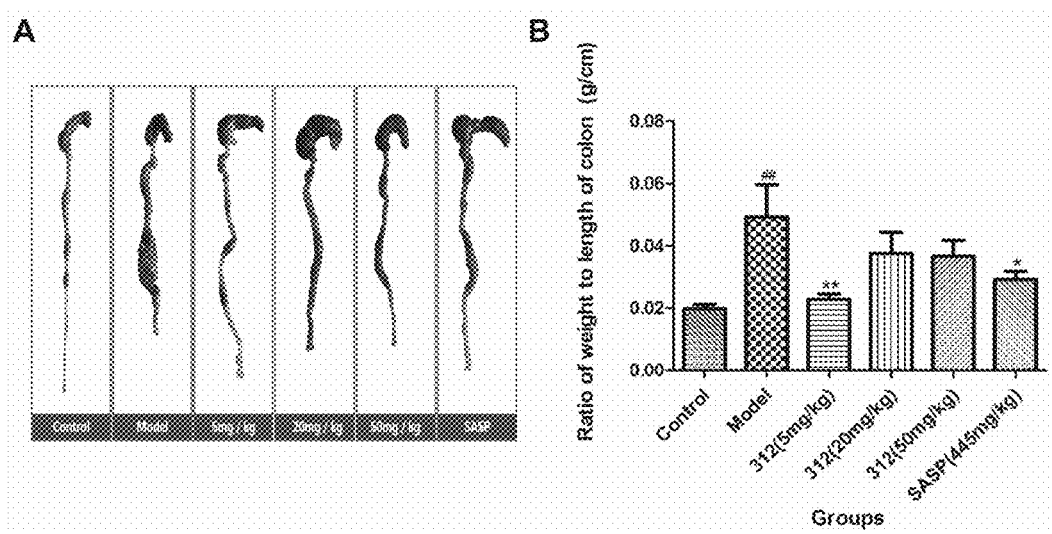
FIG. 3 shows effects of Compound 16 (312 in the figure) on colon mass in TNBS-mediated UC model mice. Panel A shows representative colon photographs from different experimental groups. Panel B shows the ratio of colon weight to length in each experimental group. #$p<0.05$, compared with the control group. *$p<0.05$, **$p<0.01$, compared with the model group. As can be seen from the figure, after the establishment of the UC model, the mice in the model group developed severe lesions in the colon. Different dosages of compound 312 (5 mg/kg, 20 mg/kg, 50 mg/kg) and positive drugs can improve the extent of ulcer lesions of colon and visceral adhesions. And 312 of 5 mg/kg had the best effect on colonic lesions.
Figure 4:
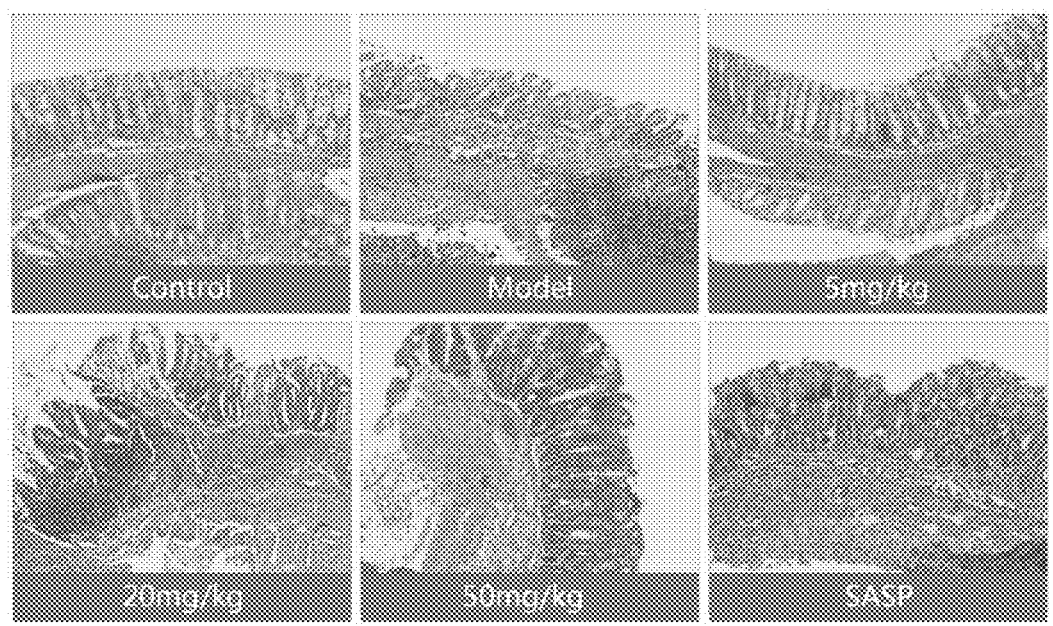
FIG. 4 shows effects of Compound 16 (312 in the figure) on histopathology of colon in TNBS-induced UC model mice. Representative photographs of HE staining of colon tissue sections are shown with a magnification of 40. The results showed that the colon tissue of the normal control group exhibited a complete structure. After the UC model was established, the integrity of colon tissue of the mice in the model group was severely damaged and local erosion occurred. After the administration of the positive drug SASP, the above lesions were largely reversed; after treatment with Compound 16, the mucosal integrity was improved to a greater extent, compared with the model group, effects produced from the administration of Compound 16 at 5 mg/kg and 50 mg/kg were more effective than those at 20 mg/kg, and the effects produced from low dosage of 5 mg/kg were similar to those of positive drug.

After extensive and intensive research, the inventors unexpectedly discovered a series of thiazole derivatives with better therapeutic effects on ulcerative colitis, and their structural skeletons are completely different from therapeutic drugs for ulcerative colitis reported in the literature (e.g., aminosalicylic acid, sulfasalazine, Ossalin, mesalazine). These compounds show significant therapeutic activities against ulcerative colitis through validation by laboratory animals. The present invention has been completed based the above discoveries.

Definition of Terms

Some groups mentioned herein are defined as follows:

As used herein, "alkyl" refers to a saturated branched or straight-chain alkyl in a carbon chain length of 1 to 10 carbon atoms, and a preferred alkyl includes an alkyl having from 2 to 8 carbon atoms, 1 to 6, 1 to 4 and 1-3 carbon atoms. Examples of alkyl include, but are not limited to, methyl, ethyl, n-propyl, isopropyl, n-butyl, isobutyl, heptyl and the like. The alkyl may be substituted by one or more substituents, for example halogen or haloalkyl. For example, the alkyl may be an alkyl substituted with 1 to 4 fluorine atoms, such as triflurormethyl, or the alkyl may be an alkyl substituted with a fluoroalkyl.

As used herein, "cycloalkyl" means a saturated alkyl with alicyclic structure, for example, a C3-C6 cycloalkyl. In a specific embodiment, the cycloalkyl includes, but is not limited to, cyclopropyl, cyclobutyl, cyclopentyl or cyclohexyl. The cycloalkyl described herein may be substituted or unsubstituted, including but not limited to, substituted with one or more halogen atoms, such as fluorine atoms.

As used herein, "amino" refers to a group of the formula "$NR_xR_y$", wherein $R_x$ and $R_y$ may be independently selected from H or a $C_1$-$C_3$ alkyl or $C_1$-$C_3$ haloalkyl. In a specific embodiment, "amino" as used herein refers to $NH_2$.

As used herein, "halogen" refers to fluoro, chloro, bromo and iodo. In a preferred embodiment, the halogen is chlorine or fluorine; more preferably fluorine.

Compounds of the Invention

The inventors unexpectedly discovered a series of thiazole derivatives which possess novel structural skeletons and better therapeutic effects on inflammatory bowel disease, especially ulcerative colitis. These compounds show significant therapeutic activities against ulcerative colitis in animal experiments.

In a specific embodiment, the compound of the invention is a compound of formula I or a pharmaceutically acceptable salt or ester thereof:

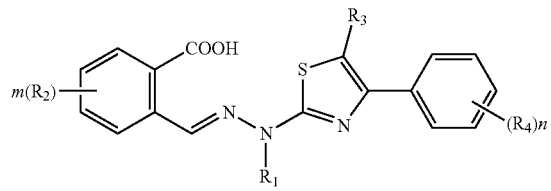

I

Wherein, $R_1$ is selected from the group consisting of H, a substituted or unsubstituted C1-C6 alkyl and C3-C6 cycloalkyl;

$R_2$ is selected from the group consisting of H, halogen, a substituted or unsubstituted C1-C6 alkyl, substituted or unsubstituted C1-C6 alkoxy, CN, $NO_2$, hydroxyl and $NR^aR^b$;

$R^a$, $R^b$ are independently selected from H or C1-C6 alkyl;

$R_3$ is selected from the group consisting of H and a substituted or unsubstituted C1-C6 alkyl;

$R_4$ is selected from H or halogen;

m is an integer from 0-4;

n is an integer from 0 to 5.

In a preferred embodiment, $R_1$ is selected from the group consisting of H and a substituted or unsubstituted C1-C6 alkyl; $R_2$ is selected from the group consisting of H, halogen (preferably, F), a substituted (preferably F-substituted) or unsubstituted C1-C6 alkyl (preferably C1-C3 alkyl) and substituted or unsubstituted C1-C6 alkoxy; $R_3$ is selected from the group consisting of H and a substituted or unsubstituted C1-C6 alkyl (preferably C1-C3 alkyl); $R_4$ is selected from the group consisting of H and halogen (preferably, Cl); m is an integer from 0 to 2; and n is an integer from 0 to 2.

In a further preferred embodiment, the compound is shown in Formula II:

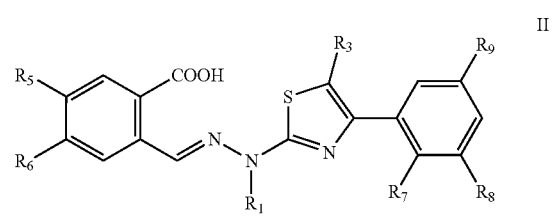

II

Wherein, $R_1$ is selected from the group consisting of H and a substituted or unsubstituted $C_1$-$C_3$ alkyl;

$R_5$ and $R_6$ are independently selected from the group consisting of H, halogen and a substituted (preferably F-substituted) or unsubstituted C1-C3 alkyl (preferably, methyl);

$R_3$ is selected from the group consisting of H and a substituted or unsubstituted $C_1$-$C_3$ alkyl; and $R_7$, $R_8$ and $R_9$ are independently selected from the group consisting of H and halogen (preferably Cl).

A pharmaceutical composition comprising a therapeutically effective amount of a compound or a pharmaceutically acceptable salt or ester thereof of the present invention, and a pharmaceutically acceptable carrier or excipient, based on the above compounds, is further provided in the present invention.

Examples of the pharmaceutically acceptable salt of a compound of the invention include, but are not limited to, inorganic and organic acid salts such as hydrochloride, hydrobromide, sulfate, citrate, lactate, tartrate, maleate, fumarate, mandelate and oxalate; and inorganic and organic base salts formed with bases such as sodium hydroxide, tris(hydroxymethyl)aminomethane (TRIS, tromethamine) and N-methyl glucosamine.

A pharmaceutically acceptable ester of a compound of the invention is a compound wherein the carboxyl of the compound of formula I is esterified, including but not limited to: an ester formed from a substituted or unsubstituted C1-C10 alkyl or cycloalkyl,

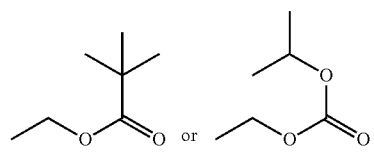

or with the compound of formula I, wherein "substituted" means that a group is substituted with a group selected from phenyl or halogen. Typically, a pharmaceutically acceptable ester of a compound of the invention is selected from the group consisting of:

| | |
|---|---|
| A1 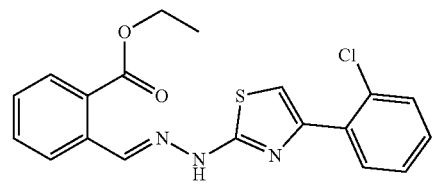 | A7 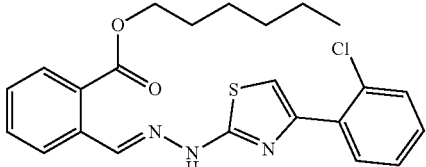 |
| A2 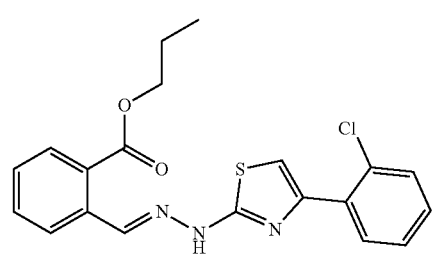 | A8 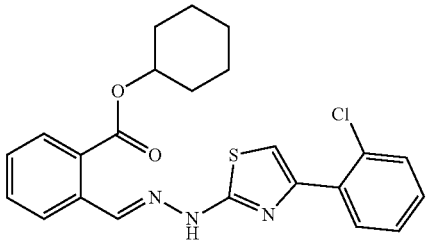 |
| A3 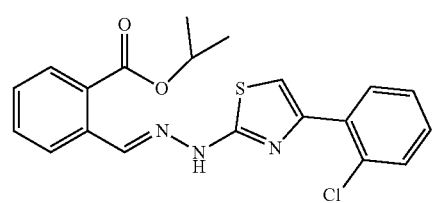 | A9 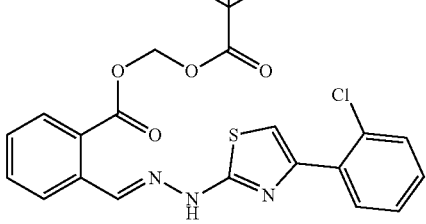 |
| A4 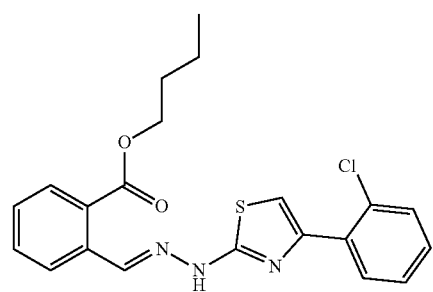 | A10 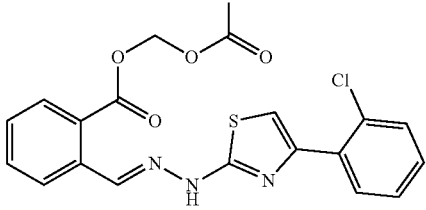 |
| A5 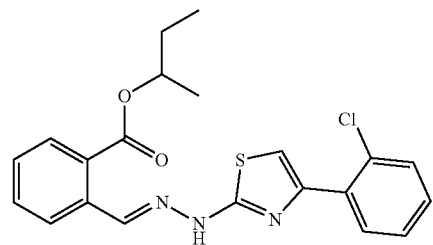 | A11 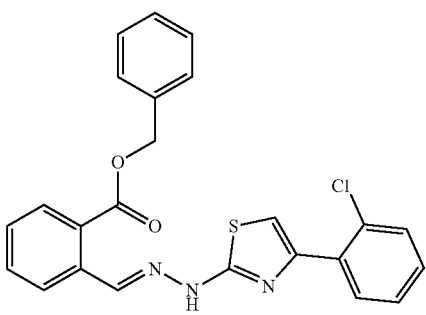 |
| A6 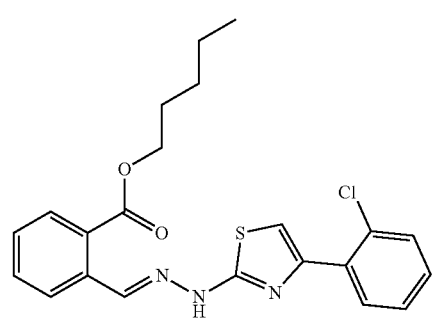 | A12 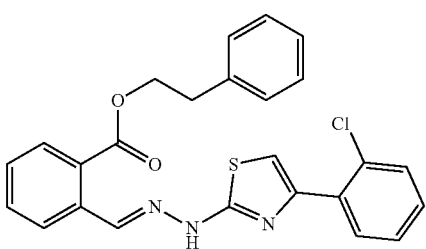 |

A13
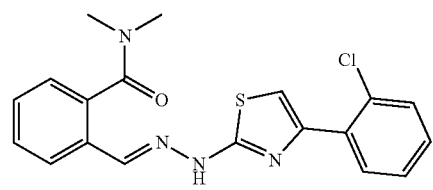 [SMILES: CN(C)C(=O)c1ccccc1/C=N/Nc1nc(-c2ccccc2Cl)cs1]
B1
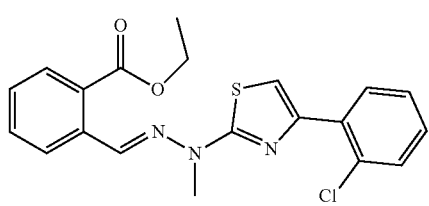 [SMILES: CCOC(=O)c1ccccc1/C=N/N(C)c1nc(-c2ccccc2Cl)cs1]
B2
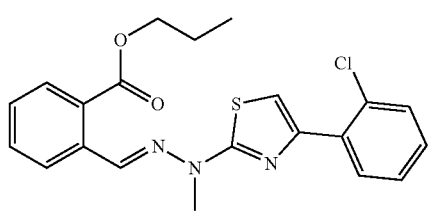 [SMILES: CCCOC(=O)c1ccccc1/C=N/N(C)c1nc(-c2ccccc2Cl)cs1]
B3
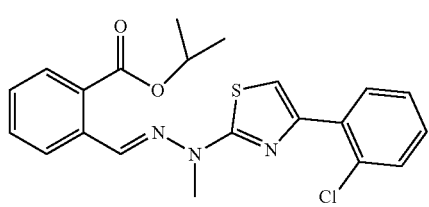 [SMILES: CC(C)OC(=O)c1ccccc1/C=N/N(C)c1nc(-c2ccccc2Cl)cs1]
B4
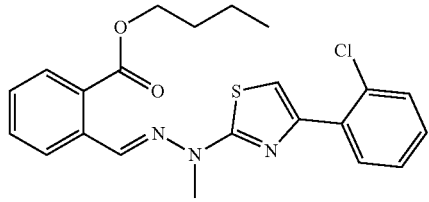 [SMILES: CCCCOC(=O)c1ccccc1/C=N/N(C)c1nc(-c2ccccc2Cl)cs1]
B5
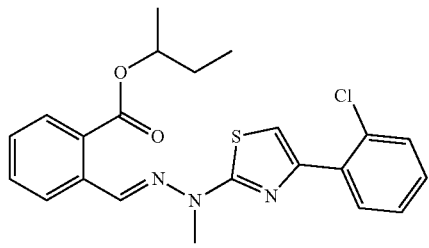 [SMILES: CCC(C)OC(=O)c1ccccc1/C=N/N(C)c1nc(-c2ccccc2Cl)cs1]
B6
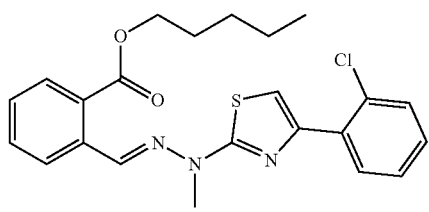
B7
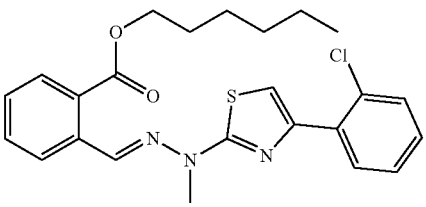 [SMILES: CCCCCCOC(=O)c1ccccc1/C=N/N(C)c1nc(-c2ccccc2Cl)cs1]
B8
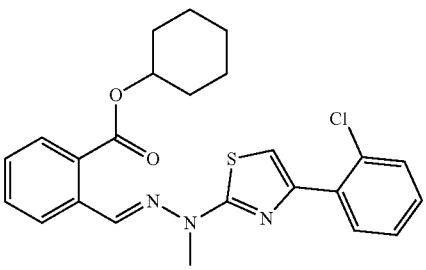 [SMILES: CN(/N=C/c1ccccc1C(=O)OC1CCCCC1)c1nc(-c2ccccc2Cl)cs1]
B9
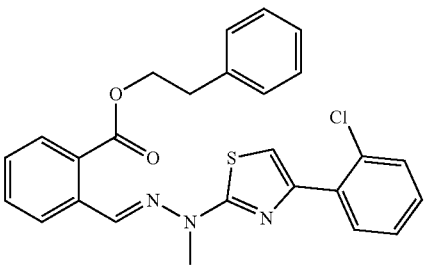 [SMILES: CN(/N=C/c1ccccc1C(=O)OCCc1ccccc1)c1nc(-c2ccccc2Cl)cs1]
B10
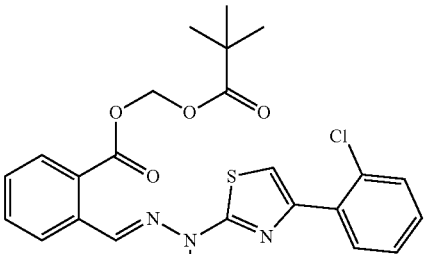
B11
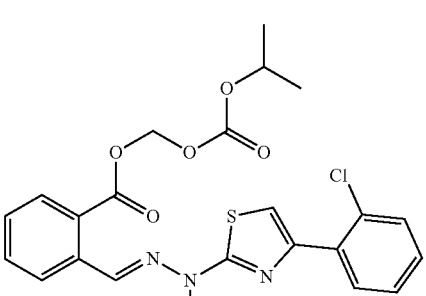
B12
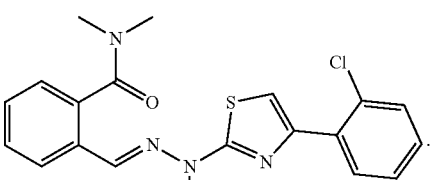
A skilled person in the art can determine the optimal dosage of each active ingredient in the pharmaceutical composition of the present invention, although the needs of each person vary. In general, the compound of the present invention or a pharmaceutically acceptable salt thereof is orally administered to a mammal in an amount of from about 0.0025 to 50 mg/kg body weight per day. However, it is preferably about 0.01 to 10 mg per kilogram for oral administration. For example, a unit oral dose can include from about 0.01 to 50 mg, preferably from about 0.1 to 10 mg, of a compound of the invention. The unit dose may be administered one or more times per day in one or more tablets, and each tablet contains from about 0.1 to 50 mg, preferably from about 0.25 to 10 mg of a compound of the invention or a solvate thereof.

The pharmaceutical composition of the present invention can be formulated into a dosage form suitable for various administration routes, including but not limited to, a dosage form suitable for parenteral, subcutaneous, intravenous, intramuscular, intraperitoneal, transdermal, oral, intrathecal, intracranial, intranasal or topical administration for treating tumors and other diseases. The administered amount is an amount effective to ameliorate or eliminate one or more conditions. For the treatment of a particular disease, an effective amount is a dosage sufficient to ameliorate or, in some way, alleviate symptoms associated with a disease. Such a dosage can be administered in a single dose or can be administered according to an effective therapeutic regimen. The administered amount may cure the disease, but usually is to improve symptoms of the disease. Repeated administrations are generally required to achieve the desired improvement in symptoms. The dosage of the drug will be determined according to the age, health and weight of a patient, the type of concurrent treatment, the frequency of treatment, and the desired therapeutic benefits.

The pharmaceutical preparation of the present invention can be administered to any mammal as long as they can obtain therapeutic effects of the compound of the present invention. The most important among these mammals is humans. The compounds of the invention or pharmaceutical compositions thereof are useful for treating ulcerative colitis.

The pharmaceutical preparations of the invention can be prepared in a known manner. For example, it is manufactured by a conventional mixing, granulating, tableting, dissolving, or freeze-drying process. When manufacturing oral formulations, the mixture can be selectively milled by combining solid auxiliary substances and the active compound. If necessary, after adding an appropriate amount of auxiliary substances, the mixture of granules is processed to obtain a tablet or tablet core.

Suitable auxiliary substances are, in particular, fillers, for example sugars, such as lactose or sucrose, mannitol or sorbitol; cellulose preparations or calcium phosphates, such as tricalcium phosphate or calcium hydrogen phosphate; and binders, such as starch pastes, including corn starch, wheat starch, rice starch, potato starch, gelatin, tragacanth, methyl cellulose, hydroxypropyl methyl cellulose, sodium carboxymethyl cellulose, or polyvinylpyrrolidone. If necessary, a disintegrating agent such as the above-mentioned starch, and carboxymethyl starch, crosslinked polyvinylpyrrolidone, agar, or alginic acid or a salt thereof such as sodium alginate may be added. Auxiliary substances can be, in particular, flow regulators and lubricants, for example, silica, talc, stearates such as calcium magnesium stearate, stearic acid or polyethylene glycol. If desired, the tablet core can be provided with a suitable coating that is resistant to gastric juice. For this purpose, a concentrated sugar solution can be applied. Such solutions may contain gum arabic, talc, polyvinylpyrrolidone, polyethylene glycol and/or titanium dioxide, lacquer solutions and suitable organic solvents or solvent mixtures. For preparing a gastric juice-resistant coating, a suitable cellulose solution such as cellulose acetate ortho-phthalate or hydroxypropyl methylcellulose ortho-phthalate can be used. A dye or pigment can be added to the coating of the tablet or tablet core for, for example, identification or for characterizing the combination of dosages of active ingredients.

Accordingly, a method for treating ulcerative colitis is also provided in the present invention, which comprises administering to a subject in need thereof a compound of the invention or a pharmaceutical composition comprising a compound of the invention.

Methods of administration include, but are not limited to, various methods of administration well known in the art, which can be determined based on the actual circumstances of a patient. The methods include, but are not limited to, parenteral, subcutaneous, intravenous, intramuscular, intraperitoneal, transdermal, buccal, intrathecal, intracranial, nasal or topical administration.

The invention also encompasses the use of a compound of the invention in the manufacture of a medicament for treating ulcerative colitis.

Further, a skilled person will, based on the common knowledge in the art and the contents of the present invention, appreciate that a compound of the present invention can form a salt or an ester due to the contained carboxyl, thereby forming a prodrug.

Advantages of the Invention

1. A series of structurally novel thiazole derivatives with better therapeutic effects on ulcerative colitis are firstly discovered in the present invention;

2. The compound of the present invention is a highly effective and low-toxic therapeutic agent for ulcerative colitis, and thus has important academic value and practical significance.

Technical solutions of the present invention are further described below in combination with specific examples, but the following examples are not intended to limit the invention, and all methods of application according to the principles and technical means of the present invention shall fall within the scope of the invention. Experimental methods in the following examples which do not specify specific conditions are usually carried out according to conventional conditions or conditions recommended by manufacturers. Percentages and parts are calculated by weight unless otherwise stated.

Example 1

(E)-4-(2-chlorophenyl)-2-[1-methyl-2-(2-carboxy-benzylidene)hydrazino]thiazole 1

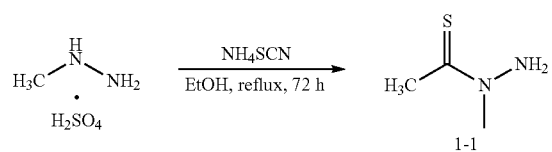

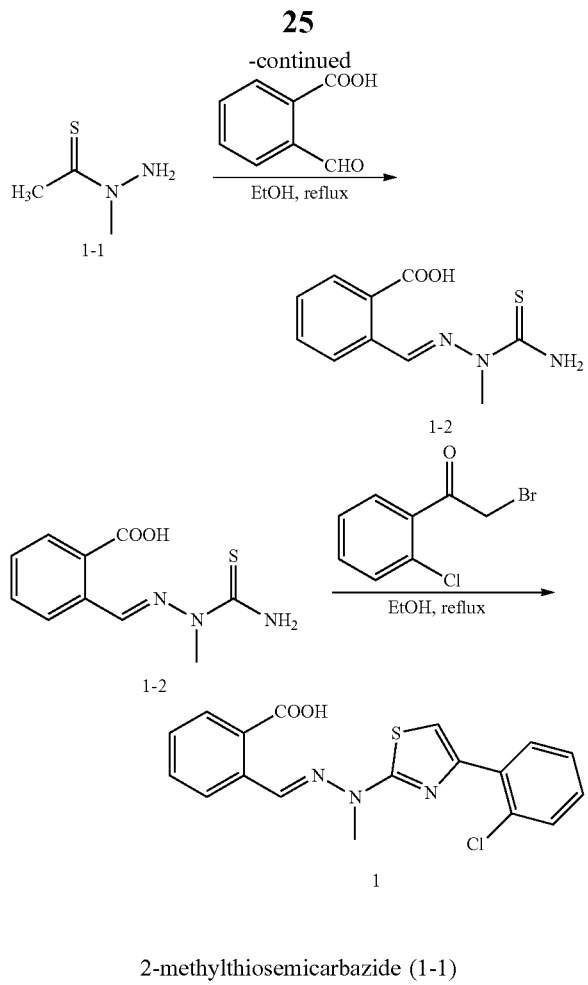

2-methylthiosemicarbazide (1-1)

2.5 g (17.3 mmol) of methyl hydrazine sulfate was weighed into a 250 ml single-mouth flask, 100 ml of ethanol was added, and 1.6 g (20.8 mmol) of ammonium thiocyanate was added with stirring. The reaction mixture was heated to reflux for 72 h. The reaction solution was cooled to room temperature and suction-filtered. The obtained filtrate was then evaporated to dryness and separated through silica gel column chromatography (DCM/MeOH=40:1) to give a second side product as white powdery solids (0.63 g, yield 34.2%). $^1$H NMR (400 MHz, DMSO-d6, ppm) δ 7.36 (s, 2H), 4.89 (s, 2H), 3.41 (s, 3H). GC-MS (EI) calcd for C2H7N3S [M]+ 105.0, found 105.0.

2-methyl-1-(2-carboxybenzylidene)thiosemicarbazide (1-2)

80 mg (0.76 mmol) of compound (1-1) was weighted into a 50 ml single-mouth flask, 20 ml of ethanol was added, and o-carboxybenzaldehyde (114 mg, 0.76 mmol) was added with stirring. The reaction mixture was heated to reflux, and the reaction was monitored by TLC until the starting materials were completely converted. The reaction solution was cooled to room temperature, and the solvent was evaporated to dryness. The obtained residue was separated through silica gel column chromatography (DCM/MeOH=120:1) to give white powdery solids (100 mg, yield 56%). $^1$H NMR (400 MHz, DMSO-$d_6$, ppm) δ 13.36 (br, 1H), 8.56 (s, 1H), 8.51 (s, 1H), 8.31 (d, J=7.8 Hz, 1H), 8.25 (s, 1H), 7.88 (d, J=8 Hz, 1H), 7.59 (t, J=7.2 Hz, 1H), 7.50 (t, J=7.2 Hz, 1H), 3.77 (s, 3H). LC-MS (ESI) calcd for $C_{10}H_{12}N_3O_2S$ [M+H]+ 238.1, found 238.1.

(E)-4-(2-chlorophenyl)-2-[1-methyl-2-(2-carboxy-benzylidene)hydrazino]thiazole 1

100 mg (0.42 mmol) of compound (2) was weighed into a 50 ml single-mouth flask, 10 ml of ethanol was added, and 65 μL (0.42 mmol) of 2'-chloro-2-bromoacetophenone was added with stirring. The reaction mixture was warmed to reflux, and the reaction was monitored by TLC until the starting materials were completely converted. The reaction solution was cooled to room temperature, and the solvent was evaporated to dryness. The obtained residue was separated through silica gel column chromatography (DCM/MeOH=120:1) to give yellow powdery solids (106 mg, yield 67.9%). Mp. 210.4-212.0° C. $^1$H NMR (400 MHz, DMSO-d6, ppm) δ 13.30 (s, 1H), 8.62 (s, 1H), 8.02 (d, J=7.6 Hz, 1H), 7.98-7.90 (m, 2H), 7.66 (t, J=7.6 Hz, 1H), 7.56-7.49 (m, 2H), 7.47 (s, 1H), 7.43 (td, $J_1$=7.4 Hz, $J_2$=1.2 Hz, 1H), 7.36 (td, $J_1$=7.6 Hz, $J_2$=1.6 Hz, 1H), 3.68 (s, 3H). $^{13}$C NMR (125 MHz, DMSO-$d_6$, ppm) δ 168.98, 168.57, 147.11, 136.94, 135.17, 133.42, 132.48, 131.51, 131.09, 130.98, 130.75, 130.16, 129.45, 129.19, 127.63, 126.51, 111.41, 32.88. HRMS (ESI) calcd for $C_{18}H_{15}N_3O_2SCl$ [M+H]+ 372.0574, found 372.0575.

The inventors further synthesized following compounds using a similar method and corresponding starting materials:

(E)-4-(2-chlorophenyl)-2-[1-ethyl-2-(2-carboxyben-zylidene)hydrazino]thiazole 2

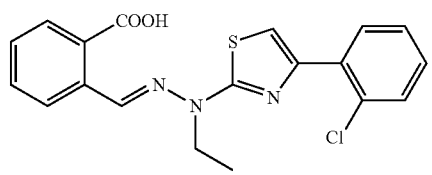 [SMILES: CCN(/N=C/c1ccccc1C(=O)O)c1nc(-c2ccccc2Cl)cs1]

Mp. 203.3-204.1° C. $^1$H NMR (500 MHz, DMSO-$d_6$, ppm) δ 13.32 (br, 1H), 8.64 (s, 1H), 7.98-7.91 (m, 3H), 7.66 (t, J=7.5 Hz, 1H), 7.56-7.46 (m, 2H), 7.45-7.39 (m, 2H), 7.34 (t, J=6.8 Hz, 1H), 4.32 (q, J=6.8 Hz, 2H), 1.27 (t, J=7.0 Hz, 3H). $^{13}$C NMR (125 MHz, DMSO-$d_6$, ppm) δ 168.56, 168.36, 147.34, 137.00, 135.42, 133.53, 132.50, 131.53, 131.12, 130.92, 130.72, 130.22, 129.42, 129.19, 127.62, 126.62, 111.22, 40.38, 10.33. HRMS (ESI) calcd for $C_{19}H_{17}N_3O_2SCl$ [M+H]+ 386.0730, found 386.0728.

(E)-4-(2-chlorophenyl)-2-[1-propyl-2-(2-carboxy-benzylidene)hydrazino]thiazole 3

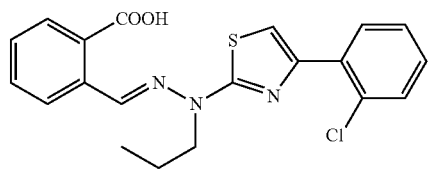 [SMILES: CCCN(/N=C/c1ccccc1C(=O)O)c1nc(-c2ccccc2Cl)cs1]

Mp. 172.6-173.4° C. $^1$H NMR (400 MHz, DMSO-$d_6$, ppm) δ 13.35 (br, 1H), 8.65 (s, 1H), 7.98 (d, J=8.0 Hz, 1H), 7.95-7.92 (m, 2H), 7.67 (t, J=7.2 Hz, 1H), 7.54 (d, J=8.0 Hz, 1H), 7.5 (t, J=7.6 Hz, 1H), 7.45-7.42 (m, 2H), 7.36 (t, $J_1$=7.6 Hz, $J_2$=1.6 Hz, 1H), 4.25 (t, J=7.2 Hz, 2H), 1.82-1.73 (m, 2H), 0.97 (t, J=7.4 Hz, 1H). $^{13}$C NMR (100 MHz, DMSO-d6, ppm) δ 168.54, 168.22 146.95, 136.63, 134.96, 133.17, 132.11, 131.10, 130.74, 130.55, 130.34, 129.82, 129.04, 128.80, 127.26, 126.09, 110.77, 46.31, 17.98, 11.17. HRMS (ESI) calcd for C20H19N3O2SCl [M+H]+ 400.0887, found 400.0879.

(E)-4-(2-chlorophenyl)-2-[1-isopropyl-2-(2-carboxybenzylidene)hydrazino]thiazole 4

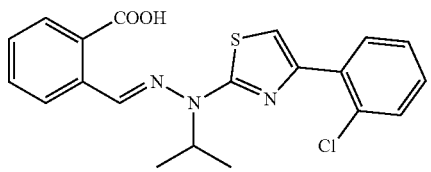 [SMILES: CC(C)N(/N=C/c1ccccc1C(=O)O)c1nc(-c2ccccc2Cl)cs1]

Mp. 185.4-187.0° C. $^1$H NMR (400 MHz, DMSO-$d_6$, ppm) δ 13.35 (br, 1H), 8.91 (s, 1H), 7.99 (d, J=8.0 Hz, 1H), 7.95-7.92 (m, 2H), 7.67 (t, J=7.6 Hz, 1H), 7.54 (d, J=8.0 Hz, 1H), 7.52 (t, J=7.6 Hz, 1H), 7.46-7.42 (m, 2H), 7.36 (td, $J_1$=7.6 Hz, $J_2$=1.6 Hz, 1H), 5.22-5.11 (m, 1H), 1.57 (d, J=6.8 Hz, 6H). $^{13}$C NMR (100 MHz, DMSO-$d_6$, ppm) δ 168.22, 168.21, 146.90, 137.32, 135.23, 133.14, 132.07, 131.06, 130.64, 130.58, 130.39, 129.88, 128.97, 128.78, 127.28, 125.91, 111.12, 49.61, 18.07, 18.07. HRMS (ESI) calcd for $C_{20}H_{19}N_3O_2SCl$ [M+H]+ 400.0887, found 400.0885.

(E)-4-(2-chlorophenyl)-2-[1-(2-butyl)-2-(2-carboxybenzylidene)hydrazino]thiazole 5

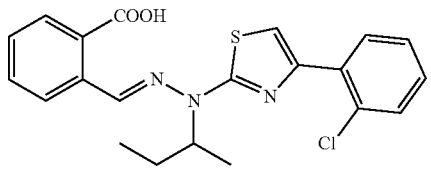 [SMILES: CCC(C)N(/N=C/c1ccccc1C(=O)O)c1nc(-c2ccccc2Cl)cs1]

Mp. 170.5-170.6° C. $^1$H NMR (400 MHz, DMSO-$d_6$, ppm) δ 13.32 (br, 1H), 8.91 (s, 1H), 7.99 (d, J=8.0 Hz, 1H), 7.95-7.90 (m, 2H), 7.67 (t, $J_1$=7.6 Hz, 1H), 7.55-7.48 (m, 2H), 7.46-7.42 (m, 2H), 7.36 (td, $J_1$=7.6 Hz, $J_2$=1.6 Hz, 1H), 5.00-4.93 (m, 1H), 2.35-2.24 (m, 1H), 1.92-1.81 (m, 1H), 1.54 (d, J=6.8 Hz, 3H), 0.88 (t, J=7.2 Hz, 3H). $^{13}$C NMR (100 MHz, DMSO-$d_6$, ppm) δ 168.66, 168.19, 146.97, 137.03, 135.24, 133.19, 132.13, 131.04, 130.67, 130.58, 130.39, 129.70, 128.98, 128.77, 127.29, 125.91, 111.04, 55.67, 25.26, 16.33, 11.14. HRMS (ESI) calcd for $C_{21}H_{21}N_3O_2SCl$ [M+H]+ 414.1043, found 414.1029.

(E)-4-(2-chlorophenyl)-2-[1-(2-amyl)-2-(2-carboxybenzylidene)hydrazino]thiazole 6

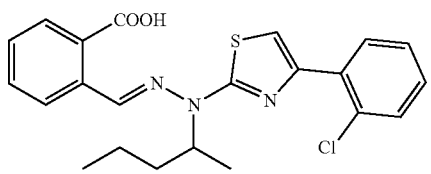 [SMILES: CCCC(C)N(/N=C/c1ccccc1C(=O)O)c1nc(-c2ccccc2Cl)cs1]

Mp. 146.7-147.0° C. $^1$H NMR (400 MHz, DMSO-$d_6$, ppm) δ 13.35 (br, 1H), 8.91 (s, 1H), 7.98 (d, J=7.6 Hz, 1H), 7.94 (d, J=8.0 Hz, 1H), 7.91 (dd, $J_1$=7.6 Hz, $J_2$=1.6 Hz, 1H), 7.67 (t, J=7.6 Hz, 1H), 7.53 (d, J=8.0 Hz, 1H), 7.49 (t, J=7.6 Hz, 1H), 7.46-7.42 (m, 2H), 7.36 (td, 7.6 Hz, $J_2$=1.6 Hz, 1H), 5.14-5.06 (m, 1H), 2.34-2.25 (m, 1H), 1.82-1.73 (m, 1H), 1.53 (d, J=6.8 Hz, 3H), 1.34-1.24 (m, 2H), 0.89 (t, J=7.4 Hz, 1H). $^{13}$C NMR (100 MHz, DMSO-$d_6$, ppm) δ 168.68, 168.20, 146.98, 137.04, 135.30, 133.20, 132.14, 131.00, 130.68, 130.59, 130.40, 129.68, 128.99, 127.30, 125.90, 111.09, 53.81, 34.20, 19.46, 16.46, 13.60. HRMS (ESI) calcd for $C_{22}H_{23}N_3O_2SCl$ [M+H]+ 428.1200, found 428.1193.

(E)-4-(2-chlorophenyl)-2-[11-hydroxyethyl-2-(2-carboxybenzylidene)hydrazino]thiazole 7

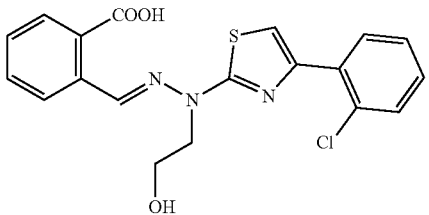 [SMILES: O=C(O)c1ccccc1/C=N/N(CCO)c1nc(-c2ccccc2Cl)cs1]

Mp. 187.9-188.9° C. $^1$H NMR (400 MHz, DMSO-$d_6$, ppm) δ 13.24 (br, 1H), 8.75 (s, 1H), 7.98-7.01 (m, 3H), 7.66 (t, J=7.6 Hz, 1H), 7.54 (d, J=8.0 Hz, 1H), 7.49 (t, J=7.6 Hz, 1H), 7.45-7.41 (m, 2H), 7.36 (td, $J_1$=7.6 Hz, $J_2$=1.6 Hz, 1H), 4.35 (t, J=6.4 Hz, 2H), 3.76 (t, J=6.4 Hz, 2H). $^{13}$C NMR (100 MHz, DMSO-$d_6$, ppm) δ 168.64, 168.23, 146.87, 136.89, 134.91, 133.15, 131.99, 131.19, 130.71, 130.46, 130.32, 130.16, 129.04, 128.79, 127.22, 126.28, 110.78, 56.24, 47.46. HRMS (ESI) calcd for $C_{19}H_{17}N_3O_3SCl$ [M+H]+ 402.0679, found 402.0678.

(E)-4-(2-chlorophenyl)-2-[1-methyl-2-(4-trifluoromethyl-2-carboxybenzylidene)hydrazino]thiazole 8

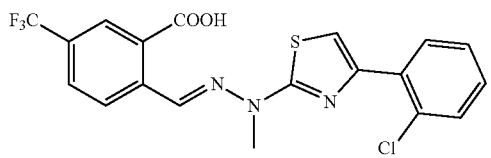 [SMILES: CN(/N=C/c1ccc(C(F)(F)F)cc1C(=O)O)c1nc(-c2ccccc2Cl)cs1]

Mp. 209.3-210.7° C. $^1$H NMR (400 MHz, DMSO-$d_6$, ppm) δ 14.02 (br, 1H), 8.66 (s, 1H), 8.21 (d, J=8.0 Hz, 1H), 8.17 (s, 1H), 8.02 (d, J=8.0 Hz, 1H), 7.95 (d, J=7.6 Hz, 1H), 7.56-7.53 (m, 2H), 7.43 (t, J=7.6 Hz, 1H), 7.37 (t, J=7.6 Hz, 1H), 3.70 (s, 3H). $^{13}$C NMR (100 MHz, DMSO-$d_6$, ppm) δ 168.33, 167.17, 146.79, 138.38, 135.01, 132.91, 131.12, 130.70, 130.37, 129.14, 128.57, 128.25, 128.20, 127.26, 127.04, 125.10, 122.40, 111.51, 32.68. HRMS (ESI) calcd for $C_{19}H_{14}N_3O_2SClF_3$ [M+H]+ 440.0447, found 440.0433.

(E)-4-(2-chlorophenyl)-2-[1-methyl-2-(4-methyl-2-carboxybenzylidene)hydrazino]thiazole 9

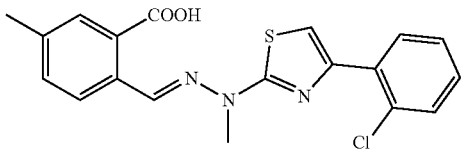 [SMILES: Cc1ccc(/C=N/N(C)c2nc(-c3ccccc3Cl)cs2)c(C(=O)O)c1]

Mp. 231.3-232.5° C. $^1$H NMR (400 MHz, DMSO-d$_6$, ppm) δ 13.30 (br, 1H), 8.59 (s, 1H), 7.96 (d, J=7.6 Hz, 1H), 7.92 (d, J=8.0 Hz, 1H), 7.75 (s, 1H), 7.54 (d, J=7.6 Hz, 1H), 7.49-7.46 (m, 2H), 7.43 (t, J=7.6 Hz, 1H), 7.36 (t, J=7.6 Hz, 1H), 3.66 (s, 3H), 2.38 (s, 3H). $^{13}$C NMR (100 MHz, DMSO-d$_6$, ppm) δ 168.60, 168.35, 146.68, 138.54, 136.64, 133.03, 132.70, 132.07, 131.11, 130.86, 130.67, 130.34, 129.83, 129.00, 127.21, 126.04, 110.84, 32.39, 20.69. HRMS (ESI) calcd for C$_{19}$H$_{17}$N$_3$O$_2$SCl [M+H]$^+$ 386.0730, found 386.0738.

(E)-4-(2-chlorophenyl)-2-[1-methyl-2-(2-carboxyl-4-fluorobenzylidene)hydrazino]thiazole 10

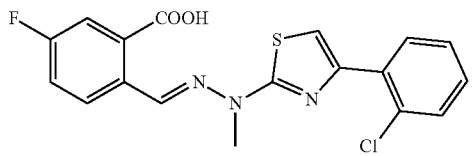 [SMILES: CN(/N=C/c1ccc(F)cc1C(=O)O)c1nc(-c2ccccc2Cl)cs1]

Mp. 228.6-229.7° C. $^1$H NMR (400 MHz, DMSO-d$_6$, ppm) δ 13.28 (br, 1H), 8.14 (s, 1H), 7.93 (dd, J$_1$=7.6 Hz, J$_2$=1.6 Hz, 1H), 7.61 (dd, J$_1$=7.0 Hz, J$_2$=1.8 Hz, 1H), 7.55-7.49 (m, 3H), 7.44-7.41 (m, 1H), 7.36 (td, J$_1$=7.6 Hz, J$_2$=1.6 Hz, 1H), 3.68 (s, 3H). $^{13}$C NMR (100 MHz, DMSO-d$_6$, ppm) δ 168.55, 168.01, 159.74 (d, $^1$J=249 Hz), 146.67, 133.68, 133.10, 131.50, 131.12, 130.72, 130.32, 130.10 (d, $^3$J=8.8 Hz), 129.06, 127.23, 125.53 (d, $^4$J=3.1 Hz), 121.75 (d, $^2$J=11.8 Hz), 118.76 (d, $^2$J=22 Hz), 111.13, 32.28. HRMS (ESI) calcd for C$_{18}$H$_{14}$N$_3$O$_2$FSCl [M+H]$^+$ 390.0479, found 390.0475.

(E)-5-methyl-4-phenyl-2-[11-methyl-2-(4-methyl-2-carboxybenzylidene)hydrazino]thiazole 11

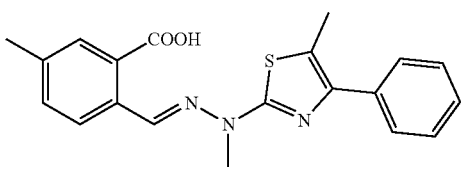 [SMILES: Cc1ccc(/C=N/N(C)c2nc(-c3ccccc3)c(C)s2)c(C(=O)O)c1]

Mp. 243.2-245.2° C. $^1$H NMR (400 MHz, DMSO-d6, ppm) δ 13.24 (br, 1H), 8.54 (s, 1H), 7.91 (d, J=8.0 Hz, 1H), 7.73 (s, 1H), 7.64-7.53 (m, 2H), 7.46-7.42 (m, 3H), 7.33 (t, J=7.4 Hz, 1H), 3.60 (s, 3H), 2.44 (s, 3H), 2.38 (s, 3H). $^{13}$C NMR (100 MHz, DMSO-d$_6$, ppm) δ 168.35, 165.40, 145.43, 138.33, 135.76, 135.16, 132.68, 132.22, 130.86, 129.62, 128.24, 128.24, 127.85, 127.85, 127.06, 125.89, 119.27, 31.85, 20.68, 12.24. HRMS (ESI) calcd for C$_{20}$H$_{20}$N$_3$O$_2$S [M+H]$^+$ 366.1276, found 366.1273.

(E)-5-methyl-4-phenyl-2-[11-methyl-2-(2-carboxy-benzylidene)hydrazino]thiazole 12

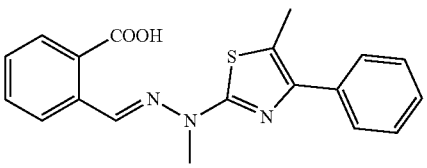 [SMILES: Cc1sc(N(C)/N=C/c2ccccc2C(=O)O)nc1-c1ccccc1]

Mp. 222.7-224.9° C. $^1$H NMR (400 MHz, DMSO-d$_6$, ppm) δ 13.32 (br, 1H), 8.58 (s, 1H), 8.01 (d, J=8.0 Hz, 1H), 7.92 (d, J=7.6 Hz, 1H), 7.68-7.63 (m, 3H), 7.50-7.43 (m, 3H), 7.34 (t, J=7.4 Hz, 1H), 3.62 (s, 3H), 2.44 (s, 3H). $^{13}$C NMR (100 MHz, DMSO-d$_6$, ppm) δ 168.24, 165.36, 145.47, 135.66, 135.13, 134.90, 131.98, 130.58, 129.70, 128.59, 128.25, 128.25, 127.86, 127.86, 127.09, 125.94, 119.44, 31.93, 12.24. HRMS (ESI) calcd for C$_{19}$H$_{16}$N$_3$O$_2$S [M–H]$^-$ 350.0963, found 350.0951.

(E)-4-(2-chlorophenyl)-2-[1-methyl-2-(2-carboxy-benzylidene)hydrazino]thiazole 13

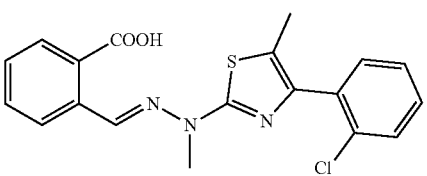 [SMILES: Cc1sc(N(C)/N=C/c2ccccc2C(=O)O)nc1-c1ccccc1Cl]

Mp. 208.8-209.8° C. $^1$H NMR (400 MHz, DMSO-d$_6$, ppm) δ 13.46 (br, 1H), 8.60 (s, 1H), 8.01 (d, J=8.0 Hz, 1H), 7.92 (d, J=8.0 Hz, 1H), 7.64 (t, J=7.4 Hz, 1H), 7.56 (d, J=7.6 Hz, 1H), 7.49-7.39 (m, 4H), 3.56 (s, 3H), 2.15 (s, 3H). $^{13}$C NMR (100 MHz, DMSO-d$_6$, ppm) δ 168.98, 166.46, 144.56, 136.46, 135.29, 134.54, 133.25, 132.50, 132.31, 131.05, 130.72, 130.26, 130.01, 129.09, 127.49, 126.42, 121.85, 32.46, 12.16. HRMS (ESI) calcd for C$_{19}$H$_{17}$N$_3$O$_2$SCl [M+H]$^+$ 386.0730, found 386.0727.

(E)-5-ethyl-4-(2-chlorophenyl)-2-(2-carboxylbenzylidenehydrazino)thiazole 14

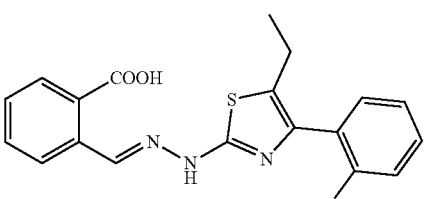

Mp. 223.9-223.9° C. $^1$H NMR (500 MHz, DMSO-d$_6$, ppm) δ 12.57 (br, 2H), 8.79 (s, 1H), 8.01 (d, J=8.0 Hz, 1H), 7.88 (d, J=8.0 Hz, 1H), 7.62 (t, J=7.5 Hz, 1H), 7.56-7.51 (m, 1H), 7.46 (t, J=7.5 Hz, 1H), 7.44-7.36 (m, 3H), 2.49 (q, J=7.5 Hz, 1H), 1.13 (t, J=7.5 Hz, 3H). $^{13}$C NMR (125 MHz, DMSO-d$_6$, ppm) δ 169.28, 165.92, 144.14, 140.84, 135.89, 135.46, 133.99, 133.03, 133.02, 131.46, 130.81, 130.73, 130.60, 129.73, 128.09, 127.73, 127.01, 20.99, 17.25. HRMS (ESI) calcd for C$_{19}$H$_{17}$N$_3$O$_2$SCl [M+H]$^+$ 386.0730, found 386.0729.

(E)-5-methyl-4-(2-chlorophenyl)-2-(2-carboxylbenzylidenehydrazino)thiazole 15

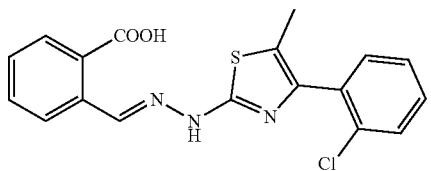 [SMILES: Cc1sc(N/N=C/c2ccccc2C(=O)O)nc1-c1ccccc1Cl]

Mp. 217.6-217.8° C. $^1$H NMR (400 MHz, DMSO-d$_6$, ppm) δ 12.7 (br, 2H), 8.77 (s, 1H), 7.99 (d, J=7.6 Hz, 1H), 7.87 (d, J=7.2 Hz, 1H), 7.62 (t, J=7.4 Hz, 1H), 7.562-7.543 (m, 1H), 7.481-7.397 (m, 4H), 2.14 (s, 3H). $^{13}$C NMR (125 MHz, DMSO-d$_6$, ppm) δ 168.65, 165.18, 144.49, 140.16, 135.25, 134.56, 133.21, 132.46, 130.83, 130.14, 130.03, 129.11, 127.45, 126.37, 119.49, 12.15. HRMS (ESI) calcd for C$_{18}$H$_{15}$N$_3$O$_2$SCl [M+H]$^+$ 372.0574, found 372.0569.

(E)-4-(2-chlorophenyl)-2-(2-carboxybenzylidenehydrazino)thiazole 16

Mp. 200.2-200.9° C. $^1$H NMR (400 MHz, DMSO-d6, ppm) δ 13.2 (br, 1H), 12.4 (br, 1H), 8.82 (s, 1H), 8.00 (d, J=7.6 Hz, 1H), 7.89-7.86 (m, 2H), 7.64 (t, J=7.4 Hz, 1H), 7.53 (dd, J1=7.6 Hz, J$_2$=1.2 Hz, 1H), 7.49 (td, J1=7.6 Hz, J$_2$=1.2 Hz, 1H), 7.42 (td, J1=7.6 Hz, J$_2$=1.2 Hz, 1H), 7.36 (m, 2H). 13C NMR (100 MHz, DMSO-d6, ppm) δ 168.63, 167.77, 147.63, 140.76, 135.08, 133.71, 132.43, 131.54, 131.23, 130.83, 130.83, 130.26, 129.47, 129.28, 127.69, 126.47, 109.26. HRMS (ESI) calcd for C17H13N3O2SCl [M+H]$^+$ 358.0417, found 358.0417.

(E)-5-methyl-4-phenyl-2-(2-carboxylbenzylidenehydrazino)thiazole 17

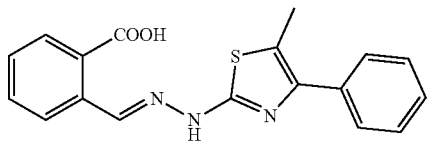 [SMILES: Cc1sc(N/N=C/c2ccccc2C(=O)O)nc1-c1ccccc1]

Mp. 215.9-216.0° C. $^1$H NMR (400 MHz, DMSO-d$_6$, ppm) δ 12.7 (br, 2H), 8.77 (s, 1H), 7.99 (d, J=7.6 Hz, 1H), 7.87 (dd, J$_1$=8.0 Hz, J$_2$=1.2 Hz, 1H), 7.63-7.59 (m, 3H), 7.48-7.43 (m, 3H), 7.33 (t, J=7.2 Hz, 1H), 2.43 (s, 3H). $^{13}$C NMR (125 MHz, DMSO-d$_6$, ppm) δ 168.66, 164.72, 146.00, 140.05, 135.64, 135.24, 132.36, 130.83, 130.12, 129.08, 128.73, 128.73, 128.35, 128.35, 127.51, 126.33, 117.61, 12.74. HRMS (ESI) calcd for C$_{18}$H$_{16}$N$_3$O$_2$S [M+H]$^+$ 338.0963, found 338.0954.

(E)-4-phenyl-2-(2-carboxybenzylidenehydrazino)thiazole 18

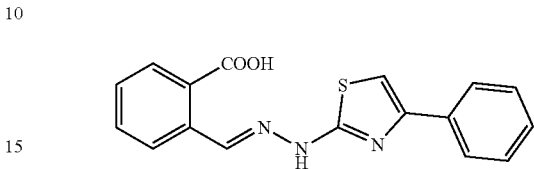

Mp. 163.8-165.6° C. $^1$H NMR (400 MHz, DMSO-d$_6$, ppm) δ 13.45 (br, 1H), 12.49 (br, 1H), 8.81 (s, 1H), 7.99 (d, J=7.6 Hz, 1H), 7.87 (m, 3H), 7.63 (t, J=7.4 Hz, 1H), 7.47 (t, J=7.2 Hz, 1H), 7.41 (t, J=7.6 Hz, 2H), 7.33 (s, 1H), 7.30 (t, J=7.4 Hz, 1H). $^{13}$C NMR (100 MHz, DMSO-d$_6$, ppm) δ 168.53, 168.53, 150.97, 140.58, 135.02, 134.99, 132.31, 130.74, 130.15, 129.15, 128.96, 128.96, 127.90, 126.34, 125.90, 125.90, 104.20. HRMS (ESI) calcd for C$_{18}$H$_{16}$N$_3$O$_2$S [M−H]$^-$ 322.0650, found 322.0656.

(E)-4-(2,5-dichlorophenyl)-2-[1-methyl-2-(2-carboxybenzylidene)hydrazino]thiazole 19

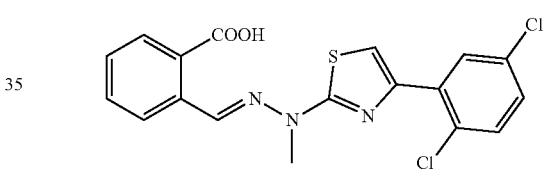

Mp. 268.4-269.5° C. $^1$H NMR (400 MHz, DMSO-d$_6$, ppm) δ 13.31 (br, 1H), 8.63 (s, 1H), 8.02-8.00 (m, 2H), 7.93 (d, J=7.2 Hz, 1H), 7.67 (t, J=7.6 Hz, 1H), 7.63 (s, 1H), 7.58 (d, J=7.6 Hz, 1H), 7.50 (t, J=7.2 Hz, 1H), 7.43 (dd, J$_1$=7.2 Hz, J$_2$=2.8 Hz, 1H), 3.68 (s, 3H). $^{13}$C NMR (100 MHz, DMSO-d$_6$, ppm) δ 168.68, 168.15, 145.13, 136.79, 134.70, 134.21, 132.14, 132.06, 131.85, 130.59, 130.17, 129.76, 129.20, 128.84, 128.58, 126.13, 112.31, 32.49. HRMS (ESI) calcd for C$_{18}$H$_{14}$N$_3$O$_2$SCl$_2$ [M+H]$^+$ 406.0184, found 406.0187.

(E)-4-phenyl-2-[1-methyl-2-(2-carboxybenzylidene)hydrazino]thiazole 20

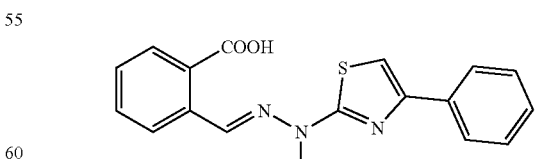

Mp. 205.6-206.8° C. $^1$H NMR (400 MHz, DMSO-d$_6$, ppm) δ 13.31 (br, 1H), 8.62 (s, 1H), 8.02 (d, J=7.6 Hz, 1H), 7.94-7.91 (m, 3H), 7.66 (t, J=7.2 Hz, 1H), 7.49 (t, J=7.2 Hz, 1H), 7.45-7.40 (m, 3H), 7.31 (t, J=7.2 Hz, 1H), 3.71 (s, 3H). $^{13}$C NMR (100 MHz, DMSO-d$_6$, ppm) δ 169.45, 168.20, 150.18, 136.35, 134.80, 134.49, 132.07, 130.60, 129.71, 128.76, 128.56, 128.56, 127.59, 126.09, 125.54, 125.54, 105.97, 32.51. HRMS (ESI) calcd for $C_{18}H_{16}N_3O_2S$ [M+H]$^+$ 338.0963, found 338.0963.

(E)-4-(3-chlorophenyl)-2-[1-methyl-2-(2-carboxybenzylidene)hydrazino]thiazole 21

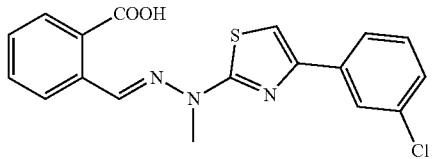 [SMILES: CN(/N=C/c1ccccc1C(=O)O)c1nc(-c2cccc(Cl)c2)cs1]

Mp. 244.7-245.4° C. $^1$H NMR (400 MHz, DMSO-d$_6$, ppm) δ 13.32 (br, 1H), 8.63 (s, 1H), 8.01 (d, J=7.6 Hz, 1H), 7.97 (s, 1H), 7.93 (d, J=7.6 Hz, 1H), 7.88 (d, J=8.0 Hz, 1H), 7.66 (t, J=7.6 Hz, 1H), 7.61 (s, 1H), 7.50 (t, J=7.6 Hz, 1H), 7.45 (t, J=7.6 Hz, 1H), 7.37 (d, J=8.0 Hz, 1H), 3.71 (s, 3H). $^{13}$C NMR (100 MHz, DMSO-d$_6$, ppm) δ 169.57, 168.18, 148.56, 136.64, 136.50, 134.72, 133.48, 132.06, 130.59, 130.44, 129.76, 128.81, 127.28, 126.12, 125.16, 124.05, 107.56, 32.52. HRMS (ESI) calcd for $C_{18}H_{15}N_3O_2SCl$ [M+H]$^+$ 372.0574, found 372.0574.

(E)-5-methyl-4-(2-chlorophenyl)-2-[1-(2-amyl)-2-(2-carboxybenzylidene)hydrazino]thiazole 22

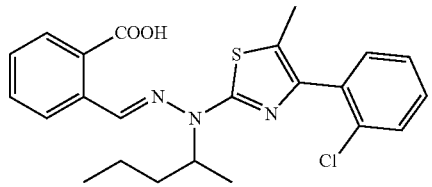 [SMILES: CCCC(C)N(/N=C/c1ccccc1C(=O)O)c1nc(-c2ccccc2Cl)c(C)s1]

Mp. 89.9-90.1° C. $^1$H NMR (400 MHz, DMSO-d$_6$, ppm) δ 13.29 (br, 1H), 8.85 (s, 1H), 7.98 (d, J=8.0 Hz, 1H), 7.92 (d, J=7.6 Hz, 1H), 7.65 (t, J=7.6 Hz, 1H), 7.56-7.54 (m, 1H), 7.51-7.41 (m, 4H), 5.05-4.96 (m, 1H), 2.29-2.22 (m, 1H), 2.16 (s, 3H), 1.75-1.67 (m, 1H), 1.46 (d, J=7.2 Hz, 3H), 1.28-1.23 (m, 2H), 0.87 (t, J=7.6 Hz, 3H). $^{13}$C NMR (100 MHz, DMSO-d$_6$, ppm) δ 168.23, 166.06, 144.08, 136.14, 135.46, 134.09, 132.79, 132.09, 131.93, 130.58, 129.64, 129.60, 129.48, 128.56, 126.95, 125.73, 121.62, 53.39, 34.01, 19.41, 16.35, 13.58, 11.52. HRMS (ESI) calcd for $C_{23}H_{25}N_3O_2SCl$ [M+H]$^+$ 442.1356, found 442.1354.

(E)-2-((2-(4-(3-methoxyphenyl)thiazol-2-yl)hydrazono)methyl)benzoic acid (52)

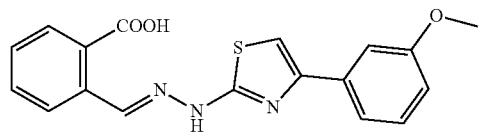 [SMILES: COc1cccc(-c2csc(N/N=C/c3ccccc3C(=O)O)n2)c1]

Mp: 167.3-167.9° C. $^1$H NMR (400 MHz, DMSO-d$_6$): δ 12.80 (s, 1H), 8.82 (s, 1H), 8.00 (d, J=8.0 Hz, 1H), 7.88 (d, J=7.6 Hz, 1H), 7.62 (t, J=7.6 Hz, 1H), 7.49-7.43 (m, 3H), 7.37 (s, 1H), 7.32 (t, J=8.0 Hz, 1H), 6.88 (dd, J$_1$=8.4 Hz, J$_2$=2.0 Hz, 1H), 3.80 (s, 3H). $^{13}$C NMR (100 MHz, DMSO-d$_6$): 168.67, 168.52, 159.99, 150.90, 140.75, 136.52, 135.04, 132.36, 130.81, 130.40, 130.12, 129.26, 126.43, 118.41, 113.80, 111.31, 104.71, 55.52. HRMS (ESI) calcd for $C_{18}H_{14}N_3O_3S$ [M–H]$^-$ 352.0756, found 352.0754. Purity: 95.56% (t$_R$ 7.94 min).

(E)-2-((2-(4-(3-aminoformylphenyl)thiazol-2-yl)hydrazono)methyl)benzoic Acid (53)

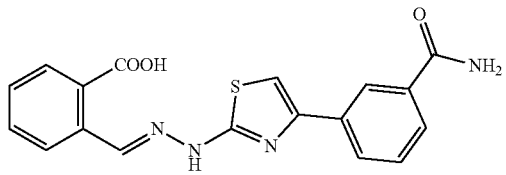 [SMILES: NC(=O)c1cccc(-c2csc(N/N=C/c3ccccc3C(=O)O)n2)c1]

Mp: 297.9-298.4° C. $^1$H NMR (400 MHz, DMSO-d$_6$): δ 12.20 (s, 1H), 8.83 (s, 1H), 8.39 (s, 1H), 8.05 (s, 1H), 8.00 (dd, J$_1$=7.2 Hz, J$_2$=3.2 Hz, 2H), 7.88 (d, J=7.6 Hz, 1H), 7.80 (d, J=7.6 Hz, 1H), 7.63 (t, J=7.6 Hz, 1H), 7.51-7.46 (m, 2H), 7.41 (s, 2H). $^{13}$C NMR (100 MHz, DMSO-d$_6$): 168.77, 168.67, 168.44, 150.57, 140.83, 135.19, 135.14, 135.02, 132.40, 130.83, 130.36, 129.31, 129.03, 128.62, 126.91, 126.46, 125.36, 105.00. HRMS (ESI) calcd for $C_{18}H_{15}N_4O_3S$ [M+H]$^+$ 367.0865, found 367.0863. Purity: 97.89% (t$_R$ 7.832 min).

(E)-2-((2-(4-(p-tolyl)thiazol-2-yl)hydrazono)methyl)benzoic Acid (54)

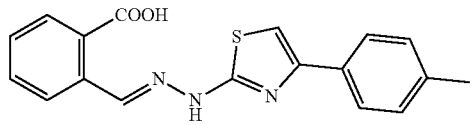 [SMILES: Cc1ccc(-c2csc(N/N=C/c3ccccc3C(=O)O)n2)cc1]

Mp: 225.5-226.1° C. $^1$H NMR (400 MHz, DMSO-d$_6$): δ 12.80 (s, 1H), 8.83 (s, 1H), 8.00 (d, J=7.2 Hz, 1H), 7.88 (d, J=7.6 Hz, 1H), 7.75 (d, J=8.0 Hz, 2H), 7.62 (t, J=7.6 Hz, 1H), 7.47 (t, J=7.6 Hz, 1H), 7.25 (s, 1H), 7.21 (t, J=8.0 Hz, 2H), 2.32 (s, 3H). $^{13}$C NMR (100 MHz, DMSO-d$_6$): 168.73, 168.55, 151.12, 140.69, 137.26, 135.04, 132.50, 132.29, 130.80, 130.56, 129.63, 129.22, 126.39, 125.96, 103.37, 21.27. HRMS (ESI) calcd for $C_{18}H_{14}N_3O_2S$ [M–H]$^-$ 336.0807, found 336.0808. Purity: 96.31% (t$_R$ 13.17 min).

(E)-2-((2-(4-(2,5-dichlorophenyl)thiazol-2-yl)hydrazono)methyl)benzoic Acid (55)

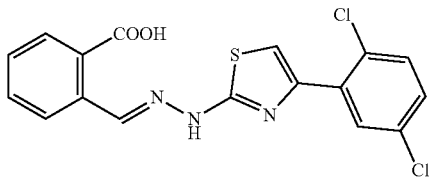 [SMILES: O=C(O)c1ccccc1/C=N/Nc1nc(-c2cc(Cl)ccc2Cl)cs1]

Mp: 205.0-206.0° C. $^1$H NMR (400 MHz, DMSO-d$_6$): δ 12.20 (s, 1H), 8.84 (s, 1H), 7.99 (d, J=7.2 Hz, 1H), 7.95 (d,

J=6.4 Hz, 1H), 7.88 (d, J=8.0 Hz, 1H), 7.62 (t, J=7.2 Hz, 1H), 7.57 (d, J=8.4 Hz, 1H), 7.52 (s, 1H), 7.47 (t, J=7.6 Hz, 1H), 7.41 (dd, J$_1$=8.8 Hz, J$_2$=2.8 Hz, 1H). $^{13}$C NMR (100 MHz, DMSO-d$_6$): 168.67, 167.90, 146.07, 141.15, 135.02, 134.92, 132.65, 132.33, 132.28, 130.82, 130.74, 130.62, 129.74, 129.35, 129.03, 126.46, 110.57. HRMS (ESI) calcd for C$_{17}$H$_{18}$N$_3$O$_2$SCl$_2$ [M–H]$^-$ 389.9871, found 389.9871. Purity: 97.66% (t$_R$ 9.88 min).

(E)-2-((2-(4-(naphthalen-2-yl)thiazol-2-yl)hydrazono)methyl)benzoic Acid (56)

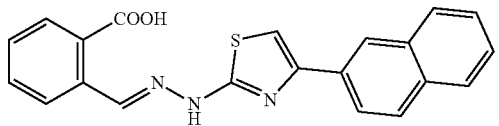 [SMILES: O=C(O)c1ccccc1/C=N/Nc1nc(-c2ccc3ccccc3c2)cs1]

Mp: 238.1-239.4° C. $^1$H NMR (400 MHz, DMSO-d$_6$): δ 12.80 (s, 1H), 8.87 (s, 1H), 8.40 (s, 1H), 8.04-8.01 (m, 2H), 7.96-7.89 (m, 4H), 7.64 (t, J=7.6 Hz, 1H), 7.54-7.46 (m, 4H). $^{13}$C NMR (100 MHz, DMSO-d$_6$): 168.75, 168.68, 151.02, 140.83, 135.07, 133.65, 132.92, 132.58, 132.40, 130.85, 130.39, 129.29, 128.63, 128.57, 128.05, 126.90, 126.47, 124.57, 124.43, 105.15. HRMS (ESI) calcd for C$_{21}$H$_{16}$N$_3$O$_2$S [M+H]$^+$ 374.0963, found 374.0959. Purity: 96.39% (t$_R$ 19.11 min).

(E)-2-((2-(4-(biphenyl-4-yl)thiazol-2-yl)hydrazono)methyl)benzoic Acid (57)

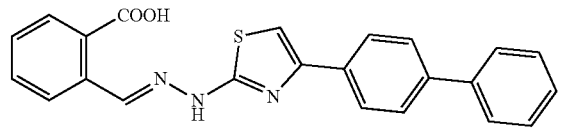 [SMILES: O=C(O)c1ccccc1/C=N/Nc1nc(-c2ccc(-c3ccccc3)cc2)cs1]

Mp: 227.1-228.1° C. $^1$H NMR (400 MHz, DMSO-d$_6$): δ 12.35 (s, 1H), 8.83 (s, 1H), 8.01 (d, J=6.0 Hz, 1H), 7.96 (d, J=6.8 Hz, 2H), 7.88 (d, J=6.0 Hz, 1H), 7.74-7.71 (m, 4H), 7.64 (t, J=6.4 Hz, 1H), 7.48 (t, J=6.0 Hz, 3H), 7.42 (s, 1H), 7.38 (t, J=6.0 Hz, 1H). $^{13}$C NMR (100 MHz, DMSO-d$_6$): 169.31, 169.31, 151.40, 141.42, 140.82, 140.22, 135.75, 134.93, 133.11, 131.52, 130.98, 130.12, 129.97, 128.62, 127.99, 127.63, 127.26, 127.14, 105.26. HRMS (ESI) calcd for C$_{23}$H$_{18}$N$_3$O$_2$S [M+H]$^+$ 400.1120, found 400.1114. Purity: 97.60% (t$_R$ 9.16 min).

(E)-2-((2-(4-(2-chlorophenyl)thiazol-2-yl)hydrazono)methyl)-6-fluorobenzoic Acid (58)

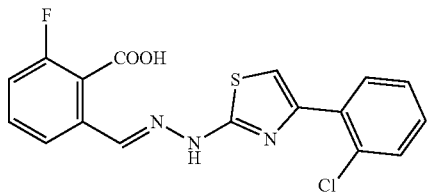 [SMILES: O=C(O)c1c(F)cccc1/C=N/Nc1nc(-c2ccccc2Cl)cs1]

Mp: 211.2-211.7° C. $^1$H NMR (400 MHz, DMSO-d$_6$): δ 12.40 (s, 1H), 8.18 (s, 1H), 7.86 (dd, =7.6 Hz, J$_2$=1.6 Hz, 1H), 7.69 (d, J=8.0 Hz, 1H), 7.55-7.50 (m, 2H), 7.41 (t, J=7.6 Hz, 1H), 7.37 (s, 1H), 7.35 (t, J=7.6 Hz, 1H), 7.29 (t, J=8.8 Hz, 1H). $^{13}$C NMR (100 MHz, DMSO-d$_6$): 167.56, 166.14, 160.51, 158.06, 147.64, 138.21, 138.17, 133.94, 133.89, 133.68, 131.54, 131.25, 130.83, 129.53, 127.72, 122.04, 116.51, 116.29, 109.58. HRMS (ESI) calcd for C$_{17}$H$_{10}$N$_3$O$_2$SClF [M–H]$^-$ 374.0166, found 374.0164. Purity: 97.09% (t$_R$ 12.05 min).

(E)-2-((2-(4-(2-chlorophenyl)thiazol-2-yl)hydrazono)methyl)-3-amino fluorobenzoic Acid (59)

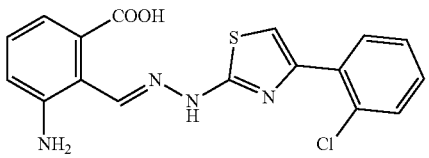 [SMILES: Nc1cccc(C(=O)O)c1/C=N/Nc1nc(-c2ccccc2Cl)cs1]

mp 220.9-221.6° C. $^1$H NMR (400 MHz, DMSO-d$_6$): δ 12.8 (s, 1H), 11.1 (s, 1H), 7.93 (s, 1H), 7.89 (d, J=7.2 Hz, 1H), 7.62 (d, J=7.6 Hz, 1H), 7.52-7.43 (m, 3H), 7.12 (d, J=7.2 Hz, 1H), 7.08 (d, J=8.4 Hz, 1H), 6.77 (s, 2H). $^{13}$C NMR (100 MHz, DMSO-d$_6$): δ 165.84, 155.22, 154.28, 147.07, 146.30, 133.99, 132.71, 131.65, 131.51, 131.09, 130.33, 129.73, 128.14, 121.28, 114.49, 113.14, 111.55. Purity: 97.06% (t$_R$ 19.58 min).

Ethyl 2-formylbenzoate 1a

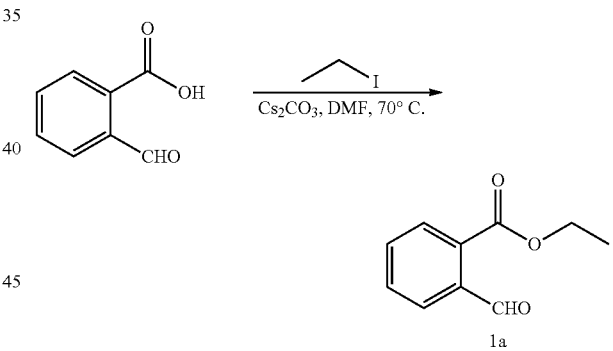

o-carboxybenzaldehyde (1.5 g, 10 mmol) was weighed into a 100 mL three-necked flask, cesium carbonate (6.5 g, 20 mmol) and 20 ml of N,N-dimethylformamide (DMF) were added, and ethyl iodide (4.68 g, 30 mmol) was added with electromagnetic-stirring and heated to 70° C. for 4 h. The reaction was monitored by TLC until the end of the reaction, and the heating was stopped. 20 mL of water was added to the reaction flask. The reaction mixture was extracted for three times with dichloromethane and water. The organic phases were pooled and dried over anhydrous sodium sulfate and suction-filtered, and the filtrate was evaporated to dryness and purified through silica gel column chromatography to give a colorless transparent liquid (1.4 g, yield 79%). $^1$H NMR (400 MHz, DMSO-d$_6$, ppm): δ 10.41 (s, 1H), 7.92-7.90 (m, 1H), 7.88-7.85 (m, 1H), 7.81-7.77 (m, 2H), 4.40 (q, J=7.2 Hz, 2H), 1.34 (t, J=7.2 Hz, 3H). LC-MS (ESI) calcd for C$_{10}$H$_{10}$O$_3$ [M+H]$^+$ 179.06, found 179.10.

(E)-4-(2-chlorophenyl)-2-(2-ethoxyformylbenzylidenehydrazino)thiazole A1

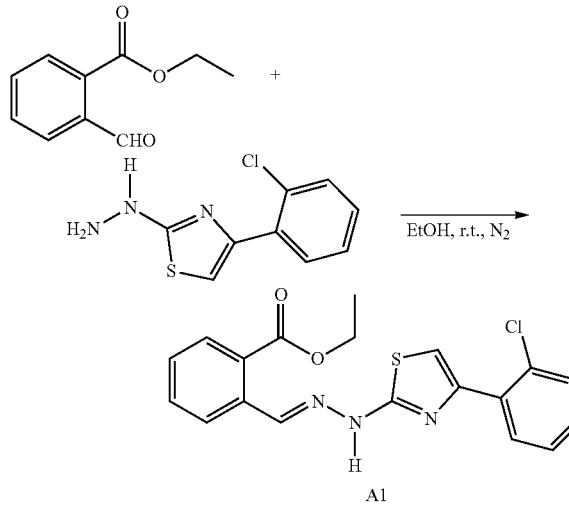

Compound 1a (178 mg, 1 mmol) was weighed into a 50 mL two-necked flask, another compound 3 (225 mg, 1 mmol) was added to the reaction flask, 15 mL of absolute ethanol was added, and the reaction was stirred under nitrogen for 4 h. The reaction was monitored by TLC until the starting materials were completely converted. The reaction mixture was suction-filtered, and the filter cake was rinsed with ethanol and dried to obtain 280 mg of a nearly pure product. After purification through a column, 220 mg of a pale yellow solid powder was obtained (yield 57%). Mp: 172.1-172.8° C. $^1$H NMR (400 MHz, DMSO-d$_6$, ppm): δ13.30 (br, 1H), 12.05 (br, 1H), 8.84 (s, 1H), 8.02 (d, J=7.6 Hz, 1H), 7.91 (t, J=8.0 Hz, 2H), 7.66 (t, J=7.2 Hz, 1H), 7.55 (d, J=7.6 Hz, 1H), 7.51 (t, J=8 Hz, 1H), 7.44 (t, J=7.2 Hz, 1H), 7.38-7.34 (m, 2H). $^{13}$C NMR (100 MHz, DMSO-d$_6$, ppm): δ 167.92, 16.70, 147.26, 141.03, 134.55, 133.23, 131.94, 131.82, 131.06, 130.70, 130.34, 128.80, 128.74, 128.60, 127.22, 125.96, 109.26, 61.23, 14010. HRMS (ESI) calcd for C$_{19}$H$_{17}$N$_3$O$_2$SCl [M+H]$^+$ 386.0730, found 386.0731. HPLC purity: 98.88%, Retention time=16.14 min.

7.90 (m, 1H), 7.88-7.84 (m, 1H), 7.81-7.77 (m, 2H), 4.29 (t, J=6.6 Hz, 2H), 1.74 (h, J=7.1 Hz, 2H), 0.97 (t, J=7.4 Hz, 3H). LC-MS (ESI) calcd for C$_{11}$H$_{12}$O$_3$ [M+H]$^+$ 193.08, found 193.10.

(E)-4-(2-chlorophenyl)-2-(2-propoxyformylbenzylidenehydrazino)thiazole A2

180 mg of a pale yellow solid powder (yield 58%) was obtained according to the same synthesis method as that for A1. $^1$H NMR (400 MHz, DMSO-d$_6$, ppm): δ 12.40 (s, 1H), 8.71 (s, 1H), 8.00 (d, J=7.9 Hz, 1H), 7.88 (d, J=7.6, 2.4 Hz, 2H), 7.67 (t, J=7.6 Hz, 1H), 7.52 (q, J=7.9 Hz, 2H), 7.46-7.32 (m, 3H), 4.26 (t, J=6.5 Hz, 2H), 1.76 (h, J=7.1 Hz, 2H), 0.98 (t, J=7.3 Hz, 3H). $^{13}$C NMR (100 MHz, DMSO-d$_6$, ppm): δ 167.68, 167.03, 147.63, 140.16, 134.95, 133.6, 132.71, 131.53, 131.22, 130.85, 130.59, 129.52, 129.4, 129.38, 127.73, 126.74, 109.35, 67.06, 21.96, 10.87. HRMS (ESI) calcd for C$_{20}$H$_{18}$N$_3$O$_2$SCl [M+H]$^+$ 400.0808, found 400.0888. HPLC purity: 96.95%, Retention time=12.44 min.

Propyl 2-formylbenzoate 2a

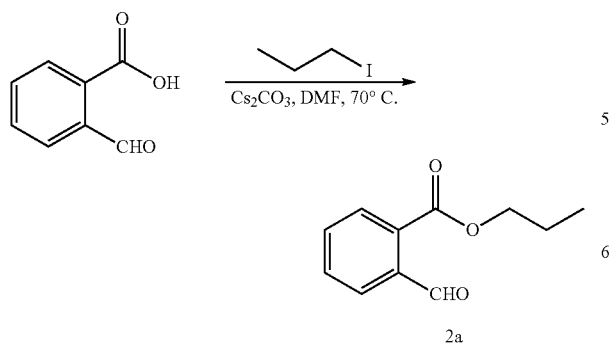

1.5 g of a transparent liquid (yield 78%) was obtained according to the same synthesis method as that for 1a. $^1$H NMR (400 MHz, DMSO-d$_6$, ppm): δ 10.40 (s, 1H), 7.93-

Isopropyl 2-formylbenzoate 3a

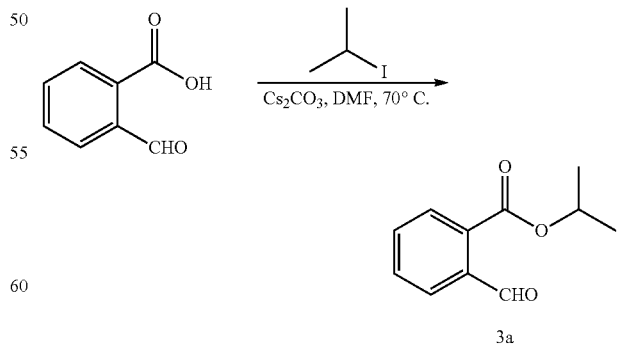

1.7 g of a yellow transparent liquid (yield 88%) was obtained according to the same synthesis method as that for 1a. $^1$H NMR (400 MHz, DMSO-d$_6$, ppm): δ 10.40 (s, 1H), 7.91-7.83 (m, 2H), 7.80-7.75 (m, 2H), 5.20 (hept, J=6.2 Hz, 1H), 1.35 (d, J=6.2 Hz, 6H). LC-MS (ESI) calcd for C$_{11}$H$_{12}$O$_3$ [M+H]$^+$ 193.08, found 193.10.

(E)-4-(2-chlorophenyl)-2-(2-isopropoxyformylbenzylidenehydrazino)thiazole A3

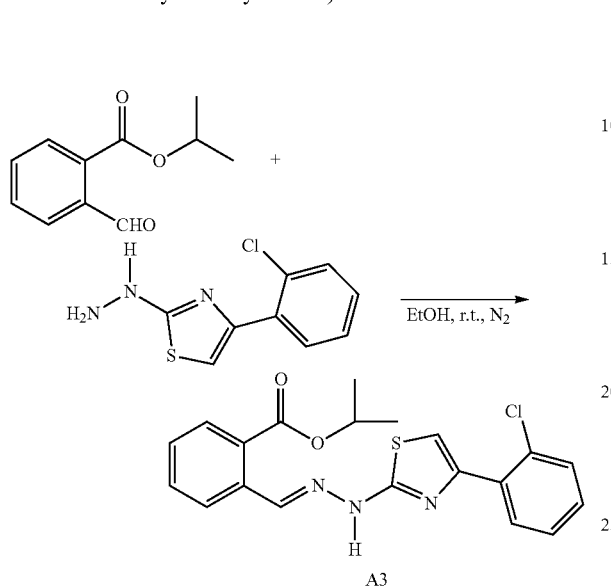

A3

200 mg of a brown solid powder (yield 60%) was obtained according to the same synthesis method as that for A1. $^1$H NMR (400 MHz, DMSO-d$_6$, ppm): δ 12.40 (s, 1H), 8.69 (s, 1H), 7.99 (d, J=7.8 Hz, 1H), 7.90-7.81 (m, 2H), 7.65 (t, J=7.6 Hz, 1H), 7.55-7.46 (m, 2H), 7.44-7.32 (m, 3H), 5.16 (hept, J=6.3 Hz, 1H), 1.35 (d, J=6.1 Hz, 6H). $^{13}$C NMR (100 MHz, DMSO-d$_6$, ppm): δ 205.55, 167.21, 166.04, 147.14, 139.59, 134.28, 133.20, 132.07, 131.02, 130.72, 130.35, 130.07, 129.35, 129.00, 128.84, 127.21, 126.11, 108.82, 68.85, 21.53. HRMS (ESI) calcd for C$_{20}$H$_{18}$ClN$_3$O$_2$S [M+H]$^+$ 400.0808, found 400.0868. HPLC purity: 97.35%, Retention time=10.44 min.

Butyl 2-formylbenzoate 4a

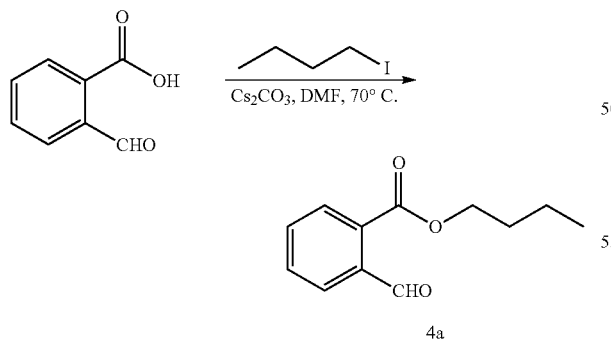

4a 1.7 g of a yellow transparent liquid (yield 86%) was obtained according to the same synthesis method as that for 1a. $^1$H NMR (400 MHz, DMSO-d$_6$, ppm): δ 10.41 (s, 1H), 7.93-7.90 (m, 1H), 7.88-7.85 (m, 1H), 7.81-7.77 (m, 2H), 4.33 (t, J=6.5 Hz, 2H), 1.71 (p, J=8.5, 6.6 Hz, 2H), 1.42 (h, 2H), 0.94 (t, J=7.4 Hz, 3H). LC-MS (ESI) calcd for C$_{12}$H$_{14}$O$_3$ [M+H]$^+$ 207.09, found 207.10.

(E)-4-(2-chlorophenyl)-2-(2-butoxyformylbenzylidenehydrazino)thiazole A4

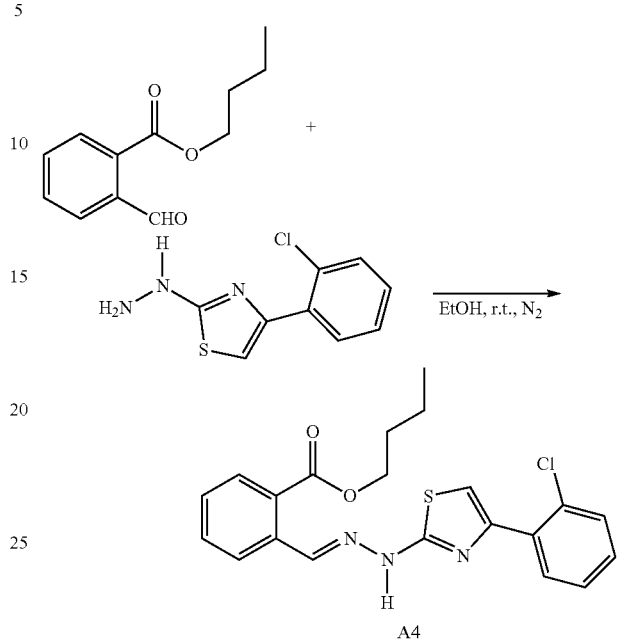

A4

210 mg of a yellow powder (yield 55%) was obtained according to the same synthesis method as that for A1. $^1$H NMR (400 MHz, DMSO-d$_6$, ppm): δ 12.40 (s, 1H), 8.71 (s, 1H), 8.00 (dd, J=8.0, 1.2 Hz, 1H), 7.89-7.84 (m, 2H), 7.67 (td, J=7.6, 1.3 Hz, 1H), 7.56-7.48 (m, 2H), 7.42 (td, J=7.5, 1.5 Hz, 1H), 7.39-7.33 (m, 2H), 4.30 (t, J=6.6 Hz, 2H), 1.72 (p, 2H), 1.42 (h, 2H), 0.94 (t, J=7.4 Hz, 3H). $^{13}$C NMR (100 MHz, DMSO-d$_6$, ppm): δ 167.68, 167.02, 147.63, 140.16, 134.95, 133.70, 132.70, 131.53, 131.22, 130.85, 130.58, 129.52, 129.40, 129.37, 127.73, 126.77, 109.35, 65.32, 30.57, 19.23, 14.09. HRMS (ESI) calcd for C$_{21}$H$_{20}$N$_3$O$_2$SCl [M+H]$^+$ 414.0965, found 414.1044. HPLC purity: 97.15%, Retention time=11.23 min.

2-butyl 2-formylbenzoate 5a

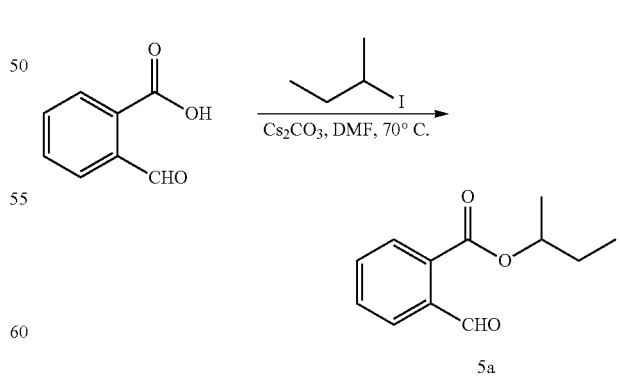

5a 1.8 g of a transparent liquid (yield 91%) was obtained according to the same synthesis method as that for 1a. $^1$H NMR (400 MHz, DMSO-d$_6$, ppm): δ 10.39 (s, 1H), 7.91-7.88 (m, 1H), 7.87-7.84 (m, 1H), 7.81-7.76 (m, 2H), 5.06 (q, J=6.2 Hz, 1H), 1.75-1.64 (m, 2H), 1.32 (d, J=6.3 Hz, 3H), 0.93 (t, J=7.4 Hz, 3H). LC-MS (ESI) calcd for $C_{12}H_{14}O_3$ [M+H]$^+$ 207.09, found 207.10.

(E)-4-(2-chlorophenyl)-2-(2-(2-butoxy)formylbenzylidenehydrazino)thiazole A5

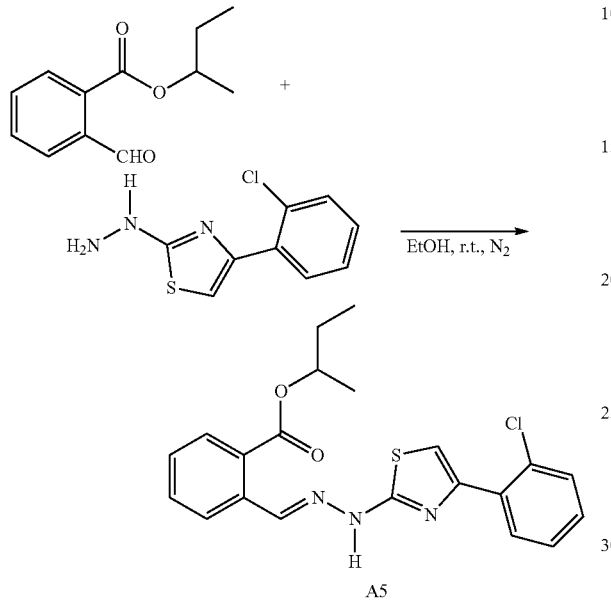

A5

150 mg of a pale yellow powder (yield 52%) was obtained according to the same synthesis method as that for A1. $^1$H NMR (400 MHz, DMSO-d$_6$, ppm): δ 12.41 (s, 1H), 8.71 (s, 1H), 8.00 (d, J=7.9, 1.2 Hz, 1H), 7.90-7.84 (m, 2H), 7.69-7.64 (m, 1H), 7.56-7.48 (m, 2H), 7.42 (td, J=7.5, 1.5 Hz, 1H), 7.39-7.33 (m, 2H), 5.03 (h, J=6.3 Hz, 1H), 1.77-1.63 (m, 2H), 1.33 (d, J=6.3 Hz, 3H), 0.93 (t, J=7.4 Hz, 3H). $^{13}$C NMR (100 MHz, DMSO-d$_6$, ppm): δ 167.71, 166.60, 147.64, 140.09, 134.89, 133.70, 132.64, 131.53, 131.22, 130.86, 130.52, 129.74, 129.52, 129.39, 127.73, 126.67, 109.35, 73.65, 28.66, 19.65, 10.07. HRMS (ESI) calcd for $C_{21}H_{20}N_3O_2SCl$ [M+H]$^+$ 414.0965, found 414.0988. HPLC purity: 98.05%, Retention time=11.14 min.

Amyl 2-formylbenzoate 6a

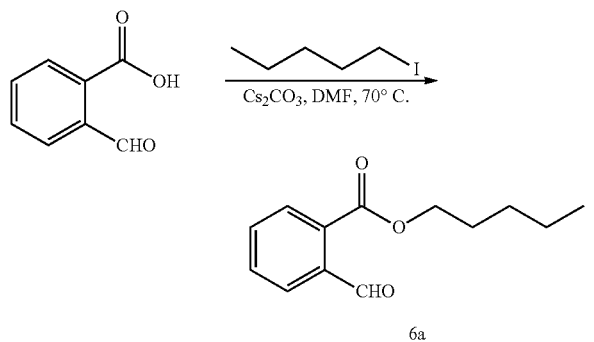

6a 1.6 g of a transparent liquid (yield 77%) was obtained according to the same synthesis method as that for 1a. $^1$H NMR (400 MHz, DMSO-d$_6$, ppm): δ 10.40 (s, 1H), 7.93-

7.89 (m, 1H), 7.88-7.84 (m, 1H), 7.81-7.77 (m, 2H), 4.32 (t, J=6.6 Hz, 2H), 1.72 (p, J=6.8 Hz, 2H), 1.42-1.30 (m, 4H), 0.92-0.87 (m, 3H). LC-MS (ESI) calcd for $C_{13}H_{16}O_3$ [M+H]$^+$ 221.11, found 221.10.

(E)-4-(2-chlorophenyl)-2-(2-pentyloxyformylbenzylidenehydrazino)thiazole A6

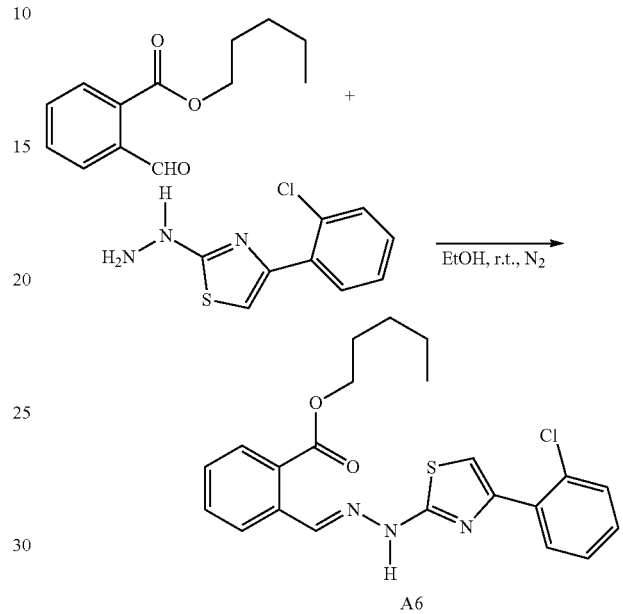

A6

120 mg of a yellow powder (yield 52%) was obtained according to the same synthesis method as that for A1. $^1$H NMR (400 MHz, DMSO-d$_6$, ppm): δ 12.39 (s, 1H), 8.71 (s, 1H), 7.99 (dd, J=8.0, 1.2 Hz, 1H), 7.86 (ddd, J=7.8, 6.1, 1.6 Hz, 2H), 7.66 (td, J=7.7, 1.4 Hz, 1H), 7.55-7.48 (m, 2H), 7.42 (td, J=7.5, 1.5 Hz, 1H), 7.38-7.33 (m, 2H), 4.29 (t, J=6.7 Hz, 2H), 1.74 (p, J=6.8 Hz, 2H), 1.42-1.30 (m, 4H), 0.89 (t, J=7.0 Hz, 3H). $^{13}$C NMR (100 MHz, DMSO-d$_6$, ppm): δ 167.68, 167.02, 147.63, 140.19, 134.95, 133.70, 132.69, 131.52, 131.22, 130.85, 130.57, 129.52, 129.40, 129.38, 127.73, 126.80, 109.33, 65.60, 28.21, 28.14, 22.29, 14.34. HRMS (ESI) calcd for $C_{22}H_{22}N_3O_2SCl$ [M+H]$^+$ 428.1121, found 428.1201. HPLC purity: 97.55%, Retention time=9.44 min.

Hexyl 2-formylbenzoate 7a

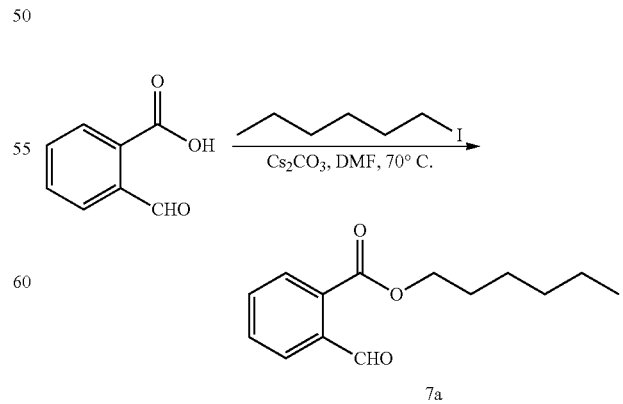

7a 1.9 g of a transparent liquid (yield 81%) was obtained according to the same synthesis method as that for 1a. $^1$H NMR (400 MHz, DMSO-$d_6$, ppm): δ 10.40 (s, 1H), 7.93-7.88 (m, 1H), 7.88-7.83 (m, 1H), 7.82-7.76 (m, 2H), 4.32 (t, J=6.6 Hz, 2H), 1.71 (p, 2H), 1.43-1.25 (m, 6H), 0.90-0.83 (m, 3H). LC-MS (ESI) calcd for $C_{14}H_{18}O_3$ [M+H]$^+$ 235.13, found 235.10.

(E)-4-(2-chlorophenyl)-2-(2-hexyloxyformylbenzylidenehydrazino)thiazole A7

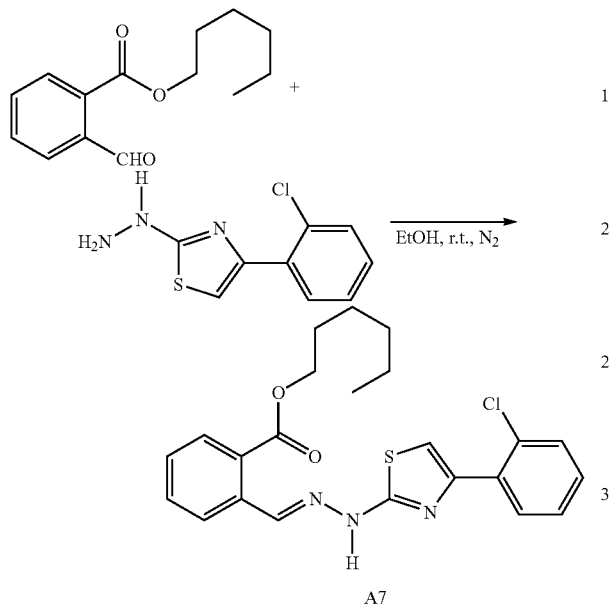

A7

110 mg of a pale yellow powder (yield 59%) was obtained according to the same synthesis method as that for A1. $^1$H NMR (400 MHz, DMSO-$d_6$, ppm): δ 12.45 (s, 1H), 8.76 (s, 1H), 8.05 (d, J=8.0 Hz, 1H), 7.96-7.87 (m, 2H), 7.72 (t, J=7.7 Hz, 1H), 7.62-7.53 (m, 2H), 7.51-7.37 (m, 3H), 4.34 (t, J=6.6 Hz, 2H), 1.79 (t, J=7.4 Hz, 2H), 1.49-1.28 (m, 6H), 0.92 (t, J=6.7 Hz, 3H). $^{13}$C NMR (100 MHz, DMSO-$d_6$, ppm): 167.56, 166.92, 147.53, 140.10, 134.85, 133.60, 132.56, 131.41, 131.12, 130.74, 130.44, 129.39, 129.30, 129.27, 127.60, 126.71, 109.20, 65.51, 31.27, 28.36, 25.52, 22.36, 14.22. HRMS (ESI) calcd for $C_{23}H_{24}N_3O_2SCl$ [M+H]$^+$ 442.1278, found 442.1355. HPLC purity: 98.60%, Retention time=13.41 min.

Cyclohexyl 2-formylbenzoate 8a 1.8 g of a pale yellow transparent liquid (yield 77%) was obtained according to the same synthesis method as that for 1a. $^1$H NMR (400 MHz, DMSO-$d_6$, ppm): δ 10.41 (s, 1H), 7.93-7.88 (m, 1H), 7.87-7.82 (m, 1H), 7.81-7.75 (m, 2H), 5.05-4.95 (m, 1H), 1.97-1.88 (m, 2H), 1.76-1.66 (m, 2H), 1.61-1.47 (m, 3H), 1.47-1.36 (m, 2H), 1.36-1.25 (m, 1H). LC-MS (ESI) calcd for $C_{14}H_{16}O_3$ [M+H]$^+$ 233.11, found 233.10.

(E)-4-(2-chlorophenyl)-2-(2-cyclohexyloxyformylbenzylidenehydrazino)thiazole A8

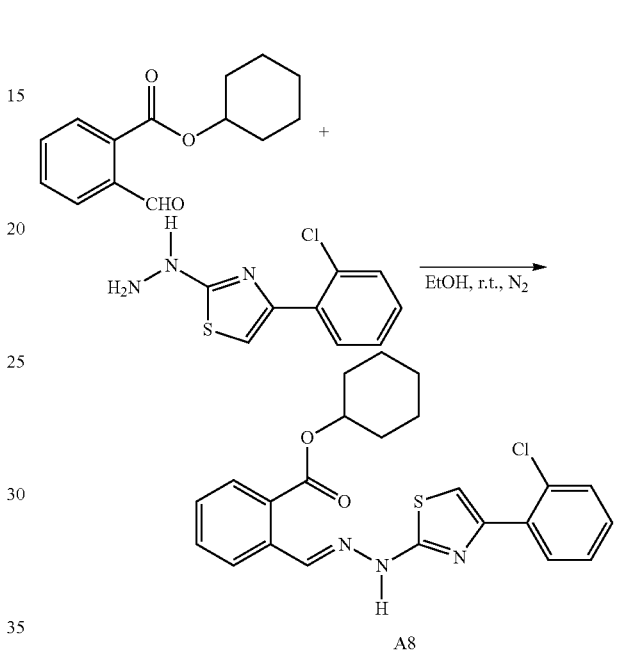

A8

130 mg of a yellow powder (yield 50%) was obtained according to the same synthesis method as that for A1. $^1$H NMR (400 MHz, DMSO-$d_6$, ppm): δ 12.42 (s, 1H), 8.70 (s, 1H), 8.00 (d, J=7.8 Hz, 1H), 7.90-7.83 (m, 2H), 7.66 (t, J=7.4 Hz, 1H), 7.56-7.47 (m, 2H), 7.42 (td, J=7.5, 1.2 Hz, 1H), 7.39-7.33 (m, 2H), 5.00-4.91 (m, 1H), 1.98-1.89 (m, 2H), 1.78-1.68 (m, 2H), 1.64-1.49 (m, 3H), 1.47-1.25 (m, 3H). $^{13}$C NMR (100 MHz, DMSO-$d_6$, ppm): δ 167.72, 166.37, 140.10, 134.84, 132.62, 131.52, 131.22, 130.86, 130.60, 129.80, 129.52, 129.39, 127.73, 126.67, 109.34, 73.85, 31.44, 25.34, 23.69. HRMS (ESI) calcd for $C_{23}H_{22}N_3O_2SCl$ [M+H]$^+$ 440.1121, found 440.1101. HPLC purity: 98.03%, Retention time=13.03 min.

(Pivaloyloxy)methyl 2-formylbenzoate 9a

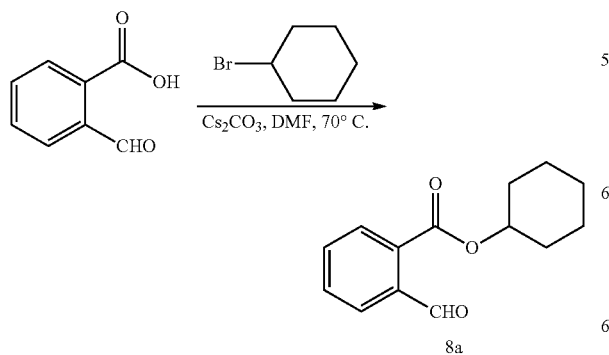

8a

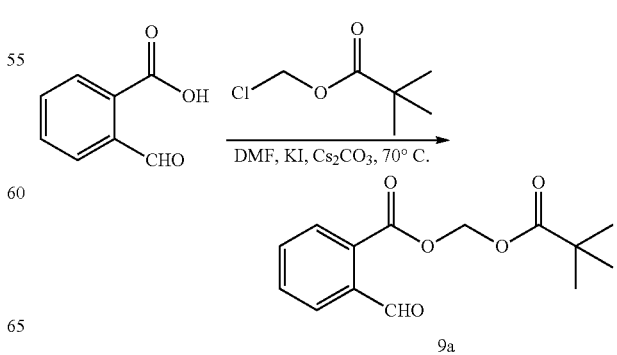

9a

O-carboxybenzaldehyde (1 g, 6.7 mmol) was weighed into a 100 mL three-necked flask, cesium carbonate (4.3 g, 13.3 mmol), potassium iodide (1.1 g, 6.7 mmol) and 15 mL of N,N-dimethylformamide (DMF) were added, and chloromethyl pivalate (1.5 g, 10 mmol) was added under stirring. The reaction mixture was heated to 70° C. for 20 h. The reaction was monitored by TLC until the reaction was completed. The heating was stopped and 20 mL of water was added into the reaction flask. The reaction solution was extracted for three times with dichloromethane and water, and the organic layers were combined, dried over anhydrous sodium sulfate, and suction-filtered. The filtrate was purified through a silica-gel column to obtain a clear transparent liquid (0.9 g, yield 52%).

(Pivaloyloxy)methyl (E)-2-((2-(4-(2-chlorophenyl)thiazol-2-yl)hydrazono)methyl)benzoate A9

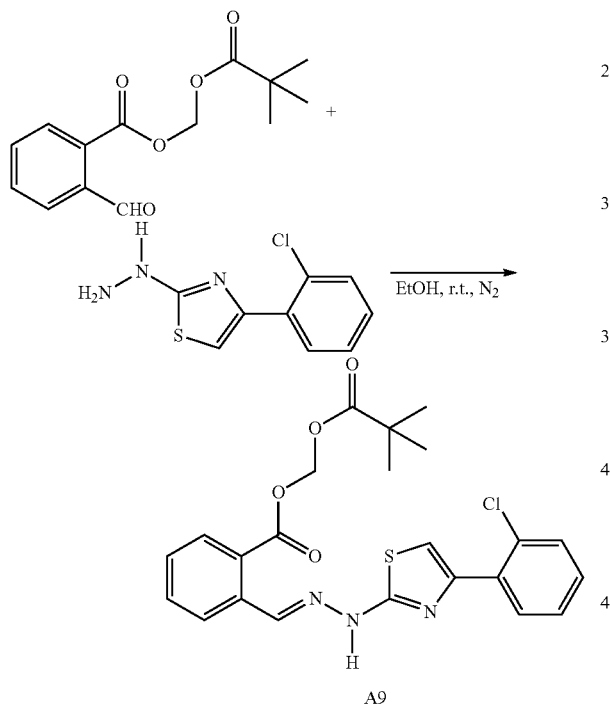

A crude product was obtained according to the same synthesis method as that for A1. Afterwards, a pale yellow powder was obtained through solid precipitation by adding another solvent (the crude product was completely dissolved in an appropriate amount of ethyl acetate, petroleum ether was added with electromagnetic-stirring and rapidly stirred, and solids were precipitated and suction-filtered) (180 mg, yield 49%). $^1$H NMR (400 MHz, DMSO-$d_6$, ppm): δ 12.43 (s, 1H), 8.73 (s, 1H), 8.03 (d, J=8.0, 1.2 Hz, 1H), 7.89-7.83 (m, 2H), 7.74-7.68 (m, 1H), 7.56-7.51 (m, 2H), 7.42 (td, J=7.5, 1.4 Hz, 1H), 7.39-7.33 (m, 2H), 5.98 (s, 2H), 1.18 (s, 9H). $^{13}$C NMR (100 MHz, DMSO-$d_6$, ppm): δ 167.13, 164.91, 139.23, 135.19, 133.04, 131.04, 130.73, 130.35, 130.31, 129.04, 129.02, 127.24, 127.06, 126.51, 108.96, 80.13, 38.26, 26.47. HRMS (ESI) calcd for C23H22N3O4SCl [M+H]$^+$ 472.1020, found 472.1096. HPLC purity: 97.79%, Retention time=9.68 min.

((isopropoxycarbonyl)oxy)methyl 2-formylbenzoate 10a

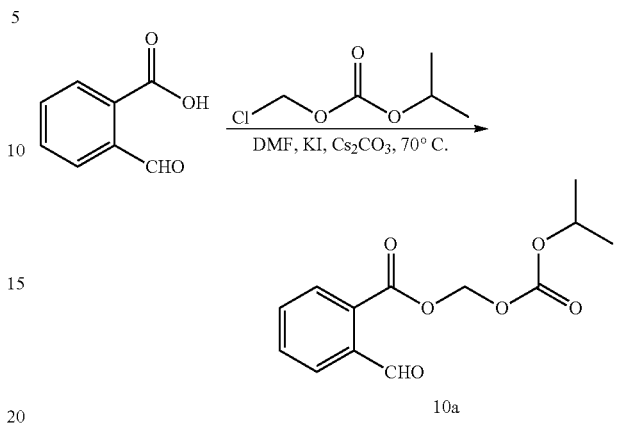

0.8 g of a colorless transparent liquid (yield 45%) was obtained according to the same synthesis method as that for 9a. LC-MS (ESI) calcd for $C_{13}H_{14}O_6$ [M+NH$_4$]$^+$ 284.08, found 284.10.

((isopropoxycarbonyl)oxy)methyl (E)-2-((2-(4-(2-chlorophenyl)thiazol-2-yl)hydrazono)methyl)benzoate A10

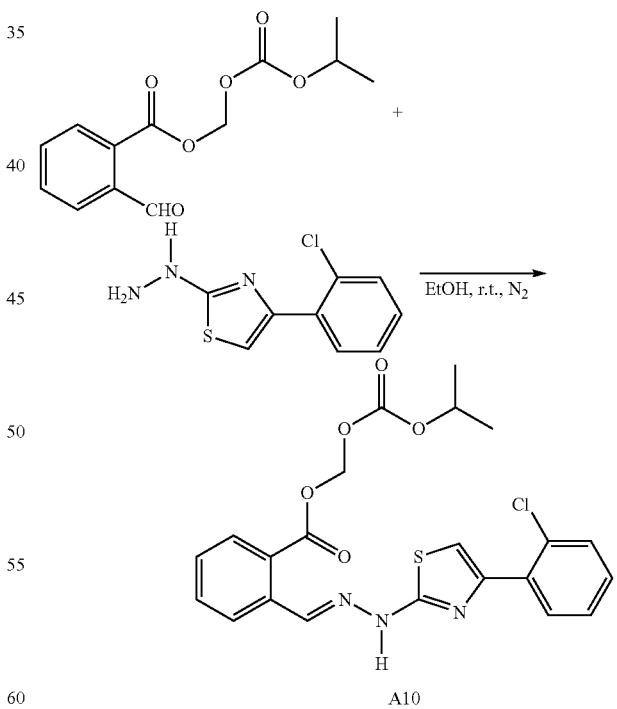

160 mg of a yellow powder (yield 53%) was obtained according to the same synthesis method as that for A9. $^1$H NMR (400 MHz, DMSO-$d_6$, ppm): δ 12.44 (s, 1H), 8.76 (s, 1H), 8.04 (d, J=8.0, 1.2 Hz, 1H), 7.93-7.85 (m, 2H), 7.73 (t, J=7.6, 1.3 Hz, 1H), 7.57-7.51 (m, 2H), 7.43 (td, J=7.5, 1.5

Hz, 1H), 7.40-7.33 (m, 2H), 5.96 (s, 2H), 4.85 (hept, J=6.2 Hz, 1H), 1.26 (d, J=6.2 Hz, 6H). $^{13}$C NMR (100 MHz, DMSO-d$_6$, ppm): δ 167.62, 165.32, 153.25, 147.67, 139.76, 135.83, 133.66, 131.54, 131.23, 131.01, 130.85, 129.54, 129.49, 127.74, 127.30, 126.99, 109.47, 83.02, 73.24, 21.80. HRMS (ESI) calcd for C$_{22}$H$_{20}$N$_3$O$_5$SCl [M+H]$^+$ 474.0812, found 474.0889. HPLC purity: 99.25%, Retention time=12.74 min.

Benzoyl 2-formylbenzoate 11a

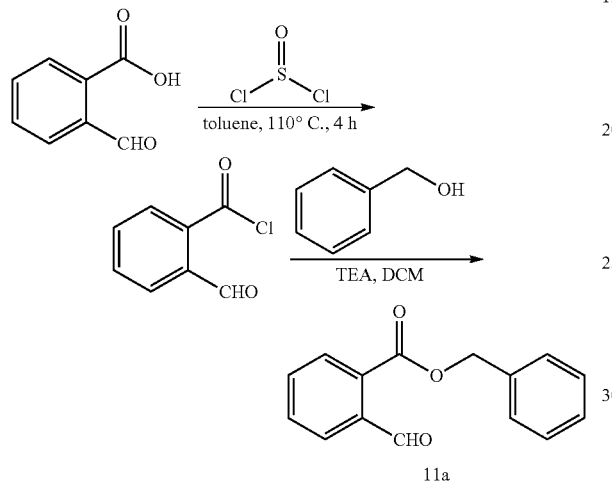

o-carboxybenzaldehyde (1.5 g, 10 mmol) was weighed into a 100 mL three-necked flask B, and 20 mL of anhydrous toluene was added. In an ice bath, thionyl chloride (1.79 g, 15 mmol) was added with electromagnetic-stirring. After 15 minutes, the ice bath was removed, and the three-necked flask B was transferred to an oil bath and heat to reflux at 110° C. for 4 h. The heating was stopped, and the solvent was removed in vacuo to obtain a yellow viscous liquid, which was directly diluted with 10 mL of anhydrous dichloromethane. Benzyl alcohol (1.08 g, 10 mmol), triethylamine (1.52 g, 15 mmol), 15 mL of anhydrous dichloromethane were added into another 100 mL single-mouth reaction flask A and electromagnetic-stirred in an ice salt bath for 15 minutes. An acid chloride solution in dichloromethane was added dropwise to the single-mouth reaction flask A for 30 minutes in an ice bath. Afterwards, the reaction system was warmed to room temperature, and the reaction was detected by TLC. After the reaction was completed, water was added to the reaction solution and stirred for 10 minutes, and the mixture was allowed to stratification. The organic phase was taken, and the aqueous phase was extracted for three times with dichloromethane. Organic phases were combined, dried, evaporated to dryness, and purified through a column, so as to give a colorless transparent liquid (1.1 g, yield 46%). $^1$H NMR (400 MHz, DMSO-d$_6$, ppm): δ 10.42 (s, 1H), 7.95-7.91 (m, 2H), 7.78-7.75 (m, 2H), 7.50-7.48 (m, 2H), 7.42-7.36 (m, 3H), 5.39 (s, 2H). LC-MS (ESI) calcd for C$_{15}$H$_{12}$O$_3$ [M+H]$^+$ 241.08, found 241.10.

(E)-4-(2-chlorophenyl)-2-(2-benzyloxyformylbenzylidenehydrazino)thiazole A11

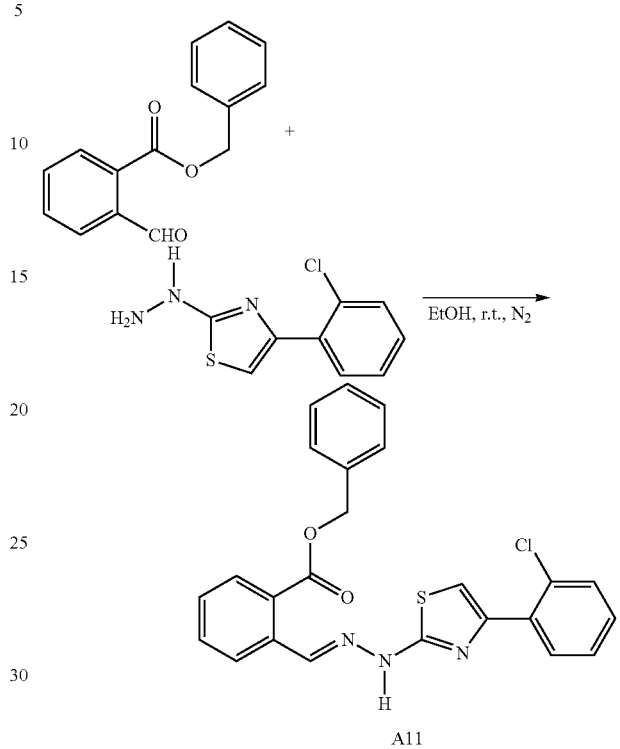

80 mg of a brown powder (yield 46%) was obtained according to the same synthesis method as that for A1. $^1$H NMR (400 MHz, DMSO-d$_6$, ppm): δ 12.41 (s, 1H), 8.78 (s, 1H), 8.02 (d, J=7.9 Hz, 1H), 7.92-7.86 (m, 2H), 7.70-7.65 (m, 1H), 7.56-7.49 (m, 4H), 7.45-7.40 (m, 3H), 7.39-7.34 (m, 3H), 5.38 (s, 2H). $^{13}$C NMR (100 MHz, DMSO-d$_6$, ppm): δ 166.20, 147.14, 139.61, 135.86, 134.72, 133.20, 132.41, 131.04, 130.73, 130.35, 130.21, 129.01, 128.92, 128.51, 128.37, 128.16, 128.08, 127.22, 126.35, 108.87, 66.59. HRMS (ESI) calcd for C$_{24}$H$_{18}$N$_3$O$_2$SCl [M+H]$^+$ 448.0808, found 448.0888. HPLC purity: 98.45%, Retention time=12.14 min.

Phenylethyl 2-formylbenzoate 12a

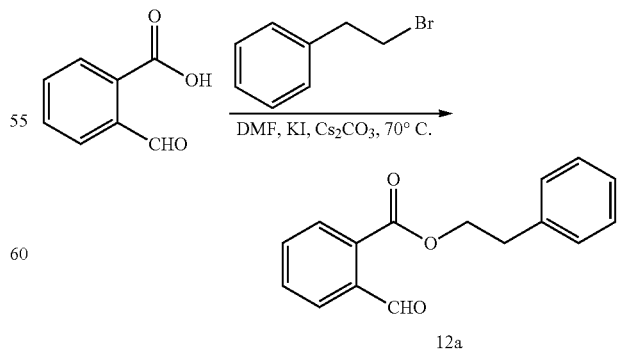

2.5 g of a transparent liquid (yield 70%) was obtained according to the same synthesis method as that for 9a. $^1$H NMR (400 MHz, DMSO-d$_6$, ppm): δ 10.31 (s, 1H), 7.86-7.81 (m, 2H), 7.79-7.74 (m, 2H), 7.32 (d, J=4.4 Hz, 4H), 7.27-7.20 (m, 1H), 4.56 (t, J=6.7 Hz, 2H), 3.06 (t, J=6.7 Hz, 2H). LC-MS (ESI) calcd for C$_{16}$H$_{14}$O$_3$ [M+H]$^+$ 255.09, found 255.10.

(E)-4-(2-chlorophenyl)-2-(2-phenylethoxyformyl-benzylidenehydrazino)thiazole A12

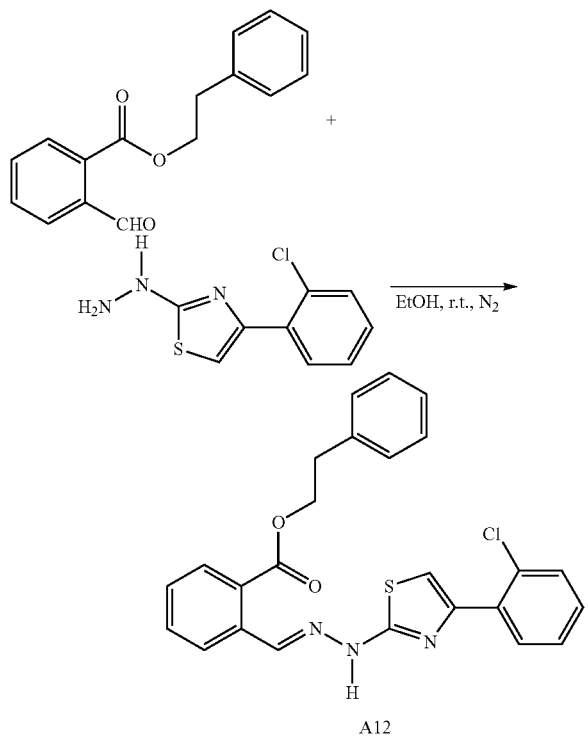

110 mg of a yellow powder (yield 51%) was obtained according to the same synthesis method as that for A1. $^1$H NMR (400 MHz, DMSO-d$_6$, ppm): δ 12.46 (s, 1H), 8.79 (s, 1H), 8.05 (d, J=7.9 Hz, 1H), 7.94 (d, J=7.7 Hz, 1H), 7.84 (d, J=7.8 Hz, 1H), 7.71 (t, J=7.7 Hz, 1H), 7.60 (d, J=7.9 Hz, 1H), 7.54 (t, J=7.6 Hz, 1H), 7.48 (t, J=7.6 Hz, 1H), 7.46-7.34 (m, 6H), 7.32-7.25 (m, 1H), 4.57 (t, J=6.8 Hz, 2H), 3.14 (t, J=6.9 Hz, 2H). $^{13}$C NMR (100 MHz, DMSO-d$_6$, ppm): δ 167.58, 166.74, 147.55, 140.03, 138.30, 134.93, 133.61, 132.66, 131.43, 131.13, 130.75, 130.45, 129.41, 129.24, 129.03, 128.78, 127.62, 126.80, 126.67, 109.25, 65.98, 34.61. HRMS (ESI) calcd for C$_{25}$H$_{20}$N$_3$O$_2$SCl [M+H]$^+$ 462.0965, found 462.1041. HPLC purity: 98.60%, Retention time=12.24 min.

2-formylbenzoyl(N,N-dimethyl)amine 13a

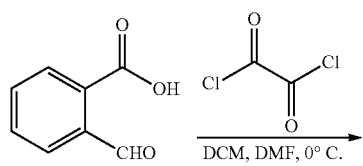

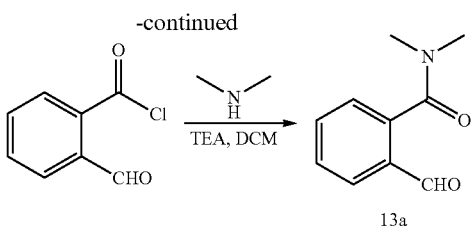

o-carboxybenzaldehyde (1.5 g, 10 mmol) was weighed into a 100 mL three-necked flask, and 30 mL of anhydrous dichloromethane was added. 4 drops of anhydrous DMF were added into the flask in an ice salt bath. Thionyl chloride (1.9 g, 15 mmol) was added with electromagnetic-stirring. After 30 minutes, the ice bath was removed, and the flask was warmed to room temperature for 2 h, and the reaction was detected by TLC. After the reaction was completed, the solvent was removed in vacuo to obtain a yellow viscous liquid, which was directly diluted with 10 mL of anhydrous dichloromethane. Dimethylamine (0.45 g, 10 mmol), triethylamine (1.52 g, 15 mmol), 10 mL of anhydrous dichloromethane were added into another 100 mL single-mouth reaction flask and electromagnetic-stirred in an ice salt bath for 15 minutes. A freshly prepared acid chloride solution in dichloromethane was added dropwise through a constant pressure dropping funnel into the reaction flask for 30 minutes in an ice bath. Afterwards, the reaction system was warmed to room temperature, and the reaction was detected by TLC. After the reaction was completed, water was added to the reaction solution and stirred for 10 minutes, and the mixture was allowed to stratification. The organic phase was taken, and the aqueous phase was extracted for three times with dichloromethane. Organic phases were combined, dried, evaporated to dryness, and purified through a column, so as to give a colorless transparent liquid (0.5 g, yield 26%). $^1$H NMR (400 MHz, DMSO-d$_6$, ppm): δ 9.97 (s, 1H), 7.98-7.94 (m, 1H), 7.75 (td, J=7.5, 1.4 Hz, 1H), 7.67-7.61 (m, 1H), 7.44-7.39 (m, 1H), 3.03 (s, 3H), 2.72 (s, 3H). LC-MS (ESI) calcd for C$_{10}$H$_{11}$NO$_2$ [M+H]$^+$ 178.08, found 178.10.

(E)-4-(2-chlorophenyl)-2-((N,N-Dimethyl)formyl-benzylidenehydrazino)thiazole A13

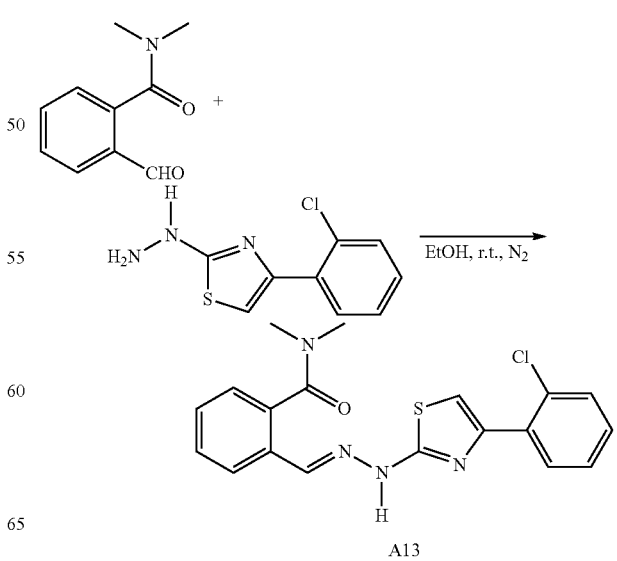

80 mg of a yellow powder (yield 31%) was obtained according to the same synthesis method as that for A1. $^1$H NMR (400 MHz, DMSO-d$_6$, ppm): δ 12.25 (s, 1H), 8.07 (s, 1H), 7.94-7.89 (m, 2H), 7.61-7.58 (m, 1H), 7.57-7.53 (m, 1H), 7.52-7.46 (m, 2H), 7.44-7.40 (m, 2H), 7.37-7.32 (m, 1H), 3.13 (s, 3H), 2.85 (s, 3H). $^{13}$C NMR (100 MHz, DMSO-d$_6$, ppm): δ 169.33, 167.36, 147.51, 139.24, 136.34, 133.59, 131.42, 131.12, 130.92, 130.74, 129.47, 129.41, 129.32, 127.61, 127.19, 126.02, 109.19, 38.50, 34.64. HRMS (ESI) calcd for C$_{19}$H$_{17}$N$_4$OSCl [M+H]$^+$ 385.0812, found 385.0802. HPLC purity: 98.25%, Retention time=11.45 min.

2-methylthiosemicarbazide 4

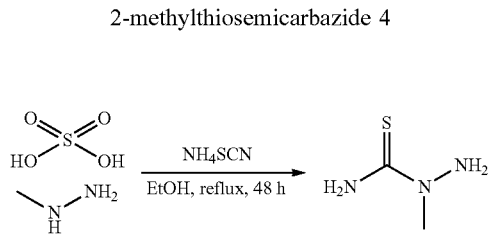

Methyl hydrazine sulfate (12.5 g, 86.5 mmol) was weighed into a 500 ml three-mouth flask, 350 ml of anhydrous ethanol was added, and ammonium thiocyanate (8 g, 104.0 mmol) of was added with electromagnetic-stirring. The reaction mixture was heated to reflux, and detected by TLC for 48 h. The reaction was stopped, cooled to room temperature and suction-filtered. The obtained filtrate was evaporated to dryness and separated through silica gel column chromatography (DCM:MeOH=100:1 v/v) to give white powdery solids (2.2 g, yield 24%). $^1$H NMR (400 MHz, DMSO-d$_6$, ppm): δ 7.38 (s, 2H), 4.88 (s, 2H), 3.40 (s, 3H). LC-MS (ESI) calcd for C$_2$H$_7$N$_3$S [M+H]$^+$ 106.04, found 106.10.

2-methyl-1-(2-carboxybenzylidene)thiosemicarbazide 5

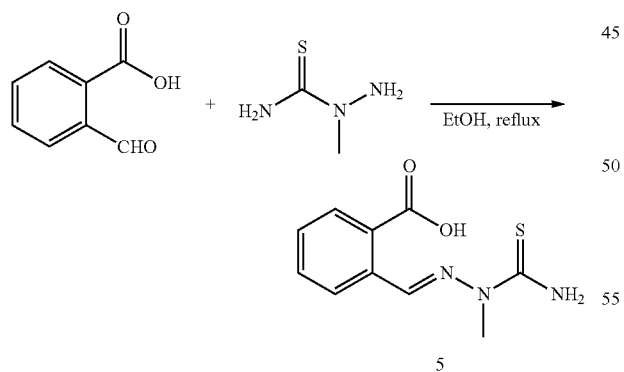

Compound 4 (600 mg, 5.7 mmol) was weighed into a 250 mL three-necked flask, 150 mL of absolute ethanol was added, o-formylbenzoic acid (855 mg, 5.7 mmol) was added with electromagnetic-stirring, heated to reflux, and the reaction was monitored by TLC. After 4 h, the reaction was completed, the heating was stopped, and the reaction solution was cooled to room temperature. The solvent was evaporated to dryness in vacuo and purified through silica gel column chromatography (DCM:MeOH=100:1, v/v) to obtain white powdery solids (700 mg, yield 51.9%). $^1$H NMR (400 MHz, DMSO-d$_6$, ppm): δ 13.32 (br, 1H), 8.54 (s, 1H), 8.50 (s, 1H), 8.33 (d, J=7.6 Hz, 1H), 8.24 (s, 1H), 7.90 (d, J=7.8 Hz, 1H), 7.60 (t, J=7.2 Hz, 1H), 7.52 (t, J=7.2 Hz, 1H), 3.75 (s, 3H). LC-MS (ESI) calcd for C$_2$H$_7$N$_3$S [M+H]$^+$ 238.06, found 238.10.

(E)-4-(2-chlorophenyl)-2-[1-methyl-2-(2-carboxybenzylidene)hydrazino]thiazole B

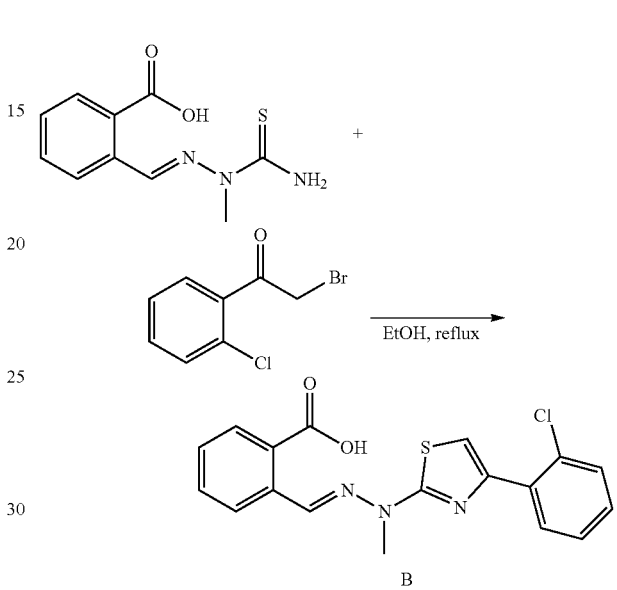

Compound 5 (700 mg, 2.94 mmol) was weighed into a 250 mL three-necked flask, 80 mL of absolute ethanol was added, and 2-bromo-2'-chloroacetophenone (0.46 mL, 2.94 mmol) was added with electromagnetic-stirring, and heated to reflux. The reaction was detected by TLC. After 4 h, the reaction was completed. The heating was stopped and the reaction mixture was cooled to room temperature. The solvent was evaporated to dryness in vacuo and purified through silica gel column chromatography (DCM: MeOH=100:1, v/v) to give 540 mg of yellow powdery solids (yield 49%). Mp 210.2-210.8° C., $^1$H NMR (400 MHz, DMSO-d$_6$, ppm): δ 13.26 (s, 1H), 8.60 (s, 1H), 8.04 (d, J=7.6 Hz, 1H), 7.97-7.89 (m, 2H), 7.64 (t, J=7.8 Hz, 1H), 7.55-7.48 (m, 2H), 7.46 (s, 1H), 7.40 (td, J$_1$=7.6 Hz, J$_2$=1.2 Hz, 1H), 7.32 (td, J$_1$=7.6 Hz, J$_2$=1.6 Hz, 1H), 3.65 (s, 3H). $^{13}$C NMR (100 MHz, DMSO-d$_6$, ppm): δ 168.96, 168.50, 147.22, 136.91, 135.21, 133.40, 132.46, 131.50, 131.02, 130.88, 130.55, 130.14, 129.46, 129.18, 127.62, 126.50, 111.43, 32.90. HRMS (ESI) calcd for C$_{18}$H$_{15}$ClN$_3$O$_2$S [M+H]$^+$ 372.0574, found 372.0573. HPLC purity: 98.15%, Retention time=9.46 min.

(E)-4-(2-chlorophenyl)-2-[1-methyl-2-(2-ethoxyformylbenzylidene)hydrazino]thiazole B1

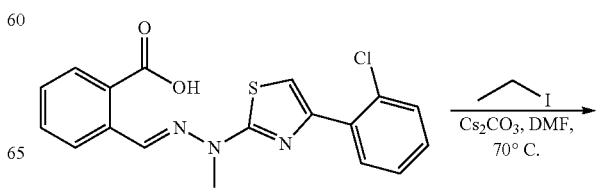

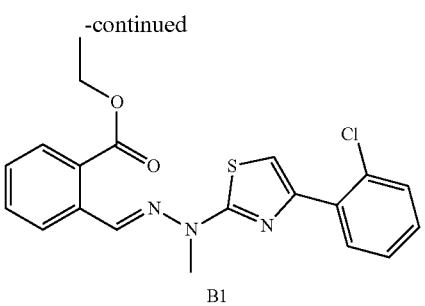

B1

Compound B (0.2 g, 0.54 mmol) was weighed into a 50 mL two-necked flask, cesium carbonate (0.35 g, 1.08 mmol) and 10 mL of N,N-dimethylformamide (DMF) were added, and iodoethane (0.18 g, 1.08 mmol) was added with electromagnetic-stirring. The reaction was heated to 70° C., and detected by TLC during the reaction. After 5 hr, the reaction was completed. The heating was stopped, and 20 mL of water was added to the reaction flask. The reaction solution was extracted with dichloromethane (DCM), and allowed to stand for separating the organic phase. The aqueous phase was extracted for three times with dichloromethane. Organic phases were combined and dried. The solvent was evaporated to dryness in vacuo and purified through column chromatography to give yellow powdery solids (120 mg, yield 58%). $^1$H NMR (400 MHz, DMSO-$d_6$, ppm): δ 8.49 (s, 1H), 8.02 (d, J=8.1, 1.2 Hz, 1H), 7.96 (dd, J=7.7, 1.8 Hz, 1H), 7.92-7.88 (m, 1H), 7.69 (t, J=7.6, 1.4 Hz, 1H), 7.56-7.47 (m, 3H), 7.45-7.40 (m, 1H), 7.37 (td, J=7.6, 1.8 Hz, 1H), 4.36 (q, J=7.1 Hz, 2H), 3.69 (s, 3H), 1.35 (t, J=7.1 Hz, 3H). $^{13}$C NMR (100 MHz, DMSO-$d_6$, ppm): δ 168.51, 166.58, 146.72, 136.19, 134.55, 133.00, 132.32, 131.12, 130.69, 130.36, 130.36, 129.08, 129.06, 128.88, 127.25, 126.36, 111.10, 61.16, 32.55, 14.04. HRMS (ESI) calcd for $C_{20}H_{18}N_3O_2SCl$ [M+H]$^+$ 400.0808, found 400.0886. HPLC purity: 98.65%, Retention time=16.44 min.

(E)-4-(2-chlorophenyl)-2-[1-methyl-2-(2-propoxyformylbenzylidene)hydrazino]thiazole B2

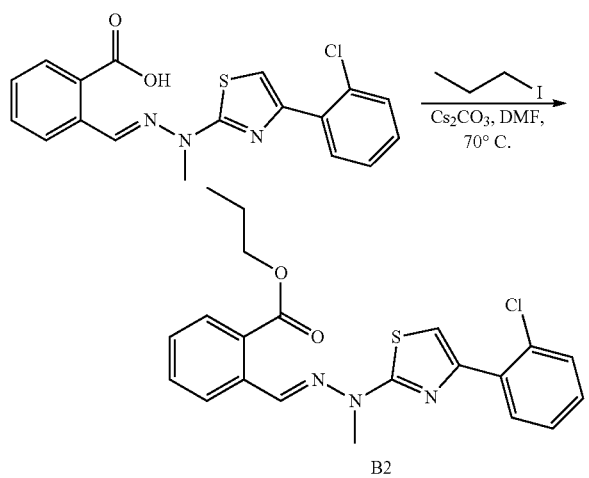

B2

100 mg of yellow powdery solids (yield 51%) was obtained according to the same synthesis method as that for B1. $^1$H NMR (400 MHz, DMSO-$d_6$, ppm): δ 8.49 (s, 1H), 8.02 (d, J=8.0, 1.2 Hz, 1H), 7.96 (dd, J=7.7, 1.9 Hz, 1H), 7.91 (dd, J=7.9, 1.4 Hz, 1H), 7.72-7.67 (m, 1H), 7.57-7.46 (m, 3H), 7.43 (td, J=7.5, 1.4 Hz, 1H), 7.37 (td, J=7.6, 1.8 Hz, 1H), 4.27 (t, J=6.6 Hz, 2H), 3.68 (s, 3H), 1.75 (h, J=7.1 Hz, 2H), 0.98 (t, J=7.4 Hz, 3H). $^{13}$C NMR (100 MHz, DMSO-$d_6$, ppm): δ 169.00, 167.14, 147.22, 136.65, 135.11, 133.49, 132.84, 131.62, 131.19, 130.87, 130.81, 129.59, 129.53, 129.42, 127.76, 126.94, 111.61, 67.09, 33.05, 21.99, 10.89. HRMS (ESI) calcd for $C_{21}H_{20}N_3O_2SCl$ [M+H]$^+$ 414.0965, found 414.1042. HPLC purity: 99.75%, Retention time=15.44 min.

(E)-4-(2-chlorophenyl)-2-[1-methyl-2-(2-isopropoxyformylbenzylidene)hydrazino]thiazole B3

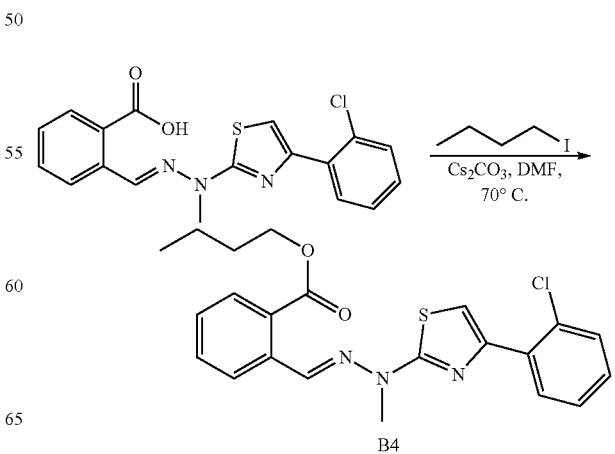

B3

140 mg of pale yellow powder (yield 57%) was obtained according to the same synthesis method as that for B1. $^1$H NMR (400 MHz, DMSO-$d_6$, ppm): δ 8.48 (s, 1H), 8.02 (d, J=8.0, 1.2 Hz, 1H), 7.96 (dd, J=7.7, 1.8 Hz, 1H), 7.88 (d, J=7.8, 1.4 Hz, 1H), 7.71-7.65 (m, 1H), 7.56-7.47 (m, 3H), 7.46-7.39 (m, 1H), 7.36 (td, J=7.6, 1.8 Hz, 1H), 5.21 (hept, J=6.3 Hz, 1H), 3.69 (s, 3H), 1.36 (d, J=6.2 Hz, 6H). $^{13}$C NMR (100 MHz, DMSO-$d_6$, ppm): δ 168.52, 166.09, 146.73, 136.11, 134.45, 133.01, 132.24, 131.12, 130.70, 130.36, 129.43, 129.08, 128.87, 127.25, 126.27, 111.10, 68.75, 32.54, 21.59. HRMS (ESI) calcd for $C_{21}H_{20}N_3O_2SCl$ [M+H]$^+$ 414.0965, found 414.0955. HPLC purity: 99.65%, Retention time=12.44 min.

(E)-4-(2-chlorophenyl)-2-[1-methyl-2-(2-butoxyformylbenzylidene)hydrazino]thiazole B4

B4

190 mg of yellow powdery solids (yield 61%) was obtained according to the same synthesis method as that for B1. ¹H NMR (400 MHz, DMSO-d₆, ppm): δ 8.49 (s, 1H), 8.01 (d, J=7.9, 1.2 Hz, 1H), 7.96 (dd, J=7.7, 1.8 Hz, 1H), 7.90 (dd, J=7.8, 1.3 Hz, 1H), 7.72-7.66 (m, 1H), 7.56-7.46 (m, 3H), 7.43 (td, J=7.5, 1.4 Hz, 1H), 7.36 (td, J=7.6, 1.9 Hz, 1H), 4.31 (t, J=6.6 Hz, 2H), 3.68 (s, 3H), 1.71 (p, 2H), 1.42 (h, 2H), 0.93 (t, J=7.4 Hz, 3H). ¹³C NMR (100 MHz, DMSO-d₆, ppm): δ 168.98, 167.14, 147.21, 136.62, 135.11, 133.49, 132.81, 131.62, 131.18, 130.86, 130.80, 129.58, 129.50, 129.40, 127.75, 126.95, 111.60, 65.33, 33.03, 30.60, 19.26, 14.06. HRMS (ESI) calcd for C$_{22}$H$_{22}$N$_3$O$_2$SCl [M+H]$^+$ 428.1121, found 428.1131. HPLC purity: 98.65%, Retention time=20.44 min.

(E)-4-(2-chlorophenyl)-2-[1-methyl-2-(2-(2-butoxy)formylbenzylidene)hydrazino]thiazole B5

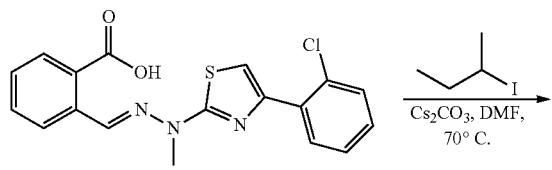

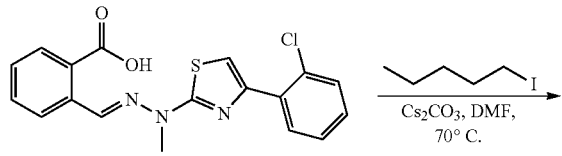

160 mg of pale yellow powder (yield 56%) was obtained according to the same synthesis method as that for B1. ¹H NMR (400 MHz, DMSO-d₆, ppm): δ 8.49 (s, 1H), 8.02 (dd, J=8.0, 1.2 Hz, 1H), 7.96 (dd, J=7.7, 1.8 Hz, 1H), 7.90 (dd, J=7.8, 1.4 Hz, 1H), 7.72-7.66 (m, 1H), 7.56-7.46 (m, 3H), 7.43 (td, J=7.5, 1.4 Hz, 1H), 7.37 (td, J=7.6, 1.9 Hz, 1H), 5.06 (h, J=6.3 Hz, 1H), 3.69 (s, 3H), 1.76-1.62 (m, 2H), 1.33 (d, J=6.3 Hz, 3H), 0.93 (t, J=7.5 Hz, 3H). ¹³C NMR (100 MHz, DMSO-d₆, ppm): δ 169.02, 166.68, 147.22, 136.57, 135.04, 133.49, 132.80, 131.62, 131.19, 130.87, 130.79, 129.81, 129.60, 129.43, 127.76, 126.84, 111.62, 73.57, 33.04, 28.71, 19.66, 10.04. HRMS (ESI) calcd for C$_{22}$H$_{22}$N$_3$O$_2$SCl [M+H]$^+$ 428.1121, found 428.1131. HPLC purity: 98.95%, Retention time=18.44 min.

(E)-4-(2-chlorophenyl)-2-[1-methyl-2-(2-pentyloxyformylbenzylidene)hydrazino]thiazole B6

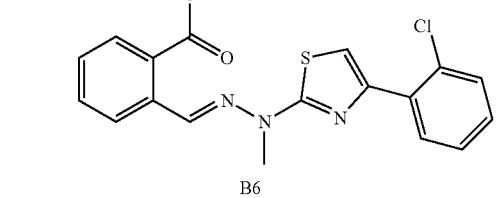

130 mg of pale yellow powder (yield 55%) was obtained according to the same synthesis method as that for B1. ¹H NMR (400 MHz, DMSO-d₆, ppm): δ 8.48 (s, 1H), 8.04-7.85 (m, 3H), 7.69 (t, J=7.6 Hz, 1H), 7.59-7.31 (m, 5H), 4.30 (t, J=6.5 Hz, 2H), 3.68 (s, 3H), 1.78-1.64 (m, 2H), 1.35 (s, 4H), 0.88 (t, J=6.7 Hz, 3H). ¹³C NMR (100 MHz, DMSO-d₆, ppm): δ 168.99, 167.18, 147.22, 136.69, 135.08, 133.50, 132.80, 131.62, 131.19, 130.87, 130.77, 129.60, 129.57, 129.42, 127.76, 127.01, 111.60, 65.64, 33.05, 28.26, 28.19, 22.28, 14.33. HRMS (ESI) calcd for C$_{23}$H$_{24}$N$_3$O$_2$SCl [M+H]$^+$ 442.1278, found 442.1265. HPLC purity: 98.21%, Retention time=22.10 min.

(E)-4-(2-chlorophenyl)-2-[1-methyl-2-(2-hexyloxyformylbenzylidene)hydrazino]thiazole B7

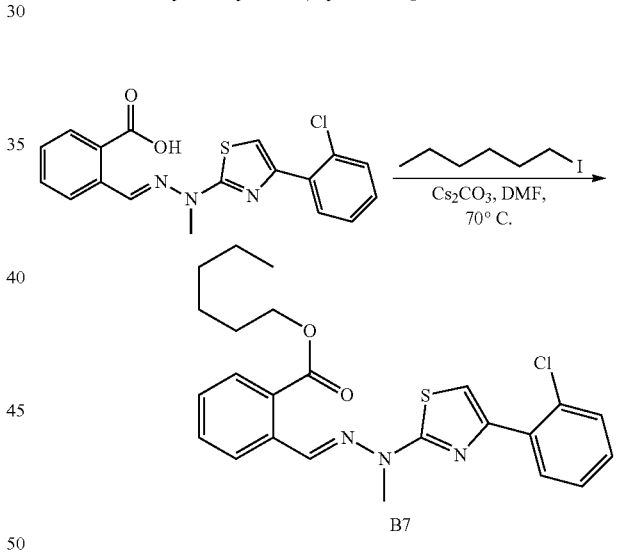

170 mg of pale yellow powder (yield 49%) was obtained according to the same synthesis method as that for B1. ¹H NMR (400 MHz, DMSO-d₆, ppm): δ 8.48 (s, 1H), 8.02-7.94 (m, 2H), 7.88 (dd, J=7.8, 1.3 Hz, 1H), 7.72-7.66 (m, 1H), 7.58-7.46 (m, 3H), 7.43 (td, J=7.6, 1.4 Hz, 1H), 7.36 (td, J=7.6, 1.9 Hz, 1H), 4.30 (t, J=6.6 Hz, 2H), 3.68 (s, 3H), 1.75-1.66 (m, 2H), 1.41-1.25 (m, 6H), 0.88-0.82 (m, 3H). ¹³C NMR (100 MHz, DMSO-d₆, ppm): δ 237.52, 235.49, 158.25, 145.81, 132.69, 131.51, 131.35, 131.07, 130.76, 129.48, 129.31, 127.65, 126.94, 125.32, 124.37, 91.91, 65.55, 32.94, 31.27, 28.41, 25.58, 22.38, 14.24. HRMS (ESI) calcd for C$_{24}$H$_{26}$N$_3$O$_2$SCl [M+H]$^+$ 456.1434, found 456.1410. HPLC purity: 97.55%, Retention time=17.44 min.

(E)-4-(2-chlorophenyl)-2-[1-methyl-2-(2-cyclohexyloxyformylbenzylidene)hydrazino]thiazole B8

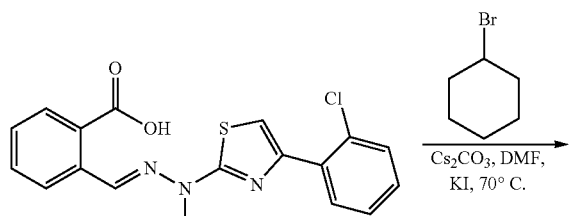

130 mg of pale yellow powder (yield 53%) was obtained according to the same synthesis method as that for B1. $^1$H NMR (100 MHz, DMSO-d$_6$, ppm): δ 8.50 (s, 1H), 8.02 (d, J=8.0, 1.3 Hz, 1H), 7.96 (dd, J=7.7, 1.8 Hz, 1H), 7.90 (dd, J=7.9, 1.4 Hz, 1H), 7.72-7.66 (m, 1H), 7.56-7.47 (m, 3H), 7.43 (td, J=7.5, 1.5 Hz, 1H), 7.37 (td, J=7.6, 1.9 Hz, 1H), 5.03-4.95 (m, 1H), 3.69 (s, 3H), 1.98-1.90 (m, 2H), 1.79-1.65 (m, 2H), 1.61-1.49 (m, 3H), 1.47-1.29 (m, 3H). $^{13}$C NMR (100 MHz, DMSO-d$_6$, ppm): δ 169.02, 166.44, 147.22, 136.65, 135.03, 133.50, 132.81, 131.62, 131.20, 130.87, 129.89, 129.61, 129.43, 127.77, 126.82, 111.62, 73.78, 33.06, 31.51, 25.32, 23.69. HRMS (ESI) calcd for C$_{24}$H$_{24}$N$_3$O$_2$SCl [M+H]$^+$ 454.1278, found 454.1294. HPLC purity: 97.32%, Retention time=11.53 min.

(E)-4-(2-chlorophenyl)-2-[1-methyl-2-(2-phenylethoxyformylbenzylidene)hydrazino]thiazole B9

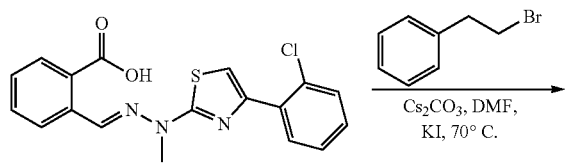

100 mg of yellow powder (yield 46%) was obtained according to the same synthesis method as that for B1, except that an equimolar amount of potassium iodide was added. $^1$H NMR (400 MHz, DMSO-d$_6$, ppm): δ 8.40 (s, 1H), 8.02-7.93 (m, 2H), 7.84-7.80 (m, 1H), 7.71-7.66 (m, 1H), 7.56-7.47 (m, 3H), 7.43 (td, J=7.5, 1.5 Hz, 1H), 7.37 (td, J=7.6, 1.9 Hz, 1H), 7.31 (d, J=4.3 Hz, 4H), 7.26-7.19 (m, 1H), 4.54 (t, J=6.7 Hz, 2H), 3.61 (s, 3H), 3.06 (t, J=6.7 Hz, 2H). $^{13}$C NMR (100 MHz, DMSO-d$_6$, ppm): δ 168.88, 166.89, 147.13, 138.34, 136.45, 135.03, 133.42, 132.77, 131.52, 131.10, 130.76, 130.60, 129.49, 129.24, 128.77, 127.65, 126.90, 126.80, 111.49, 65.95, 34.67, 32.92. HRMS (ESI) calcd for C$_{26}$H$_{22}$N$_3$O$_2$SCl [M+H]$^+$ 476.1121, found 476.1201. HPLC purity: 98.35%, Retention time=16.44 min.

(pivaloyloxy)methyl (E)-2-((2-(4-(2-chlorophenyl)thiazol-2-yl)-2-methylhydrazono)methyl)benzoate B10

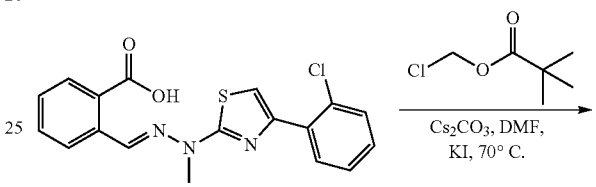

120 mg of bright yellow powder (yield 57%) was obtained according to the same synthesis method as that for B9. $^1$H NMR (400 MHz, DMSO-d$_6$, ppm): δ 8.44 (s, 1H), 8.03 (d, J=8.0, 1.2 Hz, 1H), 7.96 (dd, J=7.7, 1.9 Hz, 1H), 7.89-7.85 (m, 1H), 7.77-7.71 (m, 1H), 7.57-7.53 (m, 2H), 7.49 (s, 1H), 7.43 (td, J=7.5, 1.4 Hz, 1H), 7.37 (td, J=7.6, 1.9 Hz, 1H), 5.99 (s, 2H), 3.69 (s, 3H), 1.17 (s, 9H). $^{13}$C NMR (100 MHz, DMSO-d$_6$, ppm): δ 176.91, 168.94, 165.74, 147.24, 136.17, 135.56, 133.60, 133.48, 131.64, 131.20, 130.97, 130.87, 129.62, 129.56, 128.04, 127.77, 127.18, 111.73, 89.14, 80.79, 33.07, 26.96. HRMS (ESI) calcd for C$_{24}$H$_{24}$N$_3$O$_4$SCl [M+H]$^+$ 486.1176, found 486.1256. HPLC purity: 97.64%, Retention time=13.15 min.

((isopropoxycarbonyl)oxy)methyl (E)-2-((2-(4-(2-chlorophenyl)thiazol-2-yl)-2-methylhydrazono)methyl)benzoate B11

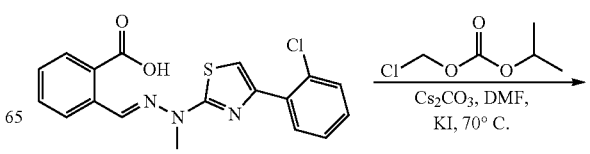

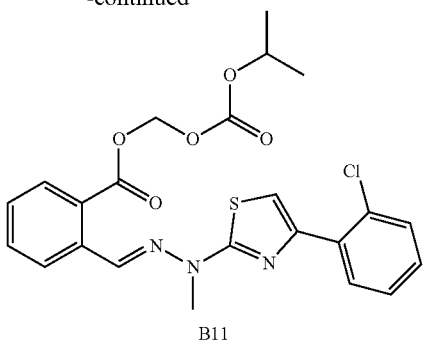

B11

90 mg of firefly yellow powder (yield 54%) was obtained according to the same synthesis method as that for B9. $^1$H NMR (400 MHz, DMSO-$d_6$, ppm): δ 8.74 (s, 1H), 8.30 (d, J=8.0, 1.3 Hz, 1H), 8.15 (dd, J=8.0, 1.4 Hz, 1H), 8.09 (dd, J=7.8, 1.8 Hz, 1H), 7.74-7.67 (m, 1H), 7.54-7.47 (m, 2H), 7.44-7.36 (m, 2H), 7.36-7.28 (m, 2H), 6.10 (s, 2H), 5.07-5.00 (m, 1H), 3.86 (s, 3H), 1.42 (d, J=6.2 Hz, 6H). $^{13}$C NMR (100 MHz, DMSO-$d_6$, ppm): δ 169.03, 165.22, 153.36, 147.30, 136.67, 134.75, 133.43, 133.13, 131.72, 131.21, 131.12, 130.39, 128.36, 128.31, 126.86, 126.71, 126.38, 110.68, 82.11, 73.18, 32.67, 21.57. HRMS (ESI) calcd for $C_{23}H_{22}N_3O_5SCl$ [M+H]$^+$ 488.0969, found 488.1046. HPLC purity: 96.65%, Retention time=17.44 min.

(E)-4-(2-chlorophenyl)-2-[1-methyl-2-(2-(chloro-formylbenzylidene)hydrazino]thiazole 12b

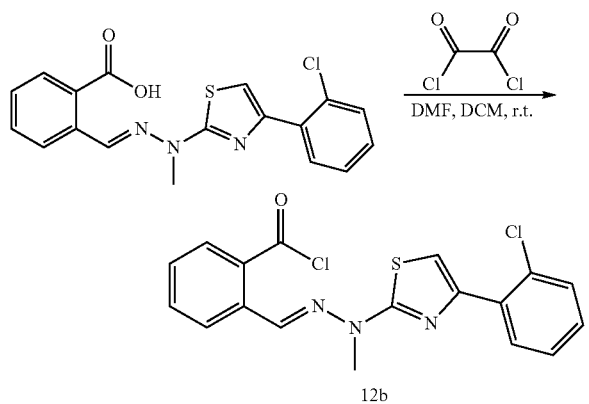

12b

Compound B (0.2 g, 0.54 mmol) was weighed into a 50 mL two-necked flask, and 10 mL of dichloromethane and 2 drops of N,N-dimethylformamide (DMF) were added, and stirred for 10 minutes in an ice bath. Oxalyl chloride (0.13 g, 1.08 mmol) was dissolved in 5 mL of dichloromethane and added dropwise to the reaction flask. The reaction mixture was placed in the ice bath for another half an hour, the ice bath was removed, the reaction mixture was warmed to room temperature for 2 h, and the reaction was detected: the reaction solution was taken into a tube, methanol was added with shaking, then water and ethyl acetate were added and allowed to stand, the upper organic phase was taken and detected by TLC to determine that the raw material point basically disappeared. The preparation of acid chloride was successful. The solvent of the reaction solution was evaporated to dryness in vacuo to give a yellow liquid, which was directly used in the next step.

(E)-4-(2-chlorophenyl)-2-[1-methyl-2-(2-((N,N-dimethyl)formylbenzylidene)hydrazino]thiazole B12

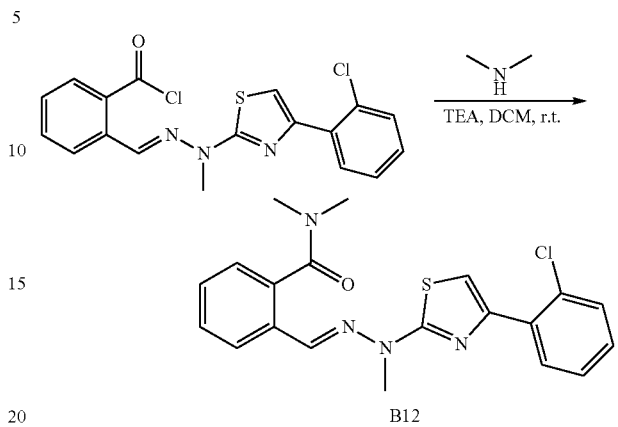

B12

Dimethylamine (24 mg, 0.54 mmol), triethylamine (55 mg, 0.54 mmol) and 10 mL of anhydrous dichloromethane were added into a 50 mL single-mouth reaction flask and electromagnetic-stirred for 15 minutes in an ice bath. The freshly prepared acid chloride solution in dichloromethane was added dropwise to the reaction flask, and maintained in an ice bath for 30 minutes. The reaction was warmed to room temperature for 10 hours, and detected by TLC. After the reaction was completed, 5 ml of water and 5 ml of dichloromethane were added into the reaction mixture, and stirred for 10 minutes. The mixture was allowed to stand for stratification. The organic phase was taken, the aqueous phase was extracted for three times with dichloromethane, and organic phases were combined and dried. The solvent was evaporated to dryness in vacuo and purified through column chromatography to give 50 mg of off-white solid powder (yield 25%). $^1$H NMR (400 MHz, DMSO-$d_6$, ppm): δ 7.96 (dd, J=8.0, 2 Hz, 1H), 7.87 (d, J=7.6 Hz, 1H), 7.73 (s, 1H), 7.55-7.29 (m, 7H), 3.65 (s, 3H), 3.07 (s, 3H), 2.80 (s, 3H). $^{13}$C NMR (100 MHz, DMSO-$d_6$, ppm): δ 169.57, 168.91, 147.14, 136.30, 135.65, 133.52, 131.62, 131.34, 131.19, 130.86, 129.58, 129.46, 127.76, 127.59, 127.22, 111.59, 38.62, 34.90, 32.95. HRMS (ESI) calcd for $C_{20}H_{19}N_4OSCl$ [M+H]$^+$ 399.0968, found 399.1048. HPLC purity: 96.75%, Retention time=11.14 min.

Example 2 (Activity Evaluation)

1. Experimental Material 1.1 Experimental Animal

BALB/c male mice (each 18-22 g) of SPF level were purchased from Shanghai Slack Laboratory Animal Co., Ltd. and were used in experiments after adaptive feeding for 7 days.

1.2 Reagents 2,4,6-trinitrobenzenesulfonic acid (TNBS) was purchased from Sigma (USA), sulfasalazine tablets (SASP, 0.25 g/tablet) were purchased from Shanghai Sanwei Pharmaceutical Co., Ltd., anhydrous ethanol was purchased from Shanghai Titan Technology. Co., Ltd., chloral hydrate was purchased from Jiangsu Qiangsheng Functional Chemical Co., Ltd., sodium chloride was purchased from Sinopharm Chemical Reagent Co., Ltd., 37%~40% formaldehyde solution was purchased from Shanghai Lingfeng Chemical Reagent Co., Ltd., sodium carboxymethyl cellulose was purchased from Shanghai Jingchun Biochemical Technology Co., Ltd., paraffin was purchased from Leica (Germany), xylene was purchased from Shanghai Lingfeng Chemical Reagent Co., Ltd., hematoxylin and eosin (H&E) staining kit was purchased from Biyuntian Biotechnology Research Institute, hydrochloric acid was purchased from Shanghai Lingfeng Chemical Reagent Co., Ltd., and neutral gum was purchased from Sinopharm Chemical Reagent Co., Ltd.

1.3 Instruments Used in Experiment

The electronic balance was purchased from Shanghai Jingtian Electronic Instrument Co., Ltd., the precision electronic balance was purchased from METTLER TOLEDO, the vernier caliper was purchased from Harbin Measuring and Cutting Tool Group Co., Ltd., the microscope was purchased from Nikon, the paraffin slicer was purchased from Leica (Germany), and the electric thermostat blast drying oven was purchased from Shanghai Yiheng Scientific Instrument Co., Ltd.

2. Experiment Methods 2.1 Breeding of Experiment Animal

BALB/c male mice were kept in an animal cage (daylight and darkness of 12 hours, respectively) at a temperature of 20-25° C. and relative humidity of 50-60%, free access to food and water.

2.2 Group of Experiment Animals

Groups and dosages for the experiment animals are shown in Table 1. Mice were randomly divided into normal control group, trinitrobenzenesulfonic acid (TNBS) model group, drug treatment group and positive drug control group (sulfasalazine 500 mg/kg).

The mice were randomly divided into four groups, and the grouping and daily administration are shown in Table 1:

TABLE 1

Mice grouping and daily administration

| Group | Number of mice | Administration | Administration mode |
|---|---|---|---|
| Normal control group (Control) | 10 | CMC-Na 0.2 ml | ig |
| TNBS model group (Model) | 10 | CMC-Na 0.2 ml | ig |
| Drug treatment group | 10 | Comopund 20 mg/kg | ig |
| Positive drug control group | 10 | Sulfasalazine (500 mg/kg) | ig |

2.3 Establishment of TNBS-Induced Mice Ulcerative Colitis Model and Administration All of the mice in model group and administration group were shaved in the abdomen (area 2×2 cm) and sensitized with 1% TNBS (dissolved in 50% ethanol). On the $7^{th}$ day, the mice were fasted, but not water. After 24 hours, the mice were anesthetized through intraperitoneal injection of 0.1 ml of 10% chloral hydrate and 2% TNBS was used for lavation to establish a mouse model of ulcerative colitis. A gavage needle for rat was inserted into the colon of a mouse, the tip of the needle was about 3~3.5 cm away from the anus, and 0.1 ml of modeling solution (5% TNBS and deionized water were mixed at a volume ratio of 4:1, and the obtained solution was mixed with absolute ethanol at a volume ratio of 1:1, so as to obtain the modeling solution) was injected. The mice were put back into the cage and wake up naturally. The mice in the normal control group were injected with 0.12 ml of solvent (50% ethanol solution) by the same manner. 2 modeling mice were randomly sacrificed after 24 hours of modeling, and changes in colon were observed to confirm whether the modeling was successful.

Administration was started on the day of modeling (using 0.5% sodium carboxymethylcellulose, CMC-Na) for 7 consecutive days. The body weight was weighed daily, and the mice were observed for mental state, stool characteristics, fur state, food intake, and the like.

2.4 Collection of Samples

At 24 hours after the last administration, the mice were sacrificed by cervical dislocation, the peritoneum was cut open, and the whole colon was taken. The intestine was cut longitudinally along the mesenteric margin, rinsed with ice physiological saline, placed on ice, and the pathological changes of the colon were observed. The fat and mesentery were removed, the water was blotted with filter paper, the weight of the colon was weighed and the length was measured. The colon was fixed in 4% formaldehyde for more than 24 hours, dehydrated, paraffin-embedded and H&E stained, and the pathological sections were observed.

2.5 Evaluation Index 2.5.1 General Observation

The mice were observed and recorded daily for mental state, fur color, and activities. The mice was weighed daily and observed for the stool traits. The body weight index according to the disease activity index (DAI) is as follows:

Weight: constant weight, 0 points; compared with normal situation, the body weight decreased by 1% to 5%, 1 point; 6% to 10%, 2 points; 11% to 15%, 3 points; greater than 15%, 4 points.

2.5.2 Change in Weight/Length Ratio of Colon

After the colon of a mouse was removed, the weight of the colon was measured with a precision electronic balance, the length was measured with a vernier caliper, and the weight/length ratio of the colon was calculated.

2.5.3 Observation of Gross Morphological Damage of Colon

After the colon was taken, the colon was observed for adhesion with other tissues, ulceration and inflammation, and recorded scores. The criteria for scores were: no adhesion, no ulcer, no inflammation, 0 points; mild adhesion, local congestion, no ulcer, 1 point; severe adhesion, 1 ulcer (area less than 1 cm), no obvious inflammation, 2 points; more than 1 ulcers (area less than 1 cm) with inflammation, 3 points; 2 severe ulcers (area greater than 1 cm) with inflammation, 4 points; and 1 point for each 1 cm increase in ulcer area.

2.5.4 Histopathological Observation for Colon

Pathological changes of colon tissue were observed under light microscope, and the scores were recorded. The criteria for scores are as follows:

1) Epithelial cells: normal morphology, 0 points; loss of goblet cells, 1 point; large loss of goblet cells, 2 points; loss of crypt cells, 3 points; large loss of crypt cells, 4 points.

2) Infiltration of inflammatory cells: no infiltration, 0 points; infiltration in the basal layer of the crypt, 1 point; infiltration to the muscular layer of the mucosa, 2 points; infiltration to the muscular layer of the mucosa with mucosal thickening and obvious edema, 3 points; infiltration to the submucosal layer, 4 points.

2.6 Statistical Analysis

Data were expressed as mean±standard deviation (mean±S.E.M.), data were analyzed using SPSS statistical software, and one-way ANOVA and Tukey's HSD post hoc test were used for comparison between groups. $p<0.05$ was considered statistically significant.

3. Experimental Results and Analysis
3.1 General Observation

Compared with the normal control group, stool characteristics of the mice in TNBS model group began to change on the $3^{rd}$ day after modeling, and diarrhea symptoms occurred. After the $4^{th}$ day, diarrhea, bloody stools, listlessness, decreased activity, decreased diet, loose and dull fur, and significant decline in weight appeared; in drug treatment group and positive drug control group, diarrhea symptoms appeared on the $3^{rd}$ day of modeling, and diarrhea, bloody stools, mental dysfunction, decreased activity, decreased diet, loose and dull fur, weight loss appeared after the $4^{th}$ day, the symptoms of which, however, are milder than those in the TNBS model group. The weight loss is shown in Table 2:

TABLE 2

Weight loss of mice

| Group | | Ratio of weight loss | Score |
|---|---|---|---|
| Normal control group | | −0.85 ± 1.73 | 0 |
| TNBS model group | | 19.32 ± 2.25** | 4 |
| Positive drug control group | | 1.54 ± 3.72## | 1 |
| Drug treatment group (No. of compound) | 1 | 2.61 ± 4.53## | 1 |
| | 2 | 1.22 ± 3.68## | 1 |
| | 3 | 4.26 ± 4.65# | 2 |
| | 8 | 1.07 ± 2.98## | 1 |
| | 8-1 | 3.72 ± 1.60## | 1 |
| | 9 | 3.29 ± 4.70# | 1 |
| | 10 | 1.92 ± 3.20## | 1 |
| | 12 | 2.33 ± 2.99## | 1 |
| | 16 | 3.55 ± 1.47## | 1 |
| | 23 | 6.27 ± 2.76# | 3 |
| | 55 | 2.74 ± 4.61## | 1 |

Note:
Compared with the normal control group,
**$p < 0.01$: compared with the model group,
$p < 0.05$,
$p < 0.01$ 3.2 Changes in Weight/Length Ratio of Colon The weight, length of the colon and ratio thereof are shown in Table 3:

TABLE 3

Changes in weight/length ratio of mice

| Group | | Length of the colon (cm) | Weight of the colon (g) | weight/length ratio (average) |
|---|---|---|---|---|
| Normal control group | | 6.460 ± 0.320 | 0.142 ± 0.011 | 0.022 |
| TNBS model group | | 4.890 ± 0.589 | 0.152 ± 0.035 | 0.031* |
| Positive drug control group | | 5.814 ± 0.465 | 0.145 ± 0.018 | 0.025# |
| Drug treatment group (No. of compound) | 1 | 5.575 ± 0.452 | 0.162 ± 0.027 | 0.029# |
| | 3 | 5.699 ± 0.368 | 0.159 ± 0.023 | 0.028# |
| | 8 | 6.005 ± 0.452 | 0.157 ± 0.027 | 0.026# |
| | 9-1 | 5.985 ± 0.363 | 0.152 ± 0.023 | 0.025# |
| | 10 | 6.321 ± 0.436 | 0.162 ± 0.045 | 0.026# |
| | 12 | 5.075 ± 0.468 | 0.154 ± 0.012 | 0.030# |
| | 15 | 5.546 ± 0.402 | 0.163 ± 0.023 | 0.029# |
| | 17 | 5.124 ± 0.332 | 0.159 ± 0.034 | 0.030# |
| | 21 | 4.986 ± 0.452 | 0.158 ± 0.025 | 0.032# |
| | 23 | 4.997 ± 0.476 | 0.153 ± 0.027 | 0.030# |
| | 55 | 5.675 ± 0.222 | 0.148 ± 0.033 | 0.026# |
| | 58 | 5.575 ± 0.392 | 0.162 ± 0.028 | 0.029# |

Note:
Compared with the normal control group,
*$p < 0.05$: compared with the model group,
$p < 0.05$ The weight/length ratio of the TNBS model group was significantly larger than that of the normal control group, indicating that the hyperemia and swelling of the model group were more serious, while the weight/length ratio of the drug treatment group and the positive drug control group was significantly lower than that of the model group, indicating that the compound of the present invention and the positive drug, Sulfasalazine can reverse the congestion and edema of colon induced by TNBS in mice.

3.3 Gross Morphological Damage and Histopathological Observation of Colon

By observing the gross morphology and histopathological sections of the colon, it was found that, compared with the normal control group, obvious damages can be found in the model group, which are congestion and swelling, severe ulceration, and infiltration of inflammatory cells. In the drug treatment group and the positive control group, such damages were significantly improved (as shown in FIG. 1).

The gross morphological damages and histopathology scores of the colon are summarized in Table 4.

TABLE 4

Observations of gross morphological damages and histopathology scores of the colon

| Group | | Scores of gross morphological damages | Histopathology scores |
|---|---|---|---|
| Normal control group | | 0 | 0 |
| TNBS model group | | 5.42 ± 0.73** | 5.82 ± 0.98** |
| Positive drug control group | | 0.81 ± 0.69 | 1.71 ± 0.69## |
| Drug treatment group (No. of compound) | 1 | 2.32 ± 0.69* | 2.54 ± 0.62## |
| | 2 | 3.37 ± 0.60* | 3.10 ± 0.55# |
| | 8 | 1.42 ± 0.78* | 1.59 ± 0.68## |
| | 9-1 | 3.63 ± 0.71* | 3.94 ± 0.51# |
| | 10 | 1.02 ± 0.41* | 2.09 ± 0.44## |
| | 16 | 2.22 ± 0.54* | 2.54 ± 0.49## |
| | 20 | 3.33 ± 0.59* | 3.65 ± 0.42# |
| | 21 | 2.31 ± 0.79* | 2.54 ± 0.62## |
| | 23 | 2.02 ± 0.60* | 2.32 ± 0.58## |
| | 55 | 1.99 ± 0.52* | 1.68 ± 0.32## |
| | 58 | 4.32 ± 0.79* | 3.59 ± 0.61# |

Note:
Compared with the normal control group,
**$p < 0.01$: compared with the TNBS model group,
$p < 0.05$,
$p < 0.01$

DISCUSSION

From the results of examination of the therapeutic activities of the compound of the present invention against ulcerative colitis at the animal level, it is understood that the compound of the present invention exhibits excellent therapeutic activities against ulcerative colitis, and some of the compounds exhibit therapeutic activities against ulcerative colitis comparable to that of the positive control drug. Therefore, the present invention lays a new material foundation for the development of new drugs for treating ulcerative colitis with low toxicity, high efficiency and safety.

All documents mentioned in the present application are hereby incorporated by reference in their entireties as if each document is separately cited as a reference. In addition, it is to be understood that various modifications and changes may be made by a skilled person in the art, after reading the above teachings of the present invention, and the equivalent forms also fall within the scope defined by the claims appended hereto.

The invention claimed is:

1. A method for treating inflammatory bowel disease, comprising administrating a compound of formula II or a pharmaceutically acceptable salt or ester thereof or a pharmaceutical composition to a subject in need of the treatment of inflammatory bowel disease, wherein the pharmaceutical composition comprises a compound of formula II or a pharmaceutically acceptable salt or ester thereof and a pharmaceutically acceptable carrier or excipient; and the compound of formula II is represented by:

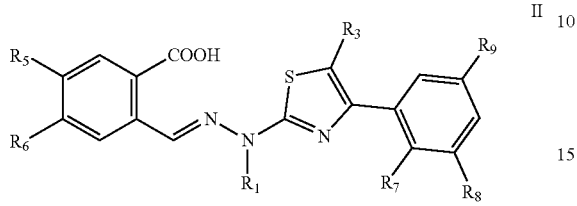

Wherein,
$R_1$ is a substituted or unsubstituted $C_1$-$C_3$ alkyl;
$R_5$ and $R_6$ are independently selected from the group consisting of H, halogen and a substituted or unsubstituted $C_1$-$C_3$ alkyl;
$R_3$ is selected from the group consisting of H and a substituted or unsubstituted $C_1$-$C_3$ alkyl; and
$R_7$, $R_8$ and $R_9$ are independently selected from the group consisting of H and halogen.

2. A method for treating inflammatory bowel disease, comprising administrating a compound or a pharmaceutically acceptable salt or ester thereof or a pharmaceutical composition to a subject in need of the treatment of inflammatory bowel disease, wherein the pharmaceutical composition comprises a compound or a pharmaceutically acceptable salt or ester thereof and a pharmaceutically acceptable carrier or excipient; and the compound is selected from the group consisting of:

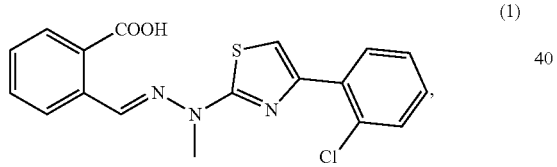

(1)

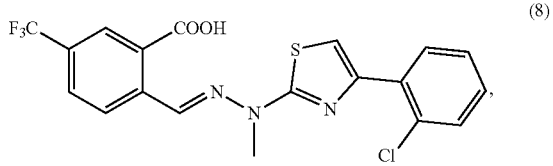

(8)

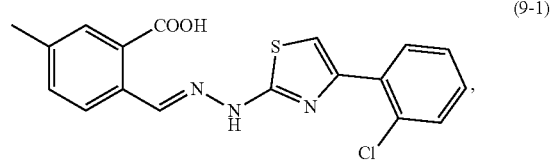

(9-1)

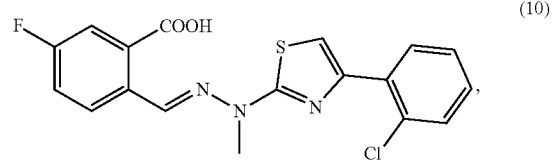

(10)

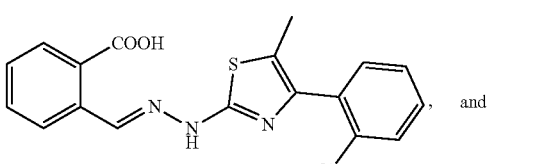

(15), and

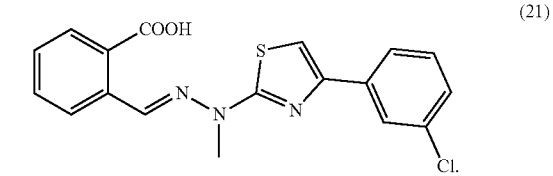

(21)

3. The method of claim 1, wherein the inflammatory bowel disease is ulcerative colitis.

4. The method of claim 2, wherein the inflammatory bowel disease is ulcerative colitis.

* * * * *